(12) United States Patent
Chicoine et al.

(10) Patent No.: US 7,928,296 B2
(45) Date of Patent: *Apr. 19, 2011

(54) MAIZE EVENT DP-098140-6 AND COMPOSITIONS AND METHODS FOR THE IDENTIFICATION AND/OR DETECTION THEREOF

(75) Inventors: Timothy K. Chicoine, St. Charles, IA (US); Jeffery W. Derry, Guthrie Center, IA (US); Christine B. Hazel, Port Deposit, MD (US); Donglong Liu, Johnston, IA (US); Billy Fred McCutchen, College Station, TX (US); Wayne J. Mehre, Urbandale, IA (US); Kenneth A. Peeples, Wilmington, DE (US); David W. Saunders, Dallas Center, IA (US); Gan-Yuan Zhong, Urbandale, IA (US)

(73) Assignees: Pioneer Hi-Bred International, Inc., Johnston, IA (US); E.I. DuPont de Nemours and Co., Wilmington, DE (US)

( * ) Notice: Subject to any disclaimer, the term of this patent is extended or adjusted under 35 U.S.C. 154(b) by 608 days.

This patent is subject to a terminal disclaimer.

(21) Appl. No.: 11/869,973

(22) Filed: Oct. 10, 2007

(65) Prior Publication Data

US 2008/0108072 A1 May 8, 2008

Related U.S. Application Data

(60) Provisional application No. 60/855,308, filed on Oct. 30, 2006, provisional application No. 60/940,567, filed on May 29, 2007.

(51) Int. Cl.
*C12N 15/82* (2006.01)
*A01H 5/10* (2006.01)
(52) U.S. Cl. ............... 800/300.1; 800/266; 800/298
(58) Field of Classification Search ............... None
See application file for complete search history.

(56) References Cited

U.S. PATENT DOCUMENTS

| | | | |
|---|---|---|---|
| 7,405,074 | B2 | 7/2008 | Castle et al. |
| 7,687,434 | B2 | 3/2010 | DeBillot et al. |
| 2003/0226166 | A1 | 12/2003 | Falco et al. |
| 2004/0082770 | A1 | 4/2004 | Castle et al. |
| 2004/0123352 | A1 | 6/2004 | Plaisted et al. |
| 2005/0246798 | A1 | 11/2005 | Castle et al. |
| 2006/0070139 | A1 | 3/2006 | Bing et al. |
| 2007/0061917 | A1 | 3/2007 | McCutchen et al. |
| 2007/0130641 | A1 | 6/2007 | McCutchen et al. |
| 2008/0051288 | A1 | 2/2008 | Cressman, Jr. et al. |
| 2009/0011938 | A1 | 1/2009 | Castle et al. |
| 2009/0137395 | A1* | 5/2009 | Chicoine et al. ........... 504/206 |

FOREIGN PATENT DOCUMENTS

| | | |
|---|---|---|
| WO | WO 98/39419 | 9/1998 |
| WO | WO 02/36782 A2 | 5/2002 |
| WO | WO 03/013224 | 2/2003 |
| WO | WO 03/052073 A2 | 6/2003 |
| WO | WO 03/092360 A2 | 11/2003 |
| WO | WO 2004/099447 | 11/2004 |
| WO | WO 2005/012515 A2 | 2/2005 |
| WO | WO 2006/039376 A2 | 4/2006 |
| WO | WO 2007/024782 A2 | 3/2007 |

OTHER PUBLICATIONS

Hegstad, Jeff, "Herbicide Efficacy and Yield Evaluations", CSB Meeting, Feb. 22, 2007.
Hegstad, Jeff, "Herbicide Efficacy and Yield Evaluations", ASA/CSSA/SSSA 2007 International Annual Meetings.
Yang, L., et al., "Event Specific Qualitative and Quantitative Polymerase Chain Reaction Detection of Genetically Modified MON863 Maize Based on the 5'-Transgene Integration Sequence", *Journal of Agricultural and Food Chemistry*, 2005, pp. 9312-9318, vol. 53.
Castle, L.A., et al., "Discovery and Directed Evolution of a Glyphosate Tolerance Gene", *Science*, vol. 304, No. 21, May 21, 2004, pp. 1151-1154.
Green, J.M., "Review of Glyphosate and ALS-Inhibiting Herbicide Crop Resistance and Resistant Weed Management", *Weed Technology*, 2007, vol. 21, pp. 547-558.
Rood, T.A., et al.., "Petition for the Determination of Nonregulated Status for Herbicide Tolerant 356043 Soybean", Sep. 27, 2006.
Terry, C.F. and Harris, N., "Event-Specific Detection of Roundup Ready Soya using two Different Real Time PCR Detection Chemistries",*Eur. Food Res Technol.*, vol. 213, 2001, pp. 425-431.
Windels, P., et al., "Characterization of the Roundup Ready Soybean Insert", *Eur Food Res Technol.*, vol. 213, 2001, pp. 107-112.
Windels, P., et al., "Development of a Line Specific GMO Detection Method: A Case Study", *Med. Fac. Landbouww. Univ. Gent.*, vol. 64, No. 5B, Sep. 22, 1999, pp. 459-462.

* cited by examiner

*Primary Examiner* — David H Kruse
(74) *Attorney, Agent, or Firm* — Alston & Bird LLP

(57) ABSTRACT

Compositions and methods related to transgenic glyphosate/ALS inhibitor-tolerant maize plants are provided. Specifically, the present invention provides maize plants having a DP-098140-6 event which imparts tolerance to glyphosate and at least one ALS-inhibiting herbicide. The maize plant harboring the DP-098140-6 event at the recited chromosomal location comprises genomic/transgene junctions having at least the polynucleotide sequence of SEQ ID NO:5 and/or 6. The characterization of the genomic insertion site of the DP-098140-6 event provides for an enhanced breeding efficiency and enables the use of molecular markers to track the transgene insert in the breeding populations and progeny thereof. Various methods and compositions for the identification, detection, and use of the maize DP-098140-6 events are provided.

9 Claims, 6 Drawing Sheets

SEQUENCE LISTING

```
<160> NUMBER OF SEQ ID NOS: 57

<210> SEQ ID NO 1
<211> LENGTH: 726
<212> TYPE: DNA
<213> ORGANISM: Artificial Sequence
<220> FEATURE:
<223> OTHER INFORMATION: right border junction of maize event
      DP-098140-6

<400> SEQUENCE: 1
atgaaaaagt ccaagtcgag caagggtacg taccgcggcc ggcggctaat tacggaggac      60
atgtcgtagt agctggtagt aaattaacac acgcgtacga gtagcggagt taaatggggg     120
catgcatgca gcaggacgtg gtattagtaa gcttactact ctagctttat ccatccatcc     180
atcgcgctag ctggctgcag gcacgggtta tcttatcttg tcgtccagag gacgacacac     240
ggccggccgg tgaagtaaaa gggagtaatc ttattttgcc aggacgaggg gcggtacatg     300
atattacaca cgtaccatgc atgcatatat gcatggacaa ggtacgtcgt cgtcgatcga     360
cgtcgatgca tatgtgtgta tgtatgtacg tgcataatgc atggtaccag ctgctggctt     420
atatatattt gtcaccgatc gatgcatgct gctgctctac acggtttgac actttaattt     480
```

```
gactcatcga tgaccttgct agatagtagc ggctcgtcaa ttaatgagcc atcaagttaa    540
caagagggca cgggcttgcg cgactgattc caccttatta acatacgccc tgcgcccgcg    600
cgtgctgtac gtacgagaat tcgaattac attaattcaa agctgtgtat gtatgtatat     660
atatatgtgc gttttttgt gtgtgtatgt ctctttgctt ggtctttctc tatcgatccc     720
cctctt                                                              726
```

```
<210> SEQ ID NO 2
<211> LENGTH: 1311
<212> TYPE: DNA
<213> ORGANISM: Artificial Sequence
<220> FEATURE:
<223> OTHER INFORMATION: left border junction of maize event DP-098140-6
<220> FEATURE:
<221> NAME/KEY: misc_feature
<222> LOCATION: 1263, 1264, 1265, 1266, 1267, 1268
<223> OTHER INFORMATION: n = A,T,C or G
<220> FEATURE:
<221> NAME/KEY: misc_feature
<222> LOCATION: 1263, 1264, 1265, 1266, 1267, 1268
<223> OTHER INFORMATION: n = A,T,C or G

<400> SEQUENCE: 2
ctgtacatgt aaccagcttt cctagaaaaa aaacacagta atatttacag tatacaataa    60
tgctcattga ttagatccaa aattatgaaa tgtatatatt ttttgccata acttttatta   120
cagtcttata ctgaagtaaa gttgtatcac gtcatgaaca tagaataaga ctgagatagt   180
tgactaatcc agtcatatcc tatagtacac tagtaaggtg catgtgctaa caatatgaca   240
aatctagtat ttctttatag tttatcatcc ataaatcgca aaatacctaa gcataatttt   300
atttgaatag agagagtact gcccgttatt gtatgaggta atgacttcca tatatacaac   360
atagtcataa gaacacaatt atgaaaaaaa tctatttaaa attgaaatgc gttgagatct   420
tgtcttgcat actaaacata gtaaatataa attaatgcat aaatgactgt tataacagac   480
aatgctggtg acaatagaca atgtactgaa tctaactgga tacgtaggat gctgctatct   540
tattcactca tagttattca gatagtggtc attcttttg acccatagaa aactgtgtgc   600
tataatacac caaaaggaaa gcaaagtgaa aaggaaactt tgaatagcca agaagactcg   660
gagtgcttca cgccttcacc tatcccacat aggtgatgag ctaagagtaa aatgtagatt   720
ctctcgagta ctgaatattg cctgcacttt tccttgcagt aaatacacct ttaatccatg   780
acgagagtcc actctttgag tccgtcttga gattcttcca ttgatcatac aacatgacct   840
cgaagtcctg atggagaaca acttatataa ttaaaactac aatacagaaa gttcctgaca   900
attaaaacct tggtggtgg catgccgtag gttaaaaaaa atagataatg acaacacaac    960
tggagacacg ctcttttgccg agtgctcaca cgtttgctga gagcgagcac tcggcaaata  1020
tatgatttgc cgaataccac cctcctcggc aaaacaatac actaggcaaa aaggtagttt   1080
cccatcacca tgatgcccgc cgttaatgta ccttctatgc cgagtatgtt ggcgctcagc   1140
aaagagatcg ttaccggcgt ttgtttcacc aagagctctt tgacgagtgt ggcacacgac   1200
aaaacctttt gccgagtgta attagtcgtt tgccaagtga ctggtgcagt tggcaaagga   1260
gtnnnnnntt atgtgtgggc aaaatgatat atggtgccag ttagggctag c            1311
```

```
<210> SEQ ID NO 3
<211> LENGTH: 7388
<212> TYPE: DNA
<213> ORGANISM: Artificial Sequence
<220> FEATURE:
<223> OTHER INFORMATION: complete transgene in maize event DP-098140-6
```

```
<400> SEQUENCE: 3
tgatagttta aactgaaggc gggaaacgac aatctgatca tgagcggaga attaagggag      60
tcacgttatg accccgccg atgacgcggg acaagccgtt ttacgtttgg aactgacaga     120
accgcaacgt tgaaggagcc actcagcaag ctgggccccc cctcgaggtc ggccgcattc    180
gcaaaacaca cctagactag atttgttttg ctaacccaat tgatattaat tatatatgat    240
taatatttat atgtatatgg atttggttaa tgaaatgcat ctggttcatc aaagaattat    300
aaagacacgt gacattcatt taggataaga aatatggatg atctctttct cttttattca    360
gataactagt aattacacat aacacacaac tttgatgccc acattatagt gattagcatg    420
tcactatgtg tgcatccttt tatttcatac attaattaag ttggccaatc cagaagatgg    480
acaagtctag gttaactgac tagctagtca gtacacagtc ctgccatcac catccaggat    540
catatccttg aaagccccac cactagggat cataggcaac acatgctcct ggtgtgggac    600
gattatatcc aagaggtacg gccctggagt ctcgagcatc ttctttatcg ctgcgcggac    660
ttcgttcttc tttgtcacac ggaccgctgg aatgttgaac cctttggcga tcgtcacgaa    720
atctggatat atctcacttt cattctctgg gtttcccaag tatgtgtgcg ctctgttggc    780
cttatagaac ctgtcctcca actgcaccac catccccagg tgctggttgt ttagcacaaa    840
gaccttcacc gggaggttct caattcggat catagctagc tcctgaacgt tcatgagaaa    900
gctaccatct ccatcgatgt caacaacagt gacacctggg ttggccacag aagcaccagc    960
agcagccggc aaaccaaatc ccatagcccc aagaccagct gaagacaacc actgccttgg   1020
ccgcttgtaa gtgtagtact gtgccgccca catctggtgc tgcccaacac ctgtgccgat   1080
gatggcctcg cctttcgtca gctcatcaag aacctgaata gcatattgtg gctggatctc   1140
ctcattagat gttttatacc caagggggaa ttccctcttc tgctgatcca actcatcgtt   1200
ccatgagcca aagtcaaagc tcttctttga tgtgcttcct tcaagaagag cattcatgcc   1260
ctgcaaagca agcttaacat ctgcacagat ggacacatgt ggctgcttgt tcttgccaat   1320
ctcagccgga tcaatatcaa cgtgcacaat cttagccctg cttgcaaaag cctcaatctt   1380
ccctgtcacg cgatcatcaa accgcacacc aagtgcaagc aacagatcgg ccttatccac   1440
tgcataattt gcatacaccg tcccatgcat acctagcatg cgcagagaca gtgggtcgtc   1500
gctggggaag ttgccgaggc ccataagagt agttgtgacc gggattccag tcagctccac   1560
aaagcgtcgc aactcctcac cagatgctgc gcagccaccg cccacataaa gaacagggcg   1620
ccgcgattca ccaacaagac gcagcacctg ctcaagcaac tcagtcgcag ggggcttggg   1680
aaggcgcgca atgtacccag gcagactcat gggcttgtcc cagacaggca ccgccatctg   1740
ctgctggatg tccttgggga tgtcgacaag caccggccct ggtcgaccag aggaggcgag   1800
gaagaaagcc tcctgcacga cgcggggat gtcgtcgacg tcgaggacca ggtagttgtg   1860
cttggtgatg gagcgggtga cctcgacgat gggcgtctcc tggaaggcgt cggtgccaat   1920
catgcgtcgc gccacctgtc ccgtgatggc gaccatgggg acggaatcga gcagcgcgtc   1980
ggcgagcgcg gagactaggt tggtggcgcc ggggccggag gtggcgatgc agacgccgac   2040
gcggcccgag gagcgcgcgt agccggaggc ggcaaaggcc tcccccttgct cgtggcggaa   2100
gaggtggttg gcgatgacgg gggagcgggt gagtgcctgg tggatctcca tggacgcgcc   2160
gccggggtag gcgaagacgt cgcggacgcc gcagcgctcg agggactcga cgaggatgtc   2220
agcacccttg cggggctcgg tggggcccca cggccggagc ggggtggccg ggggagccat   2280
cggcatggcg ggtgacgccg ctgagcacct gatgggcgcg gcgagggcgc ggcgggtggc   2340
```

```
caggaggtgc gcccggcgcc tcgccttggg cgcagcggta gtggcgccag tgagcgcggt    2400
agacgcggcg gcggcggtgg ccatggttgc ggcggctgtc tcggaggcgg cgcgagggtt    2460
tggggtgggt gccacggaca cggagtggga gaaaggggga tgtgcgtgga ggcctccctg    2520
cttttgttca gaggatgtgt ggctcagatg gtgatgggaa tgggactcgc aagacgacga    2580
cgacacgtcc gtcgcccgaa tacgtacacg ctacagaccg gacggtgggg cctgtcgacg    2640
tgggaccacg tgtcggcctg gattacaaac agtggtgtcc accgagtgct ggtacacgac    2700
agcgtgcgtc aaggaaggtt ttgaactgtt ccgttaaaaa aagaggggag attttggact    2760
tgactgtgga cgacggtgca tgtcatcgga gtacagacgg tactgacaca aggggcccag    2820
acaagggaat ccaaacgggt cgcacccacc tgccaggctg ccacccgcaa tccgcaacag    2880
ggaaaccggg cacagcccac aaccacaaga tgagcagctg cggcgacagc gtcaggcccg    2940
gtgtcggtgt tagggatggc acccttggc tccccgtatc cgtccccgcg acaaaaaaat    3000
ttcccgcggg gattcccacg aactcttgcg agagacattt cttccccatc cccgttcccc    3060
acggggataa atccccatcg gggatcctct agagtcgacc tgcaggcatg caagcttcgg    3120
tccgcggcca gcttgctaac ccgggccccc cctcgaggtc atcacatcaa tccacttgct    3180
ttgaagacgt ggttggaacg tcttcttttt ccacgatgct cctcgtgggt gggggtccat    3240
ctttgggacc actgtcggca gaggcatctt caacgatggc cttttcctta tcgcaatgat    3300
ggcatttgta ggagccacct tccttttcca ctatcttcac aataaagtga cagatagctg    3360
ggcaatggaa tccgaggagg tttccggata ttacccctttg ttgaaaagtc tcaattgccc    3420
tttggtcttc tgagactgta tctttgatat ttttggagta gacaagcgtg tcgtgctcca    3480
ccatgttgac gaagattttc ttcttgtcat tgagtcgtaa gagactctgt atgaactgtt    3540
cgccagtctt tacggcgagt tctgttaggt cctctatttg aatctttgac tccatggacg    3600
gtatcgataa gctagcttga tatcacatca atccacttgc tttgaagacg tggttggaac    3660
gtcttctttt tccacgatgc tcctcgtggg tgggggtcca tctttgggac cactgtcggc    3720
agaggcatct tcaacgatgg ccttttcctttt atcgcaatga tggcatttgt aggagccacc    3780
ttccttttcc actatcttca aataaagtg acagatagct gggcaatgga atccgaggag    3840
gtttccggat attaccctttt gttgaaaagt ctcaattgcc ctttggtctt ctgagactgt    3900
atctttgata tttttggagt agacaagcgt gtcgtgctcc accatgttga cgaagatttt    3960
cttcttgtca ttgagtcgta agagactctg tatgaactgt tcgccagtct ttacggcgag    4020
ttctgttagg tcctctatttt gaatctttga ctccatgatc gaattatcac atcaatccac    4080
ttgctttgaa gacgtggttg gaacgtcttc tttttccacg atgctcctcg tgggtggggg    4140
tccatctttg ggaccactgt cggcagaggc atcttcaacg atggcctttc ctttatcgca    4200
atgatggcat ttgtaggagc caccttcctt ttccactatc ttcacaataa agtgacagat    4260
agctgggcaa tggaatccga ggaggtttcc ggatattacc ctttgttgaa aagtctcaat    4320
tgccctttgg tcttctgaga ctgtatcttt gatattttttg gagtagacaa gcgtgtcgtg    4380
ctccaccatg ttgacgaaga ttttcttctt gtcattgagt cgtaagagac tctgtatgaa    4440
ctgttcgcca gtctttacgg cgagttctgt taggtcctct atttgaatct tgactccat    4500 gggaattcct gcagcccggg atctaggagc ttgcatgcct gcagtgcagc gtgacccggt    4560 cgtgccctc tctagagata atgagcattg catgtctaag ttataaaaaa ttaccacata    4620 tttttttgt cacacttgtt tgaagtgcag tttatctatc tttatacata tatttaaact    4680
ttactctacg aataatataa tctatagtac tacaataata tcagtgtttt agagaatcat    4740
```

```
ataaatgaac agttagacat ggtctaaagg acaattgagt attttgacaa caggactcta   4800
cagttttatc ttttttagtgt gcatgtgttc tcctttttt ttgcaaatag cttcacctat   4860
ataatacttc atccatttta ttagtacatc catttagggt ttaggttaa tggtttttat    4920
agactaattt ttttagtaca tctattttat tctattttag cctctaaatt aagaaaacta   4980
aaactctatt ttagttttt tatttaataa tttagatata aaatagaata aaataaagtg    5040
actaaaaatt aaacaaatac cctttaagaa attaaaaaaa ctaaggaaac attttcttg    5100
tttcgagtag ataatgccag cctgttaaac gccgtcgacg agtctaacgg acaccaacca   5160
gcgaaccagc agcgtcgcgt cgggccaagc gaagcagacg gcacggcatc tctgtcgctg   5220
cctctggacc cctctcgaga gttccgctcc accgttggac ttgctccgct gtcggcatcc   5280
agaaattgcg tggcggagcg gcagacgtga gccggcacgg caggcggcct cctcctcctc   5340
tcacggcacc ggcagctacg ggggattcct ttcccaccgc tccttcgctt tcccttcctc   5400
gcccgccgta ataaatagac acccctcca caccctcttt cccaacctc gtgttgttcg     5460
gagcgcacac acacacaacc agatctcccc caaatccacc cgtcggcacc tccgcttcaa   5520
ggtacgccgc tcgtcctccc cccccccct ctctaccttc tctagatcgg cgttccggtc    5580
catggttagg gcccggtagt tctacttctg ttcatgtttg tgttagatcc gtgtttgtgt   5640
tagatccgtc ctgctagcgt tcgtacacgg atgcgacctg tacgtcagac acgttctgat   5700
tgctaacttg ccagtgtttc tctttgggga atcctgggat ggctctagcc gttccgcaga   5760
cgggatcgat ttcatgattt ttttttgttc gttgcatagg gttggtttg ccctttttcct   5820
ttatttcaat atatgccgtg cacttgtttg tcgggtcatc ttttcatgct ttttttgtc    5880
ttggttgtga tgatgtggtc tggttgggcg gtcgttctag atcggagtag aattctgttt   5940
caaactacct ggtggattta ttaattttgg atctgtatgt gtgtgccata catattcata   6000
gttacgaatt gaagatgatg gatggaaata tcgatctagg ataggtatac atgttgatgc   6060
gggttttact gatgcatata cagagatgct ttttgttcgc ttggttgtga tgatgtggtg   6120
tggttgggcg gtcgttcatt cgttctagat cggagtagaa tactgtttca aactacctgg   6180
tgtatttatt aattttggaa ctgtatgtgt gtgtcataca tcttcatagt tacgagttta   6240
agatggatgg aaatatcgat ctaggatagg tatacatgtt gatgtgggtt ttactgatgc   6300
atatacatga tggcatatgc agcatctatt catatgctct aaccttgagt acctatctat   6360
tataataaac aagtatgttt tataattatt ttgatcttga tatacttgga tgatggcata   6420
tgcagcagct atatgtggat ttttttagcc ctgccttcat acgctattta tttgcttggt   6480
actgtttctt ttgtcgatgc tcaccctgtt gtttggtgtt acttctgcag gtcgaccgcc   6540
ggggatccac acgacaccat ggctattgag gttaagccta tcaacgcaga ggatacctat   6600
gaccttaggc atagagtgct cagaccaaac cagcctatcg aagcctgcat gtttgagtct   6660
gaccttacta ggagtgcatt tcaccttggt ggattctacg gaggtaaact gatttccgtg   6720
gcttcattcc accaagctga gcactctgaa cttcaaggta agaagcagta ccagcttaga   6780
ggtgtggcta ccttggaagg ttatagagag cagaaggctg gttccagtct cgtgaaacac   6840
gctgaagaga ttctcagaaa gagaggtgct gacatgatct ggtgtaatgc caggacatct   6900
gcttcaggat actacaggaa gttgggattc agtgagcaag gagaggtgtt cgatactcct   6960
ccagttggac ctcacatcct gatgtataag aggatcacat aactagctag tcagttaacc   7020
tagacttgtc catcttctgg attggccaac ttaattaatg tatgaaataa aaggatgcac   7080
acatagtgac atgctaatca ctataatgtg ggcatcaaag ttgtgtgtta tgtgtaatta   7140
```

```
ctagttatct gaataaaaga gaaagagatc atccatattt cttatcctaa atgaatgtca    7200
cgtgtcttta taattctttg atgaaccaga tgcatttcat taaccaaatc catatacata    7260
taaatattaa tcatatataa ttaatatcaa ttgggttagc aaaacaaatc tagtctaggt    7320
gtgttttgcg aattcagtac attaaaaacg tccgcaatgt gttattaagt tgtctaagcg    7380
tcaatttg                                                              7388

<210> SEQ ID NO 4
<211> LENGTH: 9425
<212> TYPE: DNA
<213> ORGANISM: Artificial Sequence
<220> FEATURE:
<223> OTHER INFORMATION: Right and left junction borders and internal
      transgene in maize event DP-098140-6
<220> FEATURE:
<221> NAME/KEY: misc_feature
<222> LOCATION: 9377, 9378, 9379, 9380, 9381, 9382
<223> OTHER INFORMATION: n = A,T,C or G
<220> FEATURE:
<221> NAME/KEY: misc_feature
<222> LOCATION: 9377, 9378, 9379, 9380, 9381, 9382
<223> OTHER INFORMATION: n = A,T,C or G

<400> SEQUENCE: 4
atgaaaaagt ccaagtcgag caagggtacg taccgcggcc ggcggctaat tacggaggac      60
atgtcgtagt agctggtagt aaattaacac acgcgtacga gtagcggagt taaatggggg     120
catgcatgca gcaggacgtg gtattagtaa gcttactact ctagctttat ccatccatcc     180
atcgcgctag ctggctgcag gcacgggtta tcttatcttg tcgtccagag gacgacacac     240
ggccggccgg tgaagtaaaa gggagtaatc ttattttgcc aggacgaggg gcggtacatg     300
atattacaca cgtaccatgc atgcatatat gcatggacaa ggtacgtcgt cgtcgatcga     360
cgtcgatgca tatgtgtgta tgtatgtacg tgcataatgc atggtaccag ctgctggctt     420
atatatattt gtcaccgatc gatgcatgct gctgctctac acggtttgac actttaattt     480
gactcatcga tgaccttgct agatagtagc ggctcgtcaa ttaatgagcc atcaagttaa     540
caagagggca cgggcttgcg cgactgattc caccttatta acatacgccc tgcgcccgcg     600
cgtgctgtac gtacgagaat ttcgaattac attaattcaa agctgtgtat gtatgtatat     660
atatatgtgc gttttttttgt gtgtgtatgt ctctttgctt ggtctttctc tatcgatccc     720
cctctttgat agtttaaact gaaggcggga acgacaatc tgatcatgag cggagaatta     780
agggagtcac gttatgaccc ccgccgatga cgcgggacaa gccgttttac gtttggaact     840
gacagaaccg caacgttgaa ggagccactc agcaagctgg gcccccctc gaggtcggcc     900 gcattcgcaa aacacaccta gactagattt gttttgctaa cccaattgat attaattata     960
tatgattaat atttatatgt atatggattt ggttaatgaa atgcatctgg ttcatcaaag    1020
aattataaag acacgtgaca ttcatttagg ataagaaata tggatgatct ctttctcttt    1080
tattcagata actagtaatt acacataaca cacaactttg atgcccacat tatagtgatt    1140
agcatgtcac tatgtgtgca tccttttatt tcatacatta attaagttgg ccaatccaga    1200
agatggacaa gtctaggtta actgactagc tagtcagtac acagtcctgc catcaccatc    1260
caggatcata tccttgaaag ccccaccact agggatcata gcaacacat gctcctggtg    1320 tgggacgatt atatccaaga ggtacggccc tggagtctcg agcatcttct ttatcgctgc    1380
gcggacttcg ttcttctttg tcacacggac cgctggaatg ttgaacccct tggcgatcgt    1440
cacgaaatct ggatatatct cactttcatt ctctgggttt cccaagtatg tgtgcgctct    1500
```

```
gttggcctta tagaacctgt cctccaactg caccaccatc cccaggtgct ggttgtttag      1560
cacaaagacc ttcaccggga ggttctcaat tcggatcata gctagctcct gaacgttcat      1620
gagaaagcta ccatctccat cgatgtcaac aacagtgaca cctgggttgg ccacagaagc      1680
accagcagca gccggcaaac caaatcccat agccccaaga ccagctgaag acaaccactg      1740
ccttggccgc ttgtaagtgt agtactgtgc cgcccacatc tggtgctgcc caacacctgt      1800
gccgatgatg gcctcgcctt tcgtcagctc atcaagaacc tgaatagcat attgtggctg      1860
gatctcctca ttagatgttt tatacccaag ggggaattcc ctcttctgct gatccaactc      1920
atcgttccat gagccaaagt caaagctctt ctttgatgtg cttccttcaa gaagagcatt      1980
catgccctgc aaagcaagct taacatctgc acagatggac acatgtggct gcttgttctt      2040
gccaatctca gccggatcaa tatcaacgtg cacaatctta gccctgcttg caaaagcctc      2100
aatcttccct gtcacgcgat catcaaaccg cacaccaagt gcaagcaaca gatcggcctt      2160
atccactgca taatttgcat acaccgtccc atgcatacct agcatgcgca gagacagtgg      2220
gtcgtcgctg gggaagttgc cgaggcccat aagagtagtt gtgaccggga ttccagtcag      2280
ctccacaaag cgtcgcaact cctcaccaga tgctgcgcag ccaccgccca cataaagaac      2340
agggcgccgc gattcaccaa caagacgcag cacctgctca gcaactcag tcgcaggggg       2400 cttgggaagg cgcgcaatgt acccaggcag actcatgggc ttgtcccaga caggcaccgc      2460
catctgctgc tggatgtcct tggggatgtc gacaagcacc ggccctggtc gaccagagga      2520
ggcgaggaag aaagcctcct gcacgacgcg ggggatgtcg tcgacgtcga ggaccaggta      2580
gttgtgcttg gtgatggagc gggtgacctc gacgatgggc gtctcctgga aggcgtcggt      2640
gccaatcatg cgtcgcgcca cctgtcccgt gatggcgacc atggggacgg aatcgagcag      2700
cgcgtcggcg agcgcggaga ctaggttggt ggcgccgggg ccgaggtgg cgatgcagac       2760 gccgacgcgg cccgaggagc gcgcgtagcc ggaggcggca aaggcctccc cttgctcgtg      2820
gcggaagagg tggttggcga tgacggggga gcggtgagt gcctggtgga tctccatgga       2880
cgcgccgccg gggtaggcga agacgtcgcg gacgccgcag cgctcgaggg actcgacgag      2940
gatgtcagca cccttgcggg gctcggtggg gccccacggc cggagcgggg tggccggggg      3000
agccatcggc atggcgggtg acgccgctga gcacctgatg ggcgcggcga gggcgcggcg      3060
ggtggccagg aggtgcgccc ggcgcctcgc cttgggcgca gcgtagtgg cgccagtgag       3120 cgcggtagac gcggcggcgg cggtggccat ggttgcggcg gctgtctcgg aggcggcgcg      3180
agggtttggg gtgggtgcca cggacacgga gtggagaaa gggggatgtg cgtgaggcc       3240 tccctgcttt tgttcagagg atgtgtggct cagatggtga tgggaatggg actcgcaaga      3300
cgacgacgac acgtccgtcg cccgaatacg tacacgctac agaccggacg gtggggcctg      3360
tcgacgtggg accacgtgtc ggcctggatt acaaacagtg gtgtccaccg agtgctggta      3420
cacgacagcg tgcgtcaagg aaggttttga actgttccgt taaaaaaga ggggagattt       3480 tggacttgac tgtggacgac ggtgcatgtc atcggagtac agacggtact gacacaaggg      3540
gcccagacaa gggaatccaa acgggtcgca cccacctgcc aggctgccac cgcaatccg       3600 caacagggaa accgggcaca gcccacaacc acaagatgag cagctgcggc gacagcgtca      3660
ggcccggtgt cggtgttagg gatggcaccc tttggctccc cgtatccgtc cccgcgacaa      3720
aaaaatttcc cgcggggatt cccacgaact cttgcgagag acatttcttc cccatccccg      3780
ttccccacgg ggataaatcc ccatcgggga tcctctagag tcgacctgca ggcatgcaag      3840
cttcggtccg cggccagctt gctaacccgg gccccccctc gaggtcatca catcaatcca      3900
```

```
cttgctttga agacgtggtt ggaacgtctt cttttccac gatgctcctc gtgggtgggg      3960
gtccatcttt gggaccactg tcggcagagg catcttcaac gatggccttt cctttatcgc      4020
aatgatggca tttgtaggag ccaccttcct tttccactat cttcacaata aagtgacaga      4080
tagctgggca atggaatccg aggaggtttc cggatattac cctttgttga aaagtctcaa      4140
ttgcccttttg gtcttctgag actgtatctt tgatatttt ggagtagaca agcgtgtcgt      4200
gctccaccat gttgacgaag attttcttct tgtcattgag tcgtaagaga ctctgtatga      4260
actgttcgcc agtctttacg gcgagttctg ttaggtcctc tatttgaatc tttgactcca      4320
tggacggtat cgataagcta gcttgatatc acatcaatcc acttgctttg aagacgtggt      4380
tggaacgtct tctttttcca cgatgctcct cgtgggtggg ggtccatctt tgggaccact      4440
gtcggcagag gcatcttcaa cgatggcctt tcctttatcg caatgatggc atttgtagga      4500
gccaccttcc ttttccacta tcttcacaat aaagtgacag atagctgggc aatggaatcc      4560
gaggaggttt ccggatatta ccctttgttg aaaagtctca attgcccttt ggtcttctga      4620
gactgtatct ttgatatttt tggagtagac aagcgtgtcg tgctccacca tgttgacgaa      4680
gattttcttc ttgtcattga gtcgtaagag actctgtatg aactgttcgc cagtctttac      4740
ggcgagttct gttaggtcct ctatttgaat ctttgactcc atgatcgaat tatcacatca      4800
atccacttgc tttgaagacg tggttggaac gtcttctttt tccacgatgc tcctcgtggg      4860
tgggggtcca tctttgggac cactgtcggc agaggcatct tcaacgatgg cctttccttt      4920
atcgcaatga tggcatttgt aggagccacc ttccttttcc actatcttca caataaagtg      4980
acagatagct gggcaatgga atccgaggag gtttccggat attaccctttt gttgaaaagt      5040
ctcaattgcc ctttggtctt ctgagactgt atctttgata ttttttggagt agacaagcgt      5100
gtcgtgctcc accatgttga cgaagatttt cttcttgtca ttgagtcgta agagactctg      5160
tatgaactgt tcgccagtct ttacggcgag ttctgttagg tcctctattt gaatctttga      5220
ctccatggga attcctgcag cccgggatct aggagcttgc atgcctgcag tgcagcgtga      5280
cccggtcgtg cccctctcta gagataatga gcattgcatg tctaagttat aaaaaattac      5340
cacatatttt ttttgtcaca cttgtttgaa gtgcagttta tctatcttta tacatatatt      5400
taaactttac tctacgaata atataatcta tagtactaca ataatatcag tgttttagag      5460
aatcatataa atgaacagtt agacatggtc taaaggacaa ttgagtattt tgacaacagg      5520
actctacagt tttatctttt tagtgtgcat gtgttctcct tttttttgc aaatagcttc      5580
acctatataa tacttcatcc attttattag tacatccatt tagggtttag ggttaatggt      5640
ttttatagac taattttttt agtacatcta ttttattcta ttttagcctc taaattaaga      5700
aaactaaaac tctattttag tttttttatt taataattta gatataaaat agaataaaat      5760
aaagtgacta aaaattaaac aaatacccctt taagaaatta aaaaaactaa ggaaacattt      5820
ttcttgtttc gagtagataa tgccagcctg ttaaacgccg tcgacgagtc taacggacac      5880
caaccagcga accagcagcg tcgcgtcggg ccaagcgaag cagacggcac ggcatctctg      5940
tcgctgcctc tggaccccctc tcgagagttc cgctccaccg ttggacttgc tccgctgtcg      6000
gcatccagaa attgcgtggc ggagcggcag acgtgagccg gcacggcagg cggcctcctc      6060
ctcctctcac ggcaccggca gctacggggg attccttttcc caccgctcct tcgctttccc      6120
ttcctcgccc gccgtaataa atagacaccc cctccacacc ctcttttcccc aacctcgtgt      6180
tgttcggagc gcacacacac acaaccgat ctccccccaaa tccacccgtc ggcacctccg      6240
cttcaaggta cgccgctcgt cctcccccccc cccctctct accttctcta gatcggcgtt      6300
```

```
ccggtccatg gttagggccc ggtagttcta cttctgttca tgtttgtgtt agatccgtgt    6360
ttgtgttaga tccgtgctgc tagcgttcgt acacggatgc gacctgtacg tcagacacgt    6420
tctgattgct aacttgccag tgtttctctt tggggaatcc tgggatggct ctagccgttc    6480
cgcagacggg atcgatttca tgattttttt tgtttcgttg catagggttt ggtttgccct    6540
tttcctttat ttcaatatat gccgtgcact tgtttgtcgg gtcatctttt catgcttttt    6600
tttgtcttgg ttgtgatgat gtggtctggt tgggcggtcg ttctagatcg gagtagaatt    6660
ctgtttcaaa ctacctggtg gatttattaa ttttggatct gtatgtgtgt gccatacata    6720
ttcatagtta cgaattgaag atgatggatg gaaatatcga tctaggatag gtatacatgt    6780
tgatgcgggt tttactgatg catatacaga gatgcttttt gttcgcttgg ttgtgatgat    6840
gtggtgtggt tgggcggtcg ttcattcgtt ctagatcgga gtagaatact gtttcaaact    6900
acctggtgta tttattaatt ttggaactgt atgtgtgtgt catacatctt catagttacg    6960
agtttaagat ggatggaaat atcgatctag gataggtata catgttgatg tgggttttac    7020
tgatgcatat acatgatggc atatgcagca tctattcata tgctctaacc ttgagtacct    7080
atctattata ataaacaagt atgttttata attattttga tcttgatata cttggatgat    7140
ggcatatgca gcagctatat gtggattttt ttagccctgc cttcatacgc tatttatttg    7200
cttggtactg tttcttttgt cgatgctcac cctgttgttt ggtgttactt ctgcaggtcg    7260
accgccgggg atccacacga caccatggct attgaggtta agcctatcaa cgcagaggat    7320
acctatgacc ttaggcatag agtgctcaga ccaaaccagc ctatcgaagc ctgcatgttt    7380
gagtctgacc ttactaggag tgcatttcac cttggtggat tctacggagg taaactgatt    7440
tccgtggctt cattccacca agctgagcac tctgaacttc aaggtaagaa gcagtaccag    7500
cttagaggtg tggctacctt ggaaggttat agagagcaga aggctggttc cagtctcgtg    7560
aaacacgctg aagagattct cagaaagaga ggtgctgaca tgatctggtg taatgccagg    7620
acatctgctt caggatacta caggaagttg ggattcagtg agcaaggaga ggtgttcgat    7680
actcctccag ttggaccctca catcctgatg tataagagga tcacataact agctagtcag    7740
ttaacctaga cttgtccatc ttctggattg gccaacttaa ttaatgtatg aaataaaagg    7800
atgcacacat agtgacatgc taatcactat aatgtgggca tcaaagttgt gtgttatgtg    7860
taattactag ttatctgaat aaaagagaaa gagatcatcc atatttctta tcctaaatga    7920
atgtcacgtg tctttataat tctttgatga accagatgca tttcattaac caaatccata    7980
tacatataaa tattaatcat atataattaa tatcaattgg gttagcaaaa caaatctagt    8040
ctaggtgtgt tttgcgaatt cagtacatta aaaacgtccg caatgtgtta ttaagttgtc    8100
taagcgtcaa tttgctgtac atgtaaccag ctttcctaga aaaaaacac agtaatattt    8160 acagtataca ataatgctca ttgattagat ccaaaattat gaaatgtata tatttttgc    8220 cataactttt attacagtct tatactgaag taaagttgta tcacgtcatg aacatagaat    8280
aagactgaga tagttgacta atccagtcat atcctatagt acactagtaa ggtgcatgtg    8340
ctaacaatat gacaaatcta gtatttcttt atagtttatc atccataaat cgcaaaatac    8400
ctaagcataa ttttatttga atagagagag tactgcccgt tattgtatga ggtaatgact    8460
tccatatata caacatagtc ataagaacac aattatgaaa aaaatctatt taaaattgaa    8520
atgcgttgag atcttgtctt gcatactaaa catagtaaat ataaattaat gcataaatga    8580
ctgttataac agacaatgct ggtgacaata gacaatgtac tgaatctaac tggatacgta    8640
ggatgctgct atcttattca ctcatagtta ttcagatagt ggtcattctt tttgacccat    8700
```

-continued

```
agaaaactgt gtgctataat acaccaaaag gaaagcaaag tgaaaaggaa actttgaata    8760
gccaagaaga ctcggagtgc ttcacgcctt cacctatccc acataggtga tgagctaaga    8820
gtaaaatgta gattctctcg agtactgaat attgcctgca cttttccttg cagtaaatac    8880
acctttaatc catgacgaga gtccactctt tgagtccgtc ttgagattct tccattgatc    8940
atacaacatg acctcgaagt cctgatggag aacaacttat ataattaaaa ctacaataca    9000
gaaagttcct gacaattaaa acctttggtg gtggcatgcc gtaggttaaa aaaaatagat    9060
aatgacaaca caactggaga cacgctcttt gccgagtgct cacacgtttg ctgagagcga    9120
gcactcggca aatatatgat ttgccgaata ccaccctcct cggcaaaaca atacactagg    9180
caaaaaggta gtttcccatc accatgatgc ccgccgttaa tgtaccttct atgccgagta    9240
tgttggcgct cagcaaagag atcgttaccg gcgtttgttt caccaagagc tctttgacga    9300
gtgtggcaca cgacaaaacc ttttgccgag tgtaattagt cgtttgccaa gtgactggtg    9360
cagttggcaa aggagtnnnn nnttatgtgt gggcaaaatg atatatggtg ccagttaggg    9420
ctagc    9425
```

```
<210> SEQ ID NO 5
<211> LENGTH: 20
<212> TYPE: DNA
<213> ORGANISM: Artificial Sequence
<220> FEATURE:
<223> OTHER INFORMATION: right genomic border (10 nt)/ internal
      transgene (10 nt) in maize event DP-098140-6

<400> SEQUENCE: 5 tcccctctt tgatagttta                                                  20

<210> SEQ ID NO 6
<211> LENGTH: 20
<212> TYPE: DNA
<213> ORGANISM: Artificial Sequence
<220> FEATURE:
<223> OTHER INFORMATION: left genomic border (10 nt)/ internal transgene
      (10 nt) in maize event DP-098140-6

<400> SEQUENCE: 6
cgtcaatttg ctgtacatgt                                                 20

<210> SEQ ID NO 7
<211> LENGTH: 40
<212> TYPE: DNA
<213> ORGANISM: Artificial Sequence
<220> FEATURE:
<223> OTHER INFORMATION: right genomic border (20 nt)/ internal
      transgene (20 nt) in maize event DP-098140-6

<400> SEQUENCE: 7
tctctatcga tcccctctt tgatagttta aactgaaggc                            40

<210> SEQ ID NO 8
<211> LENGTH: 40
<212> TYPE: DNA
<213> ORGANISM: Artificial Sequence
<220> FEATURE:
<223> OTHER INFORMATION: left genomic border (20 nt)/ internal transgene
      (20 nt) in maize event DP-098140-6

<400> SEQUENCE: 8
gttgtctaag cgtcaatttg ctgtacatgt aaccagcttt                           40

<210> SEQ ID NO 9
```

-continued

```
<211> LENGTH: 60
<212> TYPE: DNA
<213> ORGANISM: Artificial Sequence
<220> FEATURE:
<223> OTHER INFORMATION: right genomic border (30 nt)/ internal
      transgene (30 nt) in maize event DP-098140-6

<400> SEQUENCE: 9
gcttggtctt tctctatcga tccccctctt tgatagttta aactgaaggc gggaaacgac    60

<210> SEQ ID NO 10
<211> LENGTH: 60
<212> TYPE: DNA
<213> ORGANISM: Artificial Sequence
<220> FEATURE:
<223> OTHER INFORMATION: left genomic border (30 nt)/ internal transgene
      (30 nt) in maize event DP-098140-6

<400> SEQUENCE: 10
gtgttattaa gttgtctaag cgtcaatttg ctgtacatgt aaccagctttt cctagaaaaa   60

<210> SEQ ID NO 11
<211> LENGTH: 8699
<212> TYPE: DNA
<213> ORGANISM: Artificial Sequence
<220> FEATURE:
<223> OTHER INFORMATION: left genomic border and complete internal
      transgene in maize event DP-098140-6
<220> FEATURE:
<221> NAME/KEY: misc_feature
<222> LOCATION: 8651, 8652, 8653, 8654, 8655, 8656
<223> OTHER INFORMATION: n = A,T,C or G
<220> FEATURE:
<221> NAME/KEY: misc_feature
<222> LOCATION: 8651, 8652, 8653, 8654, 8655, 8656
<223> OTHER INFORMATION: n = A,T,C or G

<400> SEQUENCE: 11
tgatagttta aactgaaggc gggaaacgac aatctgatca tgagcggaga attaagggag     60
tcacgttatg accccccgccg atgacgcggg acaagccgtt ttacgtttgg aactgacaga   120
accgcaacgt tgaaggagcc actcagcaag ctgggccccc cctcgaggtc ggccgcattc   180
gcaaaacaca cctagactag atttgttttg ctaacccaat tgatattaat tatatatgat   240 taatattttat atgtatatgg attttggttaa tgaaatgcat ctggttcatc aaagaattat   300
aaagacacgt gacattcatt taggataaga aatatggatg atctctttct cttttattca   360
gataactagt aattacacat aacacacaac tttgatgccc acattatagt gattagcatg   420
tcactatgtg tgcatccttt tatttcatac attaattaag ttggccaatc cagaagatgg   480
acaagtctag gttaactgac tagctagtca gtacacagtc ctgccatcac catccaggat   540
catatccttg aaagccccac cactagggat cataggcaac acatgctcct ggtgtgggac   600
gattatatcc aagaggtacg gccctggagt ctcgagcatc ttctttatcg ctgcgcggac   660
ttcgttcttc tttgtcacac ggaccgctgg aatgttgaac cctttggcga tcgtcacgaa   720
atctggatat atctcacttt cattctctgg gtttcccaag tatgtgtgcg ctctgttggc   780
cttatagaac ctgtcctcca actgcaccac catcccagg tgctggttgt ttagcacaaa    840
gaccttcacc gggaggttct caattcggat catagctagc tcctgaacgt tcatgagaaa   900
gctaccatct ccatcgatgt caacaacagt gacacctggg ttggcacag aagcaccagc    960 agcagccggc aaaccaaatc ccatagcccc aagaccagct gaagacaacc actgccttgg  1020
ccgcttgtaa gtgtagtact gtgccgccca catctggtgc tgcccaacac ctgtgccgat  1080
gatggcctcg cctttcgtca gctcatcaag aacctgaata gcatattgtg gctggatctc  1140
```

```
ctcattagat gttttatacc caagggggaa ttccctcttc tgctgatcca actcatcgtt    1200
ccatgagcca aagtcaaagc tcttctttga tgtgcttcct tcaagaagag cattcatgcc    1260
ctgcaaagca agcttaacat ctgcacagat ggacacatgt ggctgcttgt tcttgccaat    1320
ctcagccgga tcaatatcaa cgtgcacaat cttagccctg cttgcaaaag cctcaatctt    1380
ccctgtcacg cgatcatcaa accgcacacc aagtgcaagc aacagatcgg ccttatccac    1440
tgcataattt gcatacaccg tcccatgcat acctagcatg cgcagagaca gtgggtcgtc    1500
gctggggaag ttgccgaggc ccataagagt agttgtgacc gggattccag tcagctccac    1560
aaagcgtcgc aactcctcac cagatgctgc gcagccaccg cccacataaa gaacagggcg    1620
ccgcgattca ccaacaagac gcagcacctg ctcaagcaac tcagtcgcag ggggcttggg    1680
aaggcgcgca atgtacccag gcagactcat gggcttgtcc cagacaggca ccgccatctg    1740
ctgctggatg tccttgggga tgtcgacaag caccggccct ggtcgaccag aggaggcgag    1800
gaagaaagcc tcctgcacga cgcggggat gtcgtcgacg tcgaggacca ggtagttgtg    1860
cttggtgatg gagcgggtga cctcgacgat gggcgtctcc tggaaggcgt cggtgccaat    1920
catgcgtcgc gccacctgtc ccgtgatggc gaccatgggg acggaatcga gcagcgcgtc    1980
ggcgagcgcg gagactaggt tggtggcgcc ggggccggag gtggcgatgc agacgccgac    2040
gcggcccgag gagcgcgcgt agccggaggc ggcaaaggcc tcccttgct cgtggcggaa    2100 gaggtggttg gcgatgacgg gggagcgggt gagtgcctgg tggatctcca tggacgcgcc    2160
gccggggtag gcgaagacgt cgcggacgcc gcagcgctcg agggactcga cgaggatgtc    2220
agcacccttg cggggctcgg tggggcccca cggccggagc ggggtggccg ggggagccat    2280
cggcatggcg ggtgacgccg ctgagcacct gatgggcgcg gcgagggcgc ggcgggtggc    2340
caggaggtgc gcccggcgcc tcgccttggg cgcagcggta gtggcgccag tgagcgcggt    2400
agacgcggcg gcggcggtgg ccatggttgc ggcggctgtc tcggaggcgg cgcgagggtt    2460
tggggtgggt gccacggaca cggagtggga gaaaggggga tgtgcgtgga ggcctccctg    2520
cttttgttca gaggatgtgt ggctcagatg gtgatgggaa tgggactcgc aagacgacga    2580
cgacacgtcc gtcgcccgaa tacgtacacg ctacagaccg gacggtgggg cctgtcgacg    2640
tgggaccacg tgtcggcctg gattacaaac agtggtgtcc accgagtgct ggtacacgac    2700
agcgtgcgtc aaggaaggtt ttgaactgtt ccgttaaaaa aagagggag attttggact    2760 tgactgtgga cgacggtgca tgtcatcgga gtacagacgg tactgacaca aggggcccag    2820
acaagggaat ccaaacgggt cgcacccacc tgccaggctg ccacccgcaa tccgcaacag    2880
ggaaaccggg cacagcccac aaccacaaga tgagcagctg cggcgacagc gtcaggcccg    2940
gtgtcggtgt tagggatggc acccttggc tccccgtatc cgtcccgcg acaaaaaaat    3000 ttcccgcggg gattcccacg aactcttgcg agagacattt cttccccatc cccgttcccc    3060
acggggataa atccccatcg gggatcctct agagtcgacc tgcaggcatg caagcttcgg    3120
tccgcggcca gcttgctaac ccgggccccc cctcgaggtc atcacatcaa tccacttgct    3180
ttgaagacgt ggttggaacg tcttctttt ccacgatgct cctcgtgggt gggggtccat    3240
ctttgggacc actgtcggca gaggcatctt caacgatggc ctttccttta tcgcaatgat    3300
ggcatttgta ggagccacct tccttttcca ctatcttcac aataaagtga cagatagctg    3360
ggcaatggaa tccgaggagg tttccggata ttacccttg ttgaaaagtc tcaattgccc    3420
tttggtcttc tgagactgta tctttgatat ttttggagta gacaagcgtg tcgtgctcca    3480
ccatgttgac gaagatttc ttcttgtcat tgagtcgtaa gagactctgt atgaactgtt    3540
```

```
cgccagtctt tacggcgagt tctgttaggt cctctatttg aatctttgac tccatggacg   3600
gtatcgataa gctagcttga tatcacatca atccacttgc tttgaagacg tggttggaac   3660
gtcttctttt tccacgatgc tcctcgtggg tggggtcca tctttgggac cactgtcggc    3720
agaggcatct tcaacgatgg cctttccttt atcgcaatga tggcatttgt aggagccacc   3780
ttccttttcc actatcttca caataaagtg acagatagct gggcaatgga atccgaggag   3840
gtttccggat attacccttt gttgaaaagt ctcaattgcc ctttggtctt ctgagactgt   3900
atctttgata tttttggagt agacaagcgt gtcgtgctcc accatgttga cgaagatttt   3960
cttcttgtca ttgagtcgta agagactctg tatgaactgt tcgccagtct tacggcgag   4020 ttctgttagg tcctctattt gaatctttga ctccatgatc gaattatcac atcaatccac   4080
ttgctttgaa gacgtggttg aacgtcttc ttttccacg atgctcctcg tgggtggggg    4140
tccatctttg gaccactgt cggcagaggc atcttcaacg atggcctttc ctttatcgca   4200
atgatggcat ttgtaggagc caccttcctt ttccactatc ttcacaataa agtgacagat   4260
agctgggcaa tggaatccga ggaggtttcc ggatattacc ctttgttgaa aagtctcaat   4320
tgccctttgg tcttctgaga ctgtatcttt gatattttg gagtagacaa gcgtgtcgtg    4380
ctccaccatg ttgacgaaga ttttcttctt gtcattgagt cgtaagagac tctgtatgaa   4440
ctgttcgcca gtctttacgg cgagttctgt taggtcctct atttgaatct ttgactccat   4500
gggaattcct gcagcccggg atctaggagc ttgcatgcct gcagtgcagc gtgacccggt   4560
cgtgcccctc tctagagata tgagcattg catgtctaag ttataaaaaa ttaccacata    4620
ttttttttgt cacacttgtt tgaagtgcag tttatctatc tttatacata tatttaaact   4680
ttactctacg aataatataa tctatagtac tacaataata tcagtgtttt agagaatcat   4740
ataaatgaac agttagacat ggtctaaagg acaattgagt attttgacaa caggactcta   4800 cagtttatc ttttagtgt gcatgtgttc tcctttttt ttgcaaatag cttcacctat     4860
ataatacttc atccatttta ttagtacatc catttagggt ttagggttaa tggtttttat   4920
agactaattt ttttagtaca tctattttat tctattttag cctctaaatt aagaaaacta   4980
aaactctatt ttagtttttt tatttaataa tttagatata aaatagaata aaataaagtg   5040
actaaaaatt aaacaaatac cctttaagaa attaaaaaaa ctaaggaaac atttttcttg   5100
tttcgagtag ataatgccag cctgttaaac gccgtcgacg agtctaacgg acaccaacca   5160
gcgaaccagc agcgtcgcgt cgggccaagc gaagcagacg gcacggcatc tctgtcgctg   5220
cctctggacc cctctcgaga gttccgctcc accgttggac ttgctccgct gtcggcatcc   5280
agaaattgcg tggcggagcg gcagacgtga gccggcacgg caggcggcct cctcctcctc   5340
tcacggcacc ggcagctacg ggggattcct ttcccaccgc tccttcgctt tcccttcctc   5400
gcccgccgta ataaatagac accccctcca caccctcttt ccccaacctc gtgttgttcg   5460
gagcgcacac acacacaacc agatctcccc caaatccacc cgtcggcacc tccgcttcaa   5520
ggtacgccgc tcgtcctccc cccccccct ctctacctcc tctagatcgg cgttccggtc   5580
catggttagg gcccggtagt tctacttctg ttcatgtttg tgttagatcc gtgtttgtgt   5640
tagatccgtg ctgctagcgt tcgtacacgg atgcgacctg tacgtcagac acgttctgat   5700
tgctaacttg ccagtgtttc tctttgggga atcctgggat ggctctagcc gttccgcaga   5760
cgggatcgat ttcatgattt ttttgtttc gttgcatagg gtttggtttg ccctttttcct  5820 ttatttcaat atatgccgtg cacttgtttg tcgggtcatc ttttcatgct ttttttttgtc  5880 ttggttgtga tgatgtggtc tggttgggcg gtcgttctag atcggagtag aattctgttt   5940
```

```
caaactacct ggtggattta ttaattttgg atctgtatgt gtgtgccata catattcata    6000
gttacgaatt gaagatgatg gatggaaata tcgatctagg ataggtatac atgttgatgc    6060
gggttttact gatgcatata cagagatgct ttttgttcgc ttggttgtga tgatgtggtg    6120
tggttgggcg gtcgttcatt cgttctagat cggagtagaa tactgtttca aactacctgg    6180
tgtatttatt aattttggaa ctgtatgtgt gtgtcataca tcttcatagt tacgagttta    6240
agatggatgg aaatatcgat ctaggatagg tatacatgtt gatgtgggtt ttactgatgc    6300
atatacatga tggcatatgc agcatctatt catatgctct aaccttgagt acctatctat    6360
tataataaac aagtatgttt tataattatt ttgatcttga tatacttgga tgatggcata    6420
tgcagcagct atatgtggat tttttttagcc ctgccttcat acgctattta tttgcttggt    6480
actgtttctt ttgtcgatgc tcaccctgtt gtttggtgtt acttctgcag gtcgaccgcc    6540
ggggatccac acgacaccat ggctattgag gttaagccta tcaacgcaga ggatacctat    6600
gaccttaggc atagagtgct cagaccaaac cagcctatcg aagcctgcat gtttgagtct    6660
gaccttacta ggagtgcatt tcaccttggt ggattctacg gaggtaaact gatttccgtg    6720
gcttcattcc accaagctga gcactctgaa cttcaaggta agaagcagta ccagcttaga    6780
ggtgtggcta ccttggaagg ttatagagag cagaaggctg gttccagtct cgtgaaacac    6840
gctgaagaga ttctcagaaa gagaggtgct gacatgatct ggtgtaatgc caggacatct    6900
gcttcaggat actacaggaa gttgggattc agtgagcaag gagaggtgtt cgatactcct    6960
ccagttggac ctcacatcct gatgtataag aggatcacat aactagctag tcagttaacc    7020
tagacttgtc catcttctgg attggccaac ttaattaatg tatgaaataa aaggatgcac    7080
acatagtgac atgctaatca ctataatgtg ggcatcaaag ttgtgtgtta tgtgtaatta    7140
ctagttatct gaataaaaga gaaagagatc atccatattt cttatcctaa atgaatgtca    7200
cgtgtcttta taattctttg atgaaccaga tgcatttcat taaccaaatc catatacata    7260
taaatattaa tcatatataa ttaatatcaa ttgggttagc aaaacaaatc tagtctaggt    7320
gtgttttgcg aattcagtac attaaaaacg tccgcaatgt gttattaagt tgtctaagcg    7380
tcaatttgct gtacatgtaa ccagctttcc tagaaaaaaa acacagtaat atttacagta    7440
tacaataatg ctcattgatt agatccaaaa ttatgaaatg tatatatttt ttgccataac    7500
ttttattaca gtcttatact gaagtaaagt tgtatcacgt catgaacata gaataagact    7560
gagatagttg actaatccag tcatatccta tagtacacta gtaaggtgca tgtgctaaca    7620
atatgacaaa tctagtattt ctttatagtt tatcatccat aaatcgcaaa ataccaagc    7680 ataattttat ttgaatagag agagtactgc ccgttattgt atgaggtaat gacttccata    7740
tatacaacat agtcataaga acacaattat gaaaaaaatc tatttaaaat tgaaatgcgt    7800
tgagatcttg tcttgcatac taaacatagt aaatataaat taatgcataa atgactgtta    7860
taacagacaa tgctggtgac aatagacaat gtactgaatc taactggata cgtaggatgc    7920
tgctatctta ttcactcata gttattcaga tagtggtcat tcttttttgac ccatagaaaa    7980 ctgtgtgcta taatacacca aaaggaaagc aaagtgaaaa ggaaacttg aatagccaag    8040 aagactcgga gtgcttcacg ccttcaccta tcccacatag gtgatgagct aagagtaaaa    8100
tgtagattct ctcgagtact gaatattgcc tgcactttc cttgcagtaa atacaccttt    8160
aatccatgac gagagtccac tctttgagtc cgtcttgaga ttcttccatt gatcatacaa    8220
catgacctcg aagtcctgat ggagaacaac ttatataatt aaaactacaa tacagaaagt    8280
tcctgacaat taaaaccttt ggtggtggca tgccgtaggt taaaaaaaat agataatgac    8340
```

```
aacacaactg agacacgct ctttgccgag tgctcacacg tttgctgaga gcgagcactc    8400
ggcaaatata tgatttgccg aataccaccc tcctcggcaa aacaatacac taggcaaaaa    8460
ggtagtttcc catcaccatg atgcccgccg ttaatgtacc ttctatgccg agtatgttgg    8520
cgctcagcaa agagatcgtt accggcgttt gtttcaccaa gagctctttg acgagtgtgg    8580
cacacgacaa aacctttgc cgagtgtaat tagtcgtttg ccaagtgact ggtgcagttg    8640
gcaaaggagt nnnnnnttat gtgtgggcaa aatgatatat ggtgccagtt agggctagc    8699
```

<210> SEQ ID NO 12
<211> LENGTH: 8114
<212> TYPE: DNA
<213> ORGANISM: Artificial Sequence
<220> FEATURE:
<223> OTHER INFORMATION: right genomic border and complete internal transgene in maize event DP-098140-6

<400> SEQUENCE: 12

```
atgaaaaagt ccaagtcgag caagggtacg taccgcggcc ggcggctaat tacggaggac      60
atgtcgtagt agctggtagt aaattaacac acgcgtacga gtagcggagt taaatggggg     120
catgcatgca gcaggacgtg gtattagtaa gcttactact ctagctttat ccatccatcc     180
atcgcgctag ctggctgcag gcacgggtta tcttatcttg tcgtccagag acgacacac      240 ggccggccgg tgaagtaaaa gggagtaatc ttattttgcc aggacgaggg gcggtacatg     300 atattcacaca cgtaccatgc atgcatatat gcatggacaa ggtacgtcgt cgtcgatcga     360
cgtcgatgca tatgtgtgta tgtatgtacg tgcataatgc atggtaccag ctgctggctt     420
atatatattt gtcaccgatc gatgcatgct gctgctctac acggtttgac actttaattt     480
gactcatcga tgaccttgct agatagtagc ggctcgtcaa ttaatgagcc atcaagttaa     540
caagagggca cgggcttgcg cgactgattc caccttatta acatacgccc tgcgcccgcg     600
cgtgctgtac gtacgagaat tcgaattac attaattcaa agctgtgtat gtatgtatat     660
atatatgtgc gtttttttgt gtgtgtatgt ctctttgctt ggtctttctc tatcgatccc     720
cctctttgat agtttaaact gaaggcggga aacgacaatc tgatcatgag cggagaatta     780
agggagtcac gttatgaccc ccgccgatga cgcgggacaa gccgttttac gtttggaact     840
gacagaaccg caacgttgaa ggagccactc agcaagctgg gccccccctc gaggtcggcc     900
gcattcgcaa aacacaccta gactagattt gttttgctaa cccaattgat attaattata     960
tatgattaat atttatatgt atatggattt ggttaatgaa atgcatctgg ttcatcaaag    1020
aattataaag acacgtgaca ttcatttagg ataagaaata tggatgatct cttctctttt    1080
tattcagata actagtaatt acacataaca cacaactttg atgcccacat tatagtgatt    1140
agcatgtcac tatgtgtgca tccttttatt tcatacatta attaagttgg ccaatccaga    1200
agatggacaa gtctaggtta actgactagc tagtcagtac acagtcctgc catcaccatc    1260
caggatcata tccttgaaag ccccaccact agggatcata ggcaacacat gctcctggtg    1320
tgggacgatt atatccaaga ggtacggccc tggagtctcg agcatcttct ttatcgctgc    1380
gcggacttcg ttcttctttg tcacacggac cgctggaatg ttgaaccctt tggcgatcgt    1440
cacgaaatct ggatatatct cactttcatt ctctgggttt cccaagtatg tgtgcgctct    1500
gttggcctta tagaacctgt cctccaactg caccaccatc cccaggtgct ggttgtttag    1560
cacaaagacc ttcaccggga ggttctcaat tcggatcata gctagctcct gaacgttcat    1620
gagaaagcta ccatctccat cgatgtcaac aacagtgaca cctgggttgg ccacagaagc    1680
```

```
accagcagca gccggcaaac caaatcccat agccccaaga ccagctgaag acaaccactg    1740
ccttggccgc ttgtaagtgt agtactgtgc cgcccacatc tggtgctgcc caacacctgt    1800
gccgatgatg gcctcgcctt tcgtcagctc atcaagaacc tgaatagcat attgtggctg    1860
gatctcctca ttagatgttt tatacccaag ggggaattcc ctcttctgct gatccaactc    1920
atcgttccat gagccaaagt caaagctctt ctttgatgtg cttccttcaa gaagagcatt    1980
catgccctga aaagcaagct taacatctgc acagatggac acatgtggct gcttgttctt    2040
gccaatctca gccggatcaa tatcaacgtg cacaatctta gccctgcttg caaaagcctc    2100
aatcttccct gtcacgcgat catcaaaccg cacaccaagt gcaagcaaca gatcggcctt    2160
atccactgca taatttgcat acaccgtccc atgcatacct agcatgcgca gagacagtgg    2220
gtcgtcgctg gggaagttgc cgaggcccat aagagtagtt gtgaccggga ttccagtcag    2280
ctccacaaag cgtcgcaact cctcaccaga tgctgcgcag ccaccgccca cataaagaac    2340
agggcgccgc gattcaccaa caagacgcag cacctgctca agcaactcag tcgcaggggg    2400
cttgggaagg cgcgcaatgt acccaggcag actcatgggc ttgtcccaga caggcaccgc    2460
catctgctgc tggatgtcct tggggatgtc gacaagcacc ggccctggtc gaccagagga    2520
ggcgaggaag aaagcctcct gcacgacgcg ggggatgtcg tcgacgtcga ggaccaggta    2580
gttgtgcttg gtgatggagc gggtgaccct cgacgatggg gtctcctgga aggcgtcggt    2640
gccaatcatg cgtcgcgcca cctgtcccgt gatggcgacc atggggacgg aatcgagcag    2700
cgcgtcggcg agcgcggaga ctaggttggt ggcgccgggg ccggaggtgg cgatgcagac    2760
gccgacgcgg cccgaggagc gcgcgtagcc ggaggcggca aaggcctccc cttgctcgtg    2820
gcggaagagg tggttggcga tgacggggga gcggtgagt gcctggtgga tctccatgga    2880
cgcgccgccg gggtaggcga agacgtcgcg gacgccgcag cgctcgaggg actcgacgag    2940
gatgtcagca cccttgcggg gctcggtggg gccccacggc cggagcgggg tggccggggg    3000
agccatcggc atggcgggtg acgccgctga gcacctgatg ggcgcggcga gggcgcggcg    3060
ggtggccagg aggtgcgccc ggcgcctcgc cttgggcgca gcggtagtgg cgccagtgag    3120
cgcggtagac gcggcggcgg cggtggccat ggttgcggcg gctgtctcgg aggcggcgcg    3180
agggttgggg gtgggtgcca cggacacgga gtgggagaaa gggggatgtg cgtggaggcc    3240
tccctgcttt tgttcagagg atgtgtggct cagatggtga tgggaatggg actcgcaaga    3300
cgacgacgac acgtccgtcg cccgaatacg tacacgctac agaccggacg gtggggcctg    3360
tcgacgtggg accacgtgtc ggcctggatt acaaacagtg gtgtccaccg agtgctggta    3420
cacgacagcg tgcgtcaagg aaggttttga actgttccgt taaaaaaaga ggggagattt    3480
tggacttgac tgtggacgac ggtgcatgtc atcggagtac agacggtact gacacaaggg    3540
gcccagacaa gggaatccaa acgggtcgca cccacctgcc aggctgccac ccgcaatccg    3600
caacagggaa accgggcaca gcccacaacc acaagatgag cagctgcggc gacagcgtca    3660
ggcccggtgt cggtgttagg gatggcaccc tttggctccc cgtatccgtc cccgcgacaa    3720
aaaaatttcc cgcggggatt cccacgaact cttgcgagag acatttcttc cccatccccg    3780
ttccccacgg ggataaatcc ccatcgggga tcctctagag tcgacctgca ggcatgcaag    3840
cttcggtccg cggccagctt gctaaccggg gcccccctc gaggtcatca catcaatcca    3900
cttgctttga agacgtggtt ggaacgtctt ctttttccac gatgctcctc gtgggtgggg    3960
gtccatcttt gggaccactg tcggcagagg catcttcaac gatggccttt cctttatcgc    4020
aatgatggca tttgtaggag ccaccttcct tttccactat cttcacaata aagtgacaga    4080
```

```
tagctgggca atggaatccg aggaggtttc cggatattac cctttgttga aaagtctcaa    4140
ttgcccttg gtcttctgag actgtatctt tgatatttt ggagtagaca agcgtgtcgt    4200
gctccaccat gttgacgaag attttcttct tgtcattgag tcgtaagaga ctctgtatga    4260
actgttcgcc agtctttacg gcgagttctg ttaggtcctc tatttgaatc tttgactcca    4320
tggacggtat cgataagcta gcttgatatc acatcaatcc acttgctttg aagacgtggt    4380
tggaacgtct tcttttcca cgatgctcct cgtgggtggg ggtccatctt tgggaccact    4440
gtcggcagag gcatcttcaa cgatggcctt tcctttatcg caatgatggc atttgtagga    4500
gccaccttcc ttttccacta tcttcacaat aaagtgacag atagctgggc aatggaatcc    4560
gaggaggttt ccggatatta cctttgttg aaagtctca attgccctt ggtcttctga    4620
gactgtatct tgatatttt tggagtagac aagcgtgtcg tgctccacca tgttgacgaa    4680
gattttcttc ttgtcattga gtcgtaagag actctgtatg aactgttcgc cagtctttac    4740
ggcgagttct gttaggtcct ctatttgaat ctttgactcc atgatcgaat tatcacatca    4800
atccacttgc tttgaagacg tggttggaac gtcttctttt tccacgatgc tcctcgtggg    4860
tgggggtcca tctttgggac cactgtcggc agaggcatct tcaacgatgg ccttttccttt    4920
atcgcaatga tggcatttgt aggagccacc ttcctttcc actatcttca aataaagtg    4980
acagatagct gggcaatgga atccgaggag gtttccggat attacccttt gttgaaaagt    5040
ctcaattgcc ctttggtctt ctgagactgt atctttgata ttttggagt agacaagcgt    5100
gtcgtgctcc accatgttga cgaagatttt cttcttgtca ttgagtcgta agagactctg    5160
tatgaactgt tcgccagtct ttacggcgag ttctgttagg tcctctattt gaatctttga    5220
ctccatggga attcctgcag cccgggatct aggagcttgc atgcctgcag tgcagcgtga    5280
cccggtcgtg cccctctcta gagataatga gcattgcatg tctaagttat aaaaaattac    5340
cacatatttt ttttgtcaca cttgtttgaa gtgcagtta tctatcttta tacatatat    5400
taaactttac tctacgaata atatataatta tagtactaca ataatatcag tgttttagag    5460
aatcatataa atgaacagtt agacatggtc taaaggacaa ttgagtattt tgacaacagg    5520
actctacagt tttatctttt tagtgtgcat gtgttctcct ttttttttgc aaatagcttc    5580
acctatataa tacttcatcc atttttattag tacatccatt tagggtttag ggttaatggt    5640
ttttatagac taattttttt agtacatcta ttttattcta ttttagcctc taaattaaga    5700
aaactaaaac tctatttag ttttttttatt taataattta gatataaaat agaataaaat    5760
aaagtgacta aaaattaaac aaataccctt taagaaatta aaaaaactaa ggaaacattt    5820
ttcttgtttc gagtagataa tgccagcctg ttaaacgccg tcgacgagtc taacggacac    5880
caaccagcga accagcagcg tcgcgtcggg ccaagcgaag cagacggcac ggcatctctg    5940
tcgctgcctc tggaccctc tcgagagttc cgctccaccg ttggacttgc tccgctgtcg    6000
gcatccagaa attgcgtggc ggagcggcag acgtgagccg gcacggcagg cggcctcctc    6060
ctcctctcac ggcaccggca gctacggggg attccttcc caccgctcct tcgctttccc    6120
ttcctcgccc gccgtaataa atagacaccc cctccacacc ctctttcccc aacctcgtgt    6180
tgttcggagc gcacacacac acaaccagat ctcccccaaa tccacccgtc ggcacctccg    6240
cttcaaggta cgccgctcgt cctccccccc cccctctct accttctcta gatcggcgtt    6300
ccggtccatg gttagggccc ggtagttcta cttctgttca tgtttgtgtt agatccgtgt    6360
ttgtgttaga tccgtgctgc tagcgttcgt acacggatgc gacctgtacg tcagacacgt    6420
tctgattgct aacttgccag tgtttctctt tggggaatcc tgggatggct ctagccgttc    6480
```

```
cgcagacggg atcgatttca tgattttttt tgtttcgttg catagggttt ggtttgccct    6540
tttcctttat ttcaatatat gccgtgcact tgtttgtcgg gtcatctttt catgctttt    6600 tttgtcttgg ttgtgatgat gtggtctggt tgggcggtcg ttctagatcg gagtagaatt    6660
ctgtttcaaa ctacctggtg gattattaa ttttggatct gtatgtgtgt gccatacata    6720
ttcatagtta cgaattgaag atgatggatg gaaatatcga tctaggatag gtatacatgt    6780
tgatgcgggt tttactgatg catatacaga gatgctttt gttcgcttgg ttgtgatgat    6840
gtggtgtggt tgggcggtcg ttcattcgtt ctagatcgga gtagaatact gtttcaaact    6900
acctggtgta tttattaatt ttggaactgt atgtgtgtgt catacatctt catagttacg    6960
agtttaagat ggatggaaat atcgatctag gataggtata catgttgatg tgggttttac    7020
tgatgcatat acatgatggc atatgcagca tctattcata tgctctaacc ttgagtacct    7080
atctattata ataaacaagt atgttttata attattttga tcttgatata cttggatgat    7140
ggcatatgca gcagctatat gtggattttt ttagccctgc cttcatacgc tatttatttg    7200
cttggtactg tttcttttgt cgatgctcac cctgttgttt ggtgttactt ctgcaggtcg    7260
accgccgggg atccacacga caccatggct attgaggtta agcctatcaa cgcagaggat    7320
acctatgacc ttaggcatag agtgctcaga ccaaaccagc ctatcgaagc ctgcatgttt    7380
gagtctgacc ttactaggag tgcatttcac cttggtggat tctacggagg taaactgatt    7440
tccgtggctt cattccacca agctgagcac tctgaacttc aaggtaagaa gcagtaccag    7500
cttagaggtg tggctacctt ggaaggttat agagagcaga aggctggttc cagtctcgtg    7560
aaacacgctg aagagattct cagaaagaga ggtgctgaca tgatctggtg taatgccagg    7620
acatctgctt caggatacta caggaagttg ggattcagtg agcaaggaga ggtgttcgat    7680
actcctccag ttggacctca catcctgatg tataagagga tcacataact agctagtcag    7740
ttaacctaga cttgtccatc ttctggattg gccaacttaa ttaatgtatg aaataaaagg    7800
atgcacacat agtgacatgc taatcactat aatgtgggca tcaaagttgt gtgttatgtg    7860
taattactag ttatctgaat aaaagagaaa gagatcatcc atatttctta tcctaaatga    7920
atgtcacgtg tctttataat tctttgatga accagatgca tttcattaac caaatccata    7980
tacatataaa tattaatcat atataattaa tatcaattgg gttagcaaaa caaatctagt    8040
ctaggtgtgt tttgcgaatt cagtacatta aaaacgtccg caatgtgtta ttaagttgtc    8100
taagcgtcaa tttg                                                      8114
```

<210> SEQ ID NO 13
<211> LENGTH: 26
<212> TYPE: DNA
<213> ORGANISM: Artificial Sequence
<220> FEATURE:
<223> OTHER INFORMATION: primer 100235

<400> SEQUENCE: 13
tgcatgcagc aggacgtggt attagt                                         26

<210> SEQ ID NO 14
<211> LENGTH: 24
<212> TYPE: DNA
<213> ORGANISM: Artificial Sequence
<220> FEATURE:
<223> OTHER INFORMATION: primer 99878

<400> SEQUENCE: 14
gcaacgttga aggagccact cagc                                           24

```
<210> SEQ ID NO 15
<211> LENGTH: 25
<212> TYPE: DNA
<213> ORGANISM: Artificial Sequence
<220> FEATURE:
<223> OTHER INFORMATION: primer 99885

<400> SEQUENCE: 15
gcagaaggct ggttccagtc tcgtg                                              25

<210> SEQ ID NO 16
<211> LENGTH: 24
<212> TYPE: DNA
<213> ORGANISM: Artificial Sequence
<220> FEATURE:
<223> OTHER INFORMATION: primer 100240

<400> SEQUENCE: 16
gactcggagt gcttcacgcc ttca                                               24

<210> SEQ ID NO 17
<211> LENGTH: 26
<212> TYPE: DNA
<213> ORGANISM: Artificial Sequence
<220> FEATURE:
<223> OTHER INFORMATION: primer 102588

<400> SEQUENCE: 17
gtccgcaatg tgttattaag ttgtct                                             26

<210> SEQ ID NO 18
<211> LENGTH: 26
<212> TYPE: DNA
<213> ORGANISM: Artificial Sequence
<220> FEATURE:
<223> OTHER INFORMATION: primer 102589

<400> SEQUENCE: 18 tttttctag gaaagctggt tacatg                                              26

<210> SEQ ID NO 19
<211> LENGTH: 13
<212> TYPE: DNA
<213> ORGANISM: Artificial Sequence
<220> FEATURE:
<223> OTHER INFORMATION: MOB taqman probe 102590

<400> SEQUENCE: 19
agcgtcaatt tgc                                                           13

<210> SEQ ID NO 20
<211> LENGTH: 32
<212> TYPE: DNA
<213> ORGANISM: Artificial Sequence
<220> FEATURE:
<223> OTHER INFORMATION: primer 06-O-1734

<400> SEQUENCE: 20
tatgcctaag gtcataggta tcctctgcgt tg                                      32

<210> SEQ ID NO 21
<211> LENGTH: 30
<212> TYPE: DNA
<213> ORGANISM: Artificial Sequence
<220> FEATURE:
<223> OTHER INFORMATION: primer 06-O-1738
```

<400> SEQUENCE: 21
tgatggcata tgcagcagct atatgtggat          30

<210> SEQ ID NO 22
<211> LENGTH: 25
<212> TYPE: DNA
<213> ORGANISM: Artificial Sequence
<220> FEATURE:
<223> OTHER INFORMATION: primer 02-0-197

<400> SEQUENCE: 22
ccgctgtatc acaagggctg gtacc          25

<210> SEQ ID NO 23
<211> LENGTH: 25
<212> TYPE: DNA
<213> ORGANISM: Artificial Sequence
<220> FEATURE:
<223> OTHER INFORMATION: primer 02-0-198

<400> SEQUENCE: 23
ggagcccgtg tagagcatga cgatc          25

<210> SEQ ID NO 24
<211> LENGTH: 185
<212> TYPE: DNA
<213> ORGANISM: Artificial Sequence
<220> FEATURE:
<223> OTHER INFORMATION: probe comprisng the 3' end of the internal
      transgene of Event DP-098140-6

<400> SEQUENCE: 24
gtctttataa ttctttgatg aaccagatgc atttcattaa ccaaatccat atacatataa          60
atattaatca tatataatta atatcaattg ggttagcaaa acaaatctag tctaggtgtg          120
ttttgcgaat tcagtacatt aaaaacgtcc gcaatgtgtt attaagttgt ctaagcgtca          180
atttg          185

<210> SEQ ID NO 25
<211> LENGTH: 25
<212> TYPE: DNA
<213> ORGANISM: Artificial Sequence
<220> FEATURE:
<223> OTHER INFORMATION: Oligo 06-O-1536

<400> SEQUENCE: 25
aagggtgctg acatcctcgt cgagt          25

<210> SEQ ID NO 26
<211> LENGTH: 25
<212> TYPE: DNA
<213> ORGANISM: Artificial Sequence
<220> FEATURE:
<223> OTHER INFORMATION: Oligo 06-O-1537

<400> SEQUENCE: 26
gtcccatgca tacctagcat gcgca          25

<210> SEQ ID NO 27
<211> LENGTH: 25
<212> TYPE: DNA
<213> ORGANISM: Artificial Sequence
<220> FEATURE:
<223> OTHER INFORMATION: Oligo 06-O-1538

<400> SEQUENCE: 27

```
ggataaggcc gatctgttgc ttgca                                           25
```

<210> SEQ ID NO 28
<211> LENGTH: 26
<212> TYPE: DNA
<213> ORGANISM: Artificial Sequence
<220> FEATURE:
<223> OTHER INFORMATION: Oligo 06-O-1539

<400> SEQUENCE: 28

```
tcagtacaca gtcctgccat caccat                                          26
```

<210> SEQ ID NO 29
<211> LENGTH: 20
<212> TYPE: DNA
<213> ORGANISM: Artificial Sequence
<220> FEATURE:
<223> OTHER INFORMATION: Oligo 06-O-1541

<400> SEQUENCE: 29

```
atggctattg aggttaagcc                                                 20
```

<210> SEQ ID NO 30
<211> LENGTH: 24
<212> TYPE: DNA
<213> ORGANISM: Artificial Sequence
<220> FEATURE:
<223> OTHER INFORMATION: Oligo 06-O-1542

<400> SEQUENCE: 30

```
cctcttatac atcaggatgt gagg                                            24
```

<210> SEQ ID NO 31
<211> LENGTH: 931
<212> TYPE: DNA
<213> ORGANISM: Artificial Sequence
<220> FEATURE:
<223> OTHER INFORMATION: Zm-HRA 3' probe

<400> SEQUENCE: 31

```
tcagtacaca gtcctgccat caccatccag gatcatatcc ttgaaagccc caccactagg     60
gatcataggc aacacatgct cctggtgtgg gacgattata tccaagaggt acggccctgg    120
agtctcgagc atcttcttta tcgctgcgcg gacttcgttc ttctttgtca cacggaccgc    180
tggaatgttg aacccttggg cgatcgtcac gaaatctgga tatatctcac tttcattctc    240
tgggtttccc aagtatgtgt gcgctctgtt ggccttatag aacctgtcct ccaactgcac    300
caccatcccc aggtgctggt tgtttagcac aaagacttc accgggaggt tctcaattcg     360
gatcatagct agctcctgaa cgttcatgag aaagctacca tctccatcga tgtcaacaac    420
agtgacacct gggttggcca cagaagcacc agcagcagcc ggcaaaccaa atccccatagc   480
cccaagacca gctgaagaca accactgcct tggccgcttg taagtgtagt actgtgccgc    540
ccacatctgg tgctgcccaa cctgtgcc gatgatggcc tcgcctttcg tcagctcatc      600
aagaacctga atagcatatt gtggctggat ctcctcatta gatgttttat acccaagggg    660
gaattccctc ttctgctgat ccaactcatc gttccatgag ccaaagtcaa agctcttctt    720
tgatgtgctt ccttcaagaa gagcattcat gccctgcaaa gcaagcttaa catctgcaca    780
gatggacaca tgtggctgct tgttcttgcc aatctcagcc ggatcaatat caacgtgcac    840
aatcttagcc ctgcttgcaa aagcctcaat cttccctgtc acgcgatcat caaaccgcac    900
accaagtgca agcaacagat cggccttatc c                                   931
```

<210> SEQ ID NO 32
<211> LENGTH: 770
<212> TYPE: DNA
<213> ORGANISM: Artificial Sequence
<220> FEATURE:
<223> OTHER INFORMATION: Zm-HRA 5' probe

<400> SEQUENCE: 32

```
gtcccatgca tacctagcat gcgcagagac agtgggtcgt cgctggggaa gttgccgagg        60
cccataagag tagttgtgac cgggattcca gtcagctcca caaagcgtcg caactcctca       120
ccagatgctg cgcagccacc gcccacataa agaacagggc gccgcgattc accaacaaga       180
cgcagcacct gctcaagcaa ctcagtcgca gggggcttgg gaaggcgcgc aatgtaccca       240
ggcagactca tgggcttgtc ccagacaggc accgccatct gctgctggat gtccttgggg       300
atgtcgacaa gcaccggccc tggtcgacca gaggaggcga ggaagaaagc ctcctgcacg       360
acgcggggga tgtcgtcgac gtcgaggacc aggtagttgt gcttggtgat ggagcgggtg       420
acctcgacga tgggcgtctc ctggaaggcg tcggtgccaa tcatgcgtcg cgccacctgt       480
cccgtgatgg cgaccatggg gacgaatcg agcagcgcgt cggcgagcgc ggagactagg        540
ttggtggcgc cggggccgga ggtggcgatg cagacgccga cgcggcccga ggagcgcgcg       600
tagccggagg cggcaaaggc ctccccttgc tcgtggcgga agaggtggtt ggcgatgacg       660
ggggagcggg tgagtgcctg gtggatctcc atggacgcgc cgccggggta ggcgaagacg       720
tcgcggacgc cgcagcgctc gagggactcg acgaggatgt cagcaccctt                  770
```

<210> SEQ ID NO 33
<211> LENGTH: 435
<212> TYPE: DNA
<213> ORGANISM: Artificial Sequence
<220> FEATURE:
<223> OTHER INFORMATION: GAT4621 probe

<400> SEQUENCE: 33

```
atggctattg aggttaagcc tatcaacgca gaggatacct atgaccttag gcatagagtg        60
ctcagaccaa accagcctat cgaagcctgc atgtttgagt ctgaccttac taggagtgca       120
tttcaccttg gtggattcta cggaggtaaa ctgatttccg tggcttcatt ccaccaagct       180
gagcactctg aacttcaagg taagaagcag taccagctta gaggtgtggc taccttggaa       240
ggttatagag agcagaaggc tggttccagt ctcgtgaaac acgctgaaga gattctcaga       300
aagagaggtg ctgacatgat ctggtgtaat gccaggacat ctgcttcagg atactacagg       360
aagttgggat tcagtgagca aggagaggtg ttcgatactc ctccagttgg acctcacatc       420
ctgatgtata agagg                                                        435
```

<210> SEQ ID NO 34
<211> LENGTH: 33
<212> TYPE: DNA
<213> ORGANISM: Artificial Sequence
<220> FEATURE:
<223> OTHER INFORMATION: oligo 06-o-1779

<400> SEQUENCE: 34

```
atgaaaaagt ccaagtcgag caagggtacg tac                                     33
```

<210> SEQ ID NO 35
<211> LENGTH: 32
<212> TYPE: DNA
<213> ORGANISM: Artificial Sequence

```
<220> FEATURE:
<223> OTHER INFORMATION: oligo 06-o-1782

<400> SEQUENCE: 35 gctagccctaactggcaccatatatcatttg                                32

<210> SEQ ID NO 36
<211> LENGTH: 27
<212> TYPE: DNA
<213> ORGANISM: Artificial Sequence
<220> FEATURE:
<223> OTHER INFORMATION: oligo 06-o-1783

<400> SEQUENCE: 36 aactgcaccagtcacttggcaaacgac                                    27

<210> SEQ ID NO 37
<211> LENGTH: 35
<212> TYPE: DNA
<213> ORGANISM: Artificial Sequence
<220> FEATURE:
<223> OTHER INFORMATION: oligo 06-o-1877

<400> SEQUENCE: 37 cgttttttgtgtgtgtatgtctctttgcttggtc                             35

<210> SEQ ID NO 38
<211> LENGTH: 35
<212> TYPE: DNA
<213> ORGANISM: Artificial Sequence
<220> FEATURE:
<223> OTHER INFORMATION: oligo 06-o-1878

<400> SEQUENCE: 38 tgtatgtctctttgcttggtcttttctctatcgatc                           35

<210> SEQ ID NO 39
<211> LENGTH: 35
<212> TYPE: DNA
<213> ORGANISM: Artificial Sequence
<220> FEATURE:
<223> OTHER INFORMATION: oligo 06-o-1879

<400> SEQUENCE: 39 atgacgtgatacaactttacttcagtataagactg                            35

<210> SEQ ID NO 40
<211> LENGTH: 35
<212> TYPE: DNA
<213> ORGANISM: Artificial Sequence
<220> FEATURE:
<223> OTHER INFORMATION: oligo 06-o-1880

<400> SEQUENCE: 40 caactatctcagtcttattctatgttcatgacgtg                            35

<210> SEQ ID NO 41
<211> LENGTH: 27
<212> TYPE: DNA
<213> ORGANISM: Artificial Sequence
<220> FEATURE:
<223> OTHER INFORMATION: oligo 06-o-1946

<400> SEQUENCE: 41 tcggagtacagacggtactgacacaag                                    27
```

```
<210> SEQ ID NO 42
<211> LENGTH: 30
<212> TYPE: DNA
<213> ORGANISM: Artificial Sequence
<220> FEATURE:
<223> OTHER INFORMATION: oligo 06-o-1947

<400> SEQUENCE: 42
cctctctaga gataatgagc attgcatgtc                                       30

<210> SEQ ID NO 43
<211> LENGTH: 26
<212> TYPE: DNA
<213> ORGANISM: Artificial Sequence
<220> FEATURE:
<223> OTHER INFORMATION: oligo 06-o-1948

<400> SEQUENCE: 43
gcgacccgtt tggattccct tgtctg                                           26

<210> SEQ ID NO 44
<211> LENGTH: 26
<212> TYPE: DNA
<213> ORGANISM: Artificial Sequence
<220> FEATURE:
<223> OTHER INFORMATION: oligo 06-o-1949

<400> SEQUENCE: 44
tgcaagctcc taatcccggg ctgcag                                           26

<210> SEQ ID NO 45
<211> LENGTH: 26
<212> TYPE: DNA
<213> ORGANISM: Artificial Sequence
<220> FEATURE:
<223> OTHER INFORMATION: oligo 06-o-1950

<400> SEQUENCE: 45
ctggttcgct ggttggtgtc cgttag                                           26

<210> SEQ ID NO 46
<211> LENGTH: 1311
<212> TYPE: DNA
<213> ORGANISM: Artificial Sequence
<220> FEATURE:
<223> OTHER INFORMATION: left border junction of maize event DP-098140-6
      (UD)

<400> SEQUENCE: 46
ctgtacatgt aaccagcttt cctagaaaaa aaacacagta atatttacag tatacaataa       60
tgctcattga ttagatccaa aattatgaaa tgtatatatt ttttgccata acttttatta     120
cagtcttata ctgaagtaaa gttgtatcac gtcatgaaca tagaataaga ctgagatagt     180
tgactaatcc agtcatatcc tatagtacac tagtaaggtg catgtgctaa caatatgaca     240
aatctagtat ttctttatag tttatcatcc ataaatcgca aaatacctaa gcataatttt     300
atttgaatag agagagtact gcccgttatt gtatgaggta atgacttcca tatatacaac     360
atagtcataa gaacacaatt atgaaaaaaa tctatttaaa attgaaatgc gttgagatct     420
tgtcttgcat actaaacata gtaaatataa attaatgcat aaatgactgt ataacagac      480 aatgctggtg acaatagaca atgtactgaa tctaactgga tacgtaggat gctgctatct     540
tattcactca tagttattca gatagtggtc attcttttg acccatagaa aactgtgtgc      600
tataatacac caaaaggaaa gcaaagtgaa aaggaaactt tgaatagcca agaagactcg     660
```

| | |
|---|---|
| gagtgcttca cgccttcacc tatcccacat aggtgatgag ctaagagtaa aatgtagatt | 720 |
| ctctcgagta ctgaatattg cctgcacttt tccttgcagt aaatacacct ttaatccatg | 780 |
| acgagagtcc actctttgag tccgtcttga gattcttcca ttgatcatac aacatgacct | 840 |
| cgaagtcctg atggagaaca acttatataa ttaaaactac aatacagaaa gttcctgaca | 900 |
| attaaaacct tggtggtgg catgccgtag gttaaaaaaa atagataatg acaacacaac | 960 |
| tggagacacg ctctttgccg agtgctcaca cgtttgctga gagcgagcac tcggcaaata | 1020 |
| tatgatttgc cgaataccac cctcctcggc aaaacaatac actaggcaaa aggtagttt | 1080 |
| cccatcacca tgatgcccgc cgttaatgta ccttctatgc cgagtatgtt ggcgctcagc | 1140 |
| aaagagatcg ttaccggcgt ttgtttcacc aagagctctt tgacgagtgt ggcacacgac | 1200 |
| aaaaccttt gccgagtgta attagtcgtt tgccaagtga ctggtgcagt tggcaaagga | 1260 |
| gtcgtttatt atgtgtgggc aaaatgatat atggtgccag ttagggctag c | 1311 |

<210> SEQ ID NO 47
<211> LENGTH: 7386
<212> TYPE: DNA
<213> ORGANISM: Artificial Sequence
<220> FEATURE:
<223> OTHER INFORMATION: Complete transgene of maize event DP-098140-6
      (UD)

<400> SEQUENCE: 47

| | |
|---|---|
| tgatagttta aactgaaggc gggaaacgac aatctgatca tgagcggaga attaagggag | 60 |
| tcacgttatg accccgccg atgacgcggg acaagccgtt ttacgtttgg aactgacaga | 120 |
| accgcaacgt tgaaggagcc actcagcaag ctgggccccc cctcgaggtc ggccgcattc | 180 |
| gcaaaacaca cctagactag atttgttttg ctaacccaat tgatattaat tatatatgat | 240 |
| taatatttat atgtatatgg atttggttaa tgaaatgcat ctggttcatc aaagaattat | 300 |
| aaagacacgt gacattcatt taggataaga aatatggatg atctcttct cttttattca | 360 |
| gataactagt aattacacat aacacacaac tttgatgccc acattatagt gattagcatg | 420 |
| tcactatgtg tgcatccttt tatttcatac attaattaag ttggccaatc cagaagatgg | 480 |
| acaagtctag gttaactgac tagctagtca gtacacagtc ctgccatcac catccaggat | 540 |
| catatccttg aaagccccac cactagggat cataggcaac acatgctcct ggtgtgggac | 600 |
| gattatatcc aagaggtacg gccctggagt ctcgagcatc ttctttatcg ctgcgcggac | 660 |
| ttcgttcttc tttgtcacac ggaccgctgg aatgttgaac cctttggcga tcgtcacgaa | 720 |
| atctggatat atctcacttt cattctctgg gtttcccaag tatgtgtgcg ctctgttggc | 780 |
| cttatagaac ctgtcctcca actgcaccac catccccagg tgctggttgt ttagcacaaa | 840 |
| gaccttcact ggaggttct caattcggat catagctagc tcctgaacgt tcatgagaaa | 900 |
| gctaccatct ccatcgatgt caacaacagt gacacctggg tttgccacag aagcaccagc | 960 |
| agcagccggc aaaccaaatc ccatagcccc aagaccagct gaagacaacc actgccttgg | 1020 |
| ccgcttgtaa gtgtagtact gtgccgccca catctggtgc tgcccaacac ctgtgccgat | 1080 |
| gatggcctcg cctttcgtca gctcatcaag aacctgaata gcatattgtg gctggatctc | 1140 |
| ctcattagat gttttatacc caagggggaa ttccctcttc tgctgatcca actcatcgtt | 1200 |
| ccatgagcca aagtcaaagc tcttctttga tgtgcttcct tcaagaagag cattcatgcc | 1260 |
| ctgcaaagca agcttaacat ctgcacagat ggacacatgt ggctgcttgt tcttgccaat | 1320 |
| ctcagccgga tcaatatcaa cgtgcacaat cttagccctg cttgcaaaag cctcaatctt | 1380 |
| ccctgtcacg cgatcatcaa accgcacacc aagtgcaagc aacagatcgg ccttatccac | 1440 |

-continued

```
tgcataattt gcatacaccg tcccatgcat acctagcatg cgcagagaca gtgggtcgtc     1500
gctggggaag ttgccgaggc ccataagagt agttgtgacc gggattccag tcagctccac     1560
aaagcgtcgc aactcctcac cagatgctgc gcagccaccg cccacataaa gaacagggcg     1620
ccgcgattca ccaacaagac gcagcacctg ctcaagcaac tcagtcgcag ggggcttggg     1680
aaggcgcgca atgtacccag gcagactcat gggcttgtcc cagacaggca ccgccatctg     1740
ctgctggatg tccttgggga tgtcgacaag caccggccct ggtcgaccag aggaggcgag     1800
gaagaaagcc tcctgcacga cgcggggat gtcgtcgacg tcgaggacca ggtagttgtg      1860
cttggtgatg gagcgggtga cctcgacgat gggcgtctcc tggaaggcgt cggtgccaat     1920
catgcgtcgc gccacctgtc ccgtgatggc gaccatgggg acggaatcga gcagcgcgtc     1980
ggcgagcgcg gagactaggt tggtggcgcc ggggccggag gtggcgatgc agacgccgac     2040
gcggcccgag gagcgcgcgt agccggaggc ggcaaaggcc tccccttgct cgtggcggaa     2100
gaggtggttg gcgatgacgg gggagcgggt gagtgcctgg tggatctcca tggacgcgcc     2160
gccggggtag gcgaagacgt cgcggacgcc gcagcgctcg agggactcga cgaggatgtc     2220
agcacccttg cggggctcgg tggggcccca cggccggagc ggggtggccg gggagccat      2280 cggcatggcg ggtgacgccg ctgagcacct gatgggcgcg gcgagggcgc ggcgggtggc     2340
caggaggtgc gcccggcgcc tcgccttggg cgcagcggta gtggcgccag tgagcgcggt     2400
agacgcggcg gcggcggtgg ccatggttgc ggcggctgtc tcggaggcgg cgcgagggtt     2460
tggggtgggt gccacggaca cggagtggga gaaaggggga tgtgcgtgga ggcctccctg     2520
cttttgttca gaggatgtgt ggctcagatg gtgatgggaa tgggactcgc aagacgacga     2580
cgacacgtcc gtcgcccgaa tacgtacacg ctacagaccg gacggtgggg cctgtcgacg     2640
tgggaccgac gtgtcggcct ggattacaaa cgtggtgtcc accgagtgct ggtacacgac     2700
agcgtgcgtc aaggaggttt tgaactgttc cgttaaaaaa agaggggaga ttttggactt     2760
gactgtggac gacggtgcat gtcatcggag tacagacggt actgacacaa ggggcccaga     2820
caagggaatc caaacgggtc gcacccacct gccaggctgc cacccgcaat ccgcaacagg     2880
gaaaccgggc acagcccaca accacaagat gagcagctgc ggcgacagcg tcaggcccgg     2940
tgtcggtgtt agggatggca cccttttggct ccccgtatcc gtcccgcgca caaaaaatt     3000 tcccgcgggg attcccacga actcttgcga gagacatttc ttccccatcc ccgttcccca     3060
cggggataaa tcccccatcgg ggatcctcta gagtcgacct gcaggcatgc aagcttcggt     3120
ccgcggccag cttgctaacc cgggccccc  ctcgaggtca tcacatcaat ccacttgctt     3180
tgaagacgtg gttggaacgt cttcttttc cacgatgctc ctcgtgggtg ggggtccatc      3240
tttgggacca ctgtcggcag aggcatcttc aacgatggcc tttcctttat cgcaatgatg     3300
gcatttgtag gagccaccttt cctttttccac tatcttcaca ataaagtgac agatagctgg     3360
gcaatggaat ccgaggaggt ttccggatat tacccttttgt tgaaaagtct caattgccct     3420
ttggtcttct gagactgtat ctttgatatt tttggagtag acaagcgtgt cgtgctccac     3480
catgttgacg aagattttct tcttgtcatt gagtcgtaag agactctgta tgaactgttc     3540
gccagtcttt acggcgagtt ctgttaggtc ctctatttga atctttgact ccatggacgg     3600
tatcgataag ctagcttgat atcacatcaa tccacttgct ttgaagacgt ggttggaacg     3660
tcttcttttt ccacgatgct cctcgtgggt ggggtccat cttttgggacc actgtcggca     3720 gaggcatctt caacgatggc ctttccttta tcgcaatgat ggcatttgta ggagccacct    3780 tcctttttcca ctatcttcac aataaagtga cagatagctg ggcaatggaa tccgaggagg   3840
```

```
tttccggata ttacccttTg ttgaaaagtc tcaattgccc tttggtcttc tgagactgta    3900
tctttgatat ttttggagta gacaagcgtg tcgtgctcca ccatgttgac gaagattttc    3960
ttcttgtcat tgagtcgtaa gagactctgt atgaactgtt cgccagtctt tacggcgagt    4020
tctgttaggt cctctatttg aatctttgac tccatgatcg aattatcaca tcaatccact    4080
tgctttgaag acgtggttgg aacgtcttct ttttccacga tgctcctcgt gggtgggggt    4140
ccatctttgg gaccactgtc ggcagaggca tcttcaacga tggcctttcc tttatcgcaa    4200
tgatggcatt tgtaggagcc accttccttt tccactatct tcacaataaa gtgacagata    4260
gctgggcaat ggaatccgag gaggtttccg gatattaccc tttgttgaaa agtctcaatt    4320
gcccttTggt cttctgagac tgtatctttg atattTttgg agtagacaag cgtgtcgtgc    4380
tccaccatgt tgacgaagat tttcttcttg tcattgagtc gtaagagact ctgtatgaac    4440
tgttcgccag tctttacggc gagttctgtt aggtcctcta tttgaatctt tgactccatg    4500
ggaattcctg cagcccggga ttaggagctt gcatgcctgc agtgcagcgt gacccggtcg    4560
tgccctctc tagagataat gagcattgca tgtctaagtt ataaaaatt accacatatt     4620
ttttttgtca cacttgtttg aagtgcagtt tatctatctt tatacatata tttaaactTt    4680
actctacgaa taatataatc tatagtacta caataatatc agtgttttag agaatcatat    4740
aaatgaacag ttagacatgg tctaaaggac aattgagtat tttgacaaca ggactctaca    4800
gttttatctt tttagtgtgc atgtgttctc cttttttttt gcaaatagct tcacctatat    4860
aatacttcat ccattttatt agtacatcca tttagggttt agggttaatg gtttttatag    4920
actaattttt ttagtacatc tattttattc tattttagcc tctaaattaa gaaaactaaa    4980
actctatttt agtttttta tttaataatt tagatataaa atagaataaa ataaagtgac    5040
taaaaattaa acaaataccc tttaagaaat taaaaaaact aaggaaacat ttttcttgtt    5100
tcgagtagat aatgccagcc tgttaaacgc cgtcgacgag tctaacggac accaaccagc    5160
gaaccagcag cgtcgcgtcg ggccaagcga agcagacggc acggcatctc tgtcgctgcc    5220
tctggacccc tctcgagagt tccgctccac cgttggactt gctccgctgt cggcatccag    5280
aaattgcgtg gcggagcggc agacgtgagc cggcacggca ggcggcctcc tcctcctctc    5340
acggcaccgg cagctacggg ggattccttt cccaccgctc cttcgctttc ccttcctcgc    5400
ccgccgtaat aaatagacac cccctccaca ccctctttcc ccaacctcgt gttgttcgga    5460
gcgcacacac acacaaccag atctccccca aatccacccg tcggcacctc cgcttcaagg    5520
tacgccgctc gtcctccccc ccccccctct ctaccttctc tagatcggcg ttccggtcca    5580
tggttagggc ccggtagttc tacttctgtt catgtttgtg ttagatccgt gtttgtgtta    5640
gatccgtgct gctagcgttc gtacacggat gcgacctgta cgtcagacac gttctgattg    5700
ctaacttgcc agtgtttctc tttggggaat cctgggatgg ctctagccgt tccgcagacg    5760
ggatcgattt catgattttt tttgtttcgt tgcatagggt ttggtttgcc cttttccttt    5820
atttcaatat atgccgtgca cttgtttgtc gggtcatctt ttcatgcttt tttttgtctt    5880
ggttgtgatg atgtggtctg gttgggcggt cgttctagat cggagtagaa ttctgtttca    5940
aactacctgg tggatttatt aattttggat ctgtatgtgt gtgccataca tattcatagt    6000
tacgaattga agatgatgga tggaaatatc gatctaggat aggtatacat gttgatgcgg    6060
gttttactga tgcatataca gagatgcttt ttgttcgctt ggttgtgatg atgtggtgtg    6120
gttgggcggt cgttcattcg ttctagatcg gagtagaata ctgttTcaaa ctacctggtg    6180
tatttattaa ttttggaact gtatgtgtgt gtcatacatc ttcatagtta cgagtttaag    6240
```

```
atggatggaa atatcgatct aggataggta tacatgttga tgtgggtttt actgatgcat      6300
atacatgatg gcatatgcag catctattca tatgctctaa ccttgagtac ctatctatta      6360
taataaacaa gtatgtttta taattatttt gatcttgata tacttggatg atggcatatg      6420
cagcagctat atgtggattt ttttagccct gccttcatac gctatttatt tgcttggtac      6480
tgtttctttt gtcgatgctc accctgttgt ttggtgttac ttctgcaggt cgaccgccgg      6540
ggatccacac gacaccatgg ctattgaggt taagcctatc aacgcagagg atacctatga      6600
ccttaggcat agagtgctca gaccaaacca gcctatcgaa gcctgcatgt ttgagtctga      6660
ccttactagg agtgcatttc accttggtgg attctacgga ggtaaactga tttccgtggc      6720
ttcattccac caagctgagc actctgaact tcaaggtaag aagcagtacc agcttagagg      6780
tgtggctacc ttggaaggtt atagagagca gaaggctggt tccagtctcg tgaaacacgc      6840
tgaagagatt ctcagaaaga gaggtgctga catgatctgg tgtaatgcca ggacatctgc      6900
ttcaggatac tacaggaagt tgggattcag tgagcaagga gaggtgttcg atactcctcc      6960
agttggacct cacatcctga tgtataagag gatcacataa ctagctagtc agttaaccta      7020
gacttgtcca tcttctggat tggccaactt aattaatgta tgaaataaaa ggatgcacac      7080
atagtgacat gctaatcact ataatgtggg catcaaagtt gtgtgttatg tgtaattact      7140
agttatctga ataaaagaga aagagatcat ccatatttct tatcctaaat gaatgtcacg      7200
tgtctttata attctttgat gaaccagatg catttcatta accaaatcca tatacatata      7260
aatattaatc atatataatt aatatcaatt gggttagcaa aacaaatcta gtctaggtgt      7320
gttttgcgaa ttcagtacat taaaaacgtc cgcaatgtgt tattaagttg tctaagcgtc      7380
aatttg                                                                 7386
```

<210> SEQ ID NO 48
<211> LENGTH: 9423
<212> TYPE: DNA
<213> ORGANISM: Artificial Sequence
<220> FEATURE:
<223> OTHER INFORMATION: Right and left junction borders and internal
      transgene in maize event DP-098140-6 (UD)

<400> SEQUENCE: 48

```
atgaaaaagt ccaagtcgag caagggtacg taccgcggcc ggcggctaat tacggaggac       60
atgtcgtagt agctggtagt aaattaacac acgcgtacga gtagcggagt taaatggggg      120
catgcatgca gcaggacgtg gtattagtaa gcttactact ctagctttat ccatccatcc      180
atcgcgctag ctggctgcag gcacgggtta tcttatcttg tcgtccagag gacgacacac      240
ggccggccgg tgaagtaaaa gggagtaatc ttattttgcc aggacgaggg gcggtacatg      300
atattacaca cgtaccatgc atgcatatat gcatggacaa ggtacgtcgt cgtcgatcga      360
cgtcgatgca tatgtgtgta tgtatgtacg tgcataatgc atggtaccag ctgctggctt      420
atatatattt gtcaccgatc gatgcatgct gctgctctac acggtttgac actttaatttt      480 gactcatcga tgaccttgct agatagtagc ggctcgtcaa ttaatgagcc atcaagttaa      540
caagagggca cgggcttgcg cgactgattc caccttatta acatacgccc tgcgcccgcg      600
cgtgctgtac gtacgagaat tcgaattacc attaattcaa agctgtgtat gtatgtatat      660
atatatgtgc gttttttttgt gtgtgtatgt ctctttgctt ggtctttctc tatcgatccc      720
cctctttgat agtttaaact gaaggcggga aacgacaatc tgatcatgag cggagaatta      780
agggagtcac gttatgaccc ccgccgatga cgcgggacaa gccgttttac gtttggaact      840
```

```
gacagaaccg caacgttgaa ggagccactc agcaagctgg gccccccctc gaggtcggcc      900
gcattcgcaa aacacaccta gactagattt gttttgctaa cccaattgat attaattata      960
tatgattaat atttatatgt atatggattt ggttaatgaa atgcatctgg ttcatcaaag     1020
aattataaag acacgtgaca ttcatttagg ataagaaata tggatgatct ctttctcttt     1080
tattcagata actagtaatt acacataaca cacaactttg atgcccacat tatagtgatt     1140
agcatgtcac tatgtgtgca tccttttatt tcatacatta attaagttgg ccaatccaga     1200
agatggacaa gtctaggtta actgactagc tagtcagtac acagtcctgc catcaccatc     1260
caggatcata tccttgaaag ccccaccact agggatcata gcaacacat gctcctggtg      1320 tgggacgatt atatccaaga ggtacggccc tggagtctcg agcatcttct ttatcgctgc     1380
gcggacttcg ttcttctttg tcacacggac cgctggaatg ttgaacccctt tggcgatcgt    1440 cacgaaatct ggatatatct cactttcatt ctctgggttt cccaagtatg tgtgcgctct     1500
gttggcctta tagaacctgt cctccaactg caccaccatc cccaggtgct ggttgtttag     1560
cacaaagacc ttcactggga ggttctcaat tcggatcata gctagctcct gaacgttcat     1620
gagaaagcta ccatctccat cgatgtcaac aacagtgaca cctgggtttg ccacagaagc     1680
accagcagca gccggcaaac caaatcccat agccccaaga ccagctgaag acaaccactg     1740
ccttggccgc ttgtaagtgt agtactgtgc cgcccacatc tggtgctgcc caacacctgt     1800
gccgatgatg gcctcgcctt tcgtcagctc atcaagaacc tgaatagcat attgtggctg     1860
gatctcctca ttagatgttt tatacccaag ggggaattcc ctcttctgct gatccaactc     1920
atcgttccat gagccaaagt caaagctctt ctttgatgtg cttccttcaa gaagagcatt     1980 catgcccctgc aaagcaagct taacatctgc acagatggac acatgtggct gcttgttctt    2040
gccaatctca gccggatcaa tatcaacgtg cacaatctta gccctgcttg caaaagcctc    2100
aatcttccct gtcacgcgat catcaaaccg cacaccaagt gcaagcaaca gatcggcctt     2160
atccactgca taatttgcat acaccgtccc atgcatacct agcatgcgca gagacagtgg     2220
gtcgtcgctg gggaagttgc cgaggcccat aagagtagtt gtgaccggga ttccagtcag     2280
ctccacaaag cgtcgcaact cctcaccaga tgctgcgcag ccaccgccca cataaagaac     2340
agggcgccgc gattcaccaa caagacgcag cacctgctca agcaactcag tcgcaggggg     2400
cttgggaagg cgcgcaatgt acccaggcag actcatgggc ttgtcccaga caggcaccgc     2460
catctgctgc tggatgtcct tggggatgtc gacaagcacc ggccctggtc gaccagagga     2520
ggcgaggaag aaagcctcct gcacgacgcg ggggatgtcg tcgacgtcga ggaccaggta     2580
gttgtgcttg gtgatggagc gggtgacctc gacgatgggc gtctcctgga aggcgtcggt     2640
gccaatcatg cgtcgcgcca cctgtcccgt gatggcgacc atgggacgg aatcgagcag      2700 cgcgtcggcg agcgcggaga ctaggttggt ggcgccgggg ccggaggtgg cgatgcagac     2760
gccgacgcgg cccgaggagc gcgcgtagcc ggaggcggca aaggcctccc cttgctcgtg     2820
gcggaagagg tggttggcga tgacggggga gcggtgagt gcctggtgga tctccatgga      2880
cgcgccgccg gggtaggcga agacgtcgcg gacgccgcag cgctcgaggg actcgacgag     2940
gatgtcagca cccttgcggg gctcggtggg gccccacggc cggagcgggg tggccggggg     3000
agccatcggc atggcgggtg acgccgctga gcacctgatg ggcgcggcga gggcgcggcg     3060
ggtggccagg aggtgcgccc ggcgcctcgc cttgggcgca gcggtagtgg cgccagtgag     3120
cgcggtagac gcggcggcgg cggtggccat ggttgcggcg gctgtctcgg aggcggcgcg     3180
agggtttggg gtgggtgcca cggacacgga gtgggagaaa gggggatgtg cgtggaggcc     3240
```

```
tccctgcttt tgttcagagg atgtgtggct cagatggtga tgggaatggg actcgcaaga    3300
cgacgacgac acgtccgtcg cccgaatacg tacacgctac agaccggacg gtggggcctg    3360
tcgacgtggg accgacgtgt cggcctggat tacaaacgtg gtgtccaccg agtgctggta    3420
cacgacagcg tgcgtcaagg aggttttgaa ctgttccgtt aaaaaaagag gggagatttt    3480
ggacttgact gtggacgacg gtgcatgtca tcggagtaca gacggtactg acacaagggg    3540
cccagacaag ggaatccaaa cgggtcgcac ccacctgcca ggctgccacc cgcaatccgc    3600
aacagggaaa ccgggcacag cccacaacca aagatgagc agctgcggcg acagcgtcag    3660
gcccggtgtc ggtgttaggg atggcaccct ttggctcccc gtatccgtcc ccgcgacaaa    3720
aaaatttccc gcggggattc ccacgaactc ttgcgagaga catttcttcc ccatccccgt    3780
tccccacggg gataaatccc catcggggat cctctagagt cgacctgcag gcatgcaagc    3840
ttcggtccgc ggccagcttg ctaacccggg ccccccctcg aggtcatcac atcaatccac    3900
ttgctttgaa gacgtggttg gaacgtcttc ttttccacg atgctcctcg tgggtggggg    3960
tccatctttg ggaccactgt cggcagaggc atcttcaacg atggcctttc ctttatcgca    4020
atgatggcat ttgtaggagc caccttcctt ttccactatc ttcacaataa agtgacagat    4080
agctgggcaa tggaatccga ggaggtttcc ggatattacc ctttgttgaa aagtctcaat    4140
tgcccttttgg tcttctgaga ctgtatcttt gatattttttg gagtagacaa gcgtgtcgtg    4200
ctccaccatg ttgacgaaga ttttcttctt gtcattgagt cgtaagagac tctgtatgaa    4260
ctgttcgcca gtctttacgg cgagttctgt taggtcctct atttgaatct ttgactccat    4320
ggacggtatc gataagctag cttgatatca catcaatcca cttgctttga agacgtggtt    4380
ggaacgtctt ctttttccac gatgctcctc gtgggtgggg gtccatcttt gggaccactg    4440
tcggcagagg catcttcaac gatggccttt cctttatcgc aatgatggca tttgtaggag    4500
ccaccttcct tttccactat cttcacaata agtgacaga tagctgggca atggaatccg    4560
aggaggtttc cggatattac cctttgttga aaagtctcaa ttgccctttg gtcttctgag    4620
actgtatctt tgatattttt ggagtagaca agcgtgtcgt gctccaccat gttgacgaag    4680
atttttcttct tgtcattgag tcgtaagaga ctctgtatga actgttcgcc agtctttacg    4740
gcgagtctg ttaggtcctc tatttgaatc tttgactcca tgatcgaatt atcacatcaa    4800
tccacttgct ttgaagacgt ggttggaacg tcttcttttt ccacgatgct cctcgtgggt    4860
ggggtccat ctttgggacc actgtcggca gaggcatctt caacgatggc ctttcctttta    4920
tcgcaatgat ggcatttgta ggagccacct tcctttccca ctatcttcac aataaagtga    4980
cagatagctg gcaatggaa tccgaggagg tttccggata ttacccttg ttgaaaagtc    5040
tcaattgccc tttggtcttc tgagactgta tctttgatat ttttggagta gacaagcgtg    5100
tcgtgctcca ccatgttgac gaagattttc ttcttgtcat tgagtcgtaa gagactctgt    5160
atgaactgtt cgccagtctt tacgcgagt tctgttaggt cctctatttg aatctttgac    5220
tccatgggaa ttcctgcagc ccgggattag agcttgcat gcctgcagtg cagcgtgacc    5280
cggtcgtgcc cctctctaga gataatgagc attgcatgtc taagttataa aaaattacca    5340
catattttttt ttgtcacact tgtttgaagt gcagtttatc tatctttata catatattta    5400
aactttactc tacgaataat ataatctata gtactacaat aatatcagtg ttttagagaa    5460
tcatataaat gaacagttag acatggtcta aaggacaatt gagtattttg acaacaggac    5520
tctacagttt tatctttttta gtgtgcatgt gttctccttt tttttttgcaa atagcttcac    5580
ctatataata cttcatccat tttattagta catccattta gggtttaggg ttaatggttt    5640
```

```
ttatagacta atttttttag tacatctatt ttattctatt ttagcctcta aattaagaaa    5700
actaaaactc tattttagtt tttttattta ataatttaga tataaaatag aataaaataa    5760
agtgactaaa aattaaacaa atacccttta agaaattaaa aaaactaagg aaacattttt    5820
cttgtttcga gtagataatg ccagcctgtt aaacgccgtc gacgagtcta acggacacca    5880
accagcgaac cagcagcgtc gcgtcgggcc aagcgaagca gacggcacgg catctctgtc    5940
gctgcctctg gacccctctc gagagttccg ctccaccgtt ggacttgctc cgctgtcggc    6000
atccagaaat tgcgtggcgg agcggcagac gtgagccggc acggcaggcg gcctcctcct    6060
cctctcacgg caccggcagc tacggggat tcctttccca ccgctccttc gctttccctt      6120
cctcgcccgc cgtaataaat agacaccccc tccacaccct ctttccccaa cctcgtgttg    6180
ttcggagcgc acacacacac aaccagatct cccccaaatc cacccgtcgg cacctccgct    6240
tcaaggtacg ccgctcgtcc tccccccccc ccctctctac cttctctaga tcggcgttcc    6300
ggtccatggt tagggcccgg tagttctact tctgttcatg tttgtgttag atccgtgttt    6360
gtgttagatc cgtgctgcta gcgttcgtac acggatgcga cctgtacgtc agacacgttc    6420
tgattgctaa cttgccagtg tttctctttg gggaatcctg ggatggctct agccgttccg    6480
cagacgggat cgatttcatg attttttttg tttcgttgca tagggtttgg tttgcccttt    6540
tcctttattt caatatatgc cgtgcacttg tttgtcgggt catcttttca tgctttttt     6600
tgtcttggtt gtgatgatgt ggtctggttg ggcggtcgtt ctagatcgga gtagaattct    6660
gtttcaaact acctggtgga tttattaatt ttggatctgt atgtgtgtgc catacatatt    6720
catagttacg aattgaagat gatggatgga aatatcgatc taggataggt atacatgttg    6780
atgcgggttt tactgatgca tatacagaga tgcttttttgt tcgcttggtt gtgatgatgt    6840
ggtgtggttg ggcggtcgtt cattcgttct agatcggagt agaatactgt ttcaaactac    6900
ctggtgtatt tattaatttt ggaactgtat gtgtgtgtca tacatcttca tagttacgag    6960
tttaagatgg atggaaatat cgatctagga taggtataca tgttgatgtg ggttttactg    7020
atgcatatac atgatggcat atgcagcatc tattcatatg ctctaacctt gagtacctat    7080
ctattataat aaacaagtat gttttataat tattttgatc ttgatatact tggatgatgg    7140
catatgcagc agctatatgt ggattttttt agccctgcct tcatacgcta tttatttgct    7200
tggtactgtt tcttttgtcg atgctcaccc tgttgtttgg tgttacttct gcaggtcgac    7260
cgccggggat ccacacgaca ccatggctat tgaggttaag cctatcaacg cagaggatac    7320
ctatgacctt aggcatagag tgctcagacc aaaccagcct atcgaagcct gcatgtttga    7380
gtctgacctt actaggagtg catttcacct tggtggattc tacggaggta aactgatttc    7440
cgtggcttca ttccaccaag ctgagcactc tgaacttcaa ggtaagaagc agtaccagct    7500
tagaggtgtg gctaccttgg aaggttatag agagcagaag gctggttcca gtctcgtgaa    7560
acacgctgaa gagattctca gaaagagagg tgctgacatg atctggtgta atgccaggac    7620
atctgcttca ggatactaca ggaagttggg attcagtgag caaggagagg tgttcgatac    7680
tcctccagtt ggacctcaca tcctgatgta taagaggatc acataactag ctagtcagtt    7740
aacctagact tgtccatctt ctggattggc caacttaatt aatgtatgaa ataaaggat     7800
gcacacatag tgcatgcta atcactataa tgtgggcatc aaagttgtgt gttatgtgta    7860
attactagtt atctgaataa aagagaaaga gatcatccat atttcttatc ctaaatgaat    7920
gtcacgtgtc tttataattc tttgatgaac cagatgcatt tcattaacca aatccatata    7980
catataaata ttaatcatat ataattaata tcaattgggt tagcaaaaca aatctagtct    8040
```

-continued

| | |
|---|---|
| aggtgtgttt tgcgaattca gtacattaaa aacgtccgca atgtgttatt aagttgtcta | 8100 |
| agcgtcaatt tgctgtacat gtaaccagct ttcctagaaa aaaaacacag taatatttac | 8160 |
| agtatacaat aatgctcatt gattagatcc aaaattatga aatgtatata ttttttgcca | 8220 |
| taacttttat tacagtctta tactgaagta aagttgtatc acgtcatgaa catagaataa | 8280 |
| gactgagata gttgactaat ccagtcatat cctatagtac actagtaagg tgcatgtgct | 8340 |
| aacaatatga caaatctagt atttctttat agtttatcat ccataaatcg caaaatacct | 8400 |
| aagcataatt ttatttgaat agagagagta ctgcccgtta ttgtatgagg taatgacttc | 8460 |
| catatataca acatagtcat aagaacacaa ttatgaaaaa aatctattta aaattgaaat | 8520 |
| gcgttgagat cttgtcttgc atactaaaca tagtaaatat aaattaatgc ataaatgact | 8580 |
| gttataacag acaatgctgg tgacaataga caatgtactg aatctaactg gatacgtagg | 8640 |
| atgctgctat cttattcact catagttatt cagatagtgg tcattctttt tgacccatag | 8700 |
| aaaactgtgt gctataatac accaaaagga aagcaaagtg aaaaggaaac tttgaatagc | 8760 |
| caagaagact cggagtgctt cacgccttca cctatcccac ataggtgatg agctaagagt | 8820 |
| aaaatgtaga ttctctcgag tactgaatat tgcctgcact tttccttgca gtaaatacac | 8880 |
| ctttaatcca tgacgagagt ccactctttg agtccgtctt gagattcttc cattgatcat | 8940 |
| acaacatgac ctcgaagtcc tgatggagaa caacttatat aattaaaact acaatacaga | 9000 |
| aagttcctga caattaaaac ctttggtggt ggcatgccgt aggttaaaaa aaatagataa | 9060 |
| tgacaacaca actggagaca cgctctttgc cgagtgctca cacgtttgct gagagcgagc | 9120 |
| actcggcaaa tatatgattt gccgaatacc accctcctcg gcaaaacaat acactaggca | 9180 |
| aaaaggtagt ttcccatcac catgatgccc gccgttaatg taccttctat gccgagtatg | 9240 |
| ttggcgctca gcaaagagat cgttaccggc gtttgtttca ccaagagctc tttgacgagt | 9300 |
| gtggcacacg acaaaacctt ttgccgagtg taattagtcg tttgccaagt gactggtgca | 9360 |
| gttggcaaag gagtcgttta ttatgtgtgg gcaaaatgat atatggtgcc agttagggct | 9420 |
| agc | 9423 |

<210> SEQ ID NO 49
<211> LENGTH: 8697
<212> TYPE: DNA
<213> ORGANISM: Artificial Sequence
<220> FEATURE:
<223> OTHER INFORMATION: Left genomic border and complete internal
      transgene in maize event DP-098140-6 (UD)

<400> SEQUENCE: 49

| | |
|---|---|
| tgatagttta aactgaaggc gggaaacgac aatctgatca tgagcggaga attaagggag | 60 |
| tcacgttatg accccgccg atgacgcggg acaagccgtt ttacgtttgg aactgacaga | 120 |
| accgcaacgt tgaaggagcc actcagcaag ctgggccccc cctcgaggtc ggccgcattc | 180 |
| gcaaaacaca cctagactag atttgttttg ctaacccaat tgatattaat tatatatgat | 240 |
| taatatttat atgtatatgg atttggttaa tgaaatgcat ctggttcatc aaagaattat | 300 |
| aaagacacgt gacattcatt taggataaga aatatggatg atctctttct cttttattca | 360 |
| gataactagt aattacacat aacacacaac tttgatgccc acattatagt gattagcatg | 420 |
| tcactatgtg tgcatccttt tatttcatac attaattaag ttggcaatc cagaagatgg | 480 |
| acaagtctag gttaactgac tagctagtca gtacacagtc ctgccatcac catccaggat | 540 |
| catatccttg aaagccccac cactaggat cataggcaac acatgctcct ggtgtgggac | 600 |
| gattatatcc aagaggtacg gccctggagt ctcgagcatc ttctttatcg ctgcgcggac | 660 |

```
ttcgttcttc tttgtcacac ggaccgctgg aatgttgaac cctttggcga tcgtcacgaa      720
atctggatat atctcacttt cattctctgg gtttcccaag tatgtgtgcg ctctgttggc      780
cttatagaac ctgtcctcca actgcaccac catcccagg tgctggttgt ttagcacaaa       840
gaccttcact gggaggttct caattcggat catagctagc tcctgaacgt tcatgagaaa      900
gctaccatct ccatcgatgt caacaacagt gacacctggg tttgccacag aagcaccagc      960
agcagccggc aaaccaaatc ccatagcccc aagaccagct gaagacaacc actgccttgg     1020
ccgcttgtaa gtgtagtact gtgccgccca catctggtgc tgcccaacac ctgtgccgat     1080
gatggcctcg cctttcgtca gctcatcaag aacctgaata gcatattgtg gctggatctc     1140
ctcattagat gttttatacc caaggggga ttccctcttc tgctgatcca actcatcgtt      1200
ccatgagcca aagtcaaagc tcttctttga tgtgcttcct tcaagaagag cattcatgcc     1260
ctgcaaagca agcttaacat ctgcacagat ggacacatgt ggctgcttgt tcttgccaat     1320
ctcagccgga tcaatatcaa cgtgcacaat cttagccctg cttgcaaaag cctcaatctt     1380
ccctgtcacg cgatcatcaa accgcacacc aagtgcaagc aacagatcgg ccttatccac     1440
tgcataattt gcatacaccg tcccatgcat acctagcatg cgcagagaca gtgggtcgtc     1500
gctggggaag ttgccgaggc ccataagagt agttgtgacc gggattccag tcagctccac     1560
aaagcgtcgc aactcctcac cagatgctgc gcagccaccg cccacataaa gaacagggcg     1620
ccgcgattca ccaacaagac gcagcacctg ctcaagcaac tcagtcgcag ggggcttggg     1680
aaggcgcgca atgtacccag gcagactcat gggcttgtcc cagacaggca ccgccatctg     1740
ctgctggatg tccttgggga tgtcgacaag caccggccct ggtcgaccag aggaggcgag     1800
gaagaaagcc tcctgcacga cgcggggat gtcgtcgacg tcgaggacca ggtagttgtg      1860
cttggtgatg gagcgggtga cctcgacgat gggcgtctcc tggaaggcgt cggtgccaat     1920
catgcgtcgc gccacctgtc ccgtgatggc gaccatgggg acggaatcga gcagcgcgtc     1980
ggcgagcgcg gagactaggt tggtggcgcc ggggccggag gtggcgatgc agacgccgac     2040
gcggcccgag gagcgcgcgt agccggaggc ggcaaaggcc tcccctttgct cgtgcggaa     2100 gaggtggttg gcgatgacgg gggagcgggt gagtgcctgg tggatctcca tggacgcgcc     2160
gccggggtag gcgaagacgt cgcggacgcc gcagcgctcg agggactcga cgaggatgtc     2220
agcacccttg cggggctcgg tggggcccca cggccggagc ggggtggccg ggggagccat     2280
cggcatggcg ggtgacgccg ctgagcacct gatgggcgcg gcgagggcgc ggcgggtggc     2340
caggaggtgc gcccggcgcc tcgccttggg cgcagcggta gtggcgccag tgagcgcggt     2400
agacgcggcg gcggcggtgg ccatggttgc ggcggctgtc tcggaggcgg cgcgagggtt     2460
tggggtgggt gccacggaca cggagtggga gaaaggggga tgtgcgtgga ggcctccctg     2520
cttttgttca gaggatgtgt ggctcagatg gtgatgggaa tgggactcgc aagacgacga     2580
cgacacgtcc gtcgcccgaa tacgtacacg ctacagaccg gacggtgggg cctgtcgacg     2640
tgggaccgac gtgtcggcct ggattacaaa cgtggtgtcc accgagtgct ggtacacgac     2700
agcgtgcgtc aaggaggttt tgaactgttc cgttaaaaaa agaggggaga ttttggactt     2760
gactgtggac gacggtgcat gtcatcggag tacagacggt actgacacaa ggggcccaga     2820
caagggaatc caaacgggtc gcaccccacct gccaggctgc cacccgcaat ccgcaacagg     2880
gaaaccgggc acagcccaca accacaagat gagcagctgc ggcgacagcg tcaggcccgg     2940
tgtcggtgtt agggatggca cccttttggct ccccgtatcc gtcccgcgca caaaaaatt     3000 tcccgcgggg attcccacga actcttgcga gagacatttc ttccccatcc ccgttcccca     3060
```

```
cggggataaa tcccatcgg ggatcctcta gagtcgacct gcaggcatgc aagcttcggt    3120
ccgcggccag cttgctaacc cgggccccc ctcgaggtca tcacatcaat ccacttgctt    3180
tgaagacgtg gttggaacgt cttcttttc cacgatgctc ctcgtgggtg ggggtccatc    3240
tttgggacca ctgtcggcag aggcatcttc aacgatggcc tttccttat cgcaatgatg    3300 gcatttgtag gagccacctt ccttttccac tatcttcaca ataaagtgac agatagctgg    3360
gcaatggaat ccgaggaggt ttccggatat tacccttgt tgaaagtct caattgccct    3420 ttggtcttct gagactgtat ctttgatatt tttggagtag acaagcgtgt cgtgctccac    3480
catgttgacg aagatttct tcttgtcatt gagtcgtaag agactctgta tgaactgttc    3540
gccagtcttt acggcgagtt ctgttaggtc ctctatttga atctttgact ccatggacgg    3600
tatcgataag ctagcttgat atcacatcaa tccacttgct tgaagacgt ggttggaacg    3660 tcttcttttt ccacgatgct cctcgtgggt ggggtccat ctttgggacc actgtcggca    3720
gaggcatctt caacgatggc ctttccttta tcgcaatgat ggcatttgta ggagccacct    3780
tccttttcca ctatcttcac aataaagtga cagatagctg gcaatggaa tccgaggagg    3840 tttccggata ttacccttg ttgaaagtc tcaattgccc tttggtcttc tgagactgta    3900
tctttgatat ttttggagta cacaagcgtg tcgtgctcca ccatgttgac gaagattttc    3960
ttcttgtcat tgagtcgtaa gagactctgt atgaactgtt cgccagtctt tacggcgagt    4020
tctgttaggt cctctatttg aatctttgac ccatgatcg aattatcaca tcaatccact    4080
tgctttgaag acgtggttgg aacgtcttct ttttccacga tgctcctcgt gggtggggt    4140 ccatctttgg gaccactgtc ggcagaggca tcttcaacga tggccttcc tttatcgcaa    4200 tgatggcatt tgtaggagcc accttcctt tccactatct tcacaataaa gtgacagata    4260
gctgggcaat ggaatccgag gaggtttccg gatattaccc tttgttgaaa agtctcaatt    4320 gcccttggt cttctgagac tgtatctttg atattttgg agtagacaag cgtgtcgtgc    4380
tccaccatgt tgacgaagat tttcttcttg tcattgagtc gtaagagact ctgtatgaac    4440
tgttcgccag tctttacggc gagttctgtt aggtcctcta tttgaatctt tgactccatg    4500
ggaattcctg cagcccggga ttaggagctt gcatgcctgc agtgcagcgt gacccggtcg    4560
tgcccctctc tagagataat gagcattgca tgtctaagtt ataaaaaatt accacatatt    4620
ttttttgtca cacttgtttg aagtgcagtt tatctatctt tatacatata tttaaacttt    4680
actctacgaa taatataatc tatagtacta caataatatc agtgttttag agaatcatat    4740
aaatgaacag ttagacatgg tctaaaggac aattgagtat tttgacaaca ggactctaca    4800
gttttatctt tttagtgtgc atgtgttctc cttttttttt gcaaatagct tcacctatat    4860
aatacttcat ccattttatt agtacatcca tttagggttt agggtaatg gttttatag    4920 actaattttt ttagtacatc tattttattc tattttagcc tctaaattaa gaaaactaaa    4980
actctatttt agtttttta tttaataatt tagatataaa atagaataaa ataaagtgac    5040
taaaaattaa acaaataccc tttaagaaat taaaaaaact aaggaaacat ttttcttgtt    5100
tcgagtagat aatgccagcc tgttaaacgc cgtcgacgag tctaacggac accaaccagc    5160
gaaccagcag cgtcgcgtcg ggccaagcga agcagacggc acggcatctc tgtcgctgcc    5220 tctgacccc tctcgagagt tccgctccac cgttggactt gctccgctgt cggcatccag    5280
aaattgcgtg gcggagcggc agacgtgagc cggcacggca ggcggcctcc tcctcctctc    5340
acggcaccgg cagctacggg ggattccttt cccaccgctc cttcgctttc ccttcctcgc    5400
ccgccgtaat aaatagacac cccctccaca ccctctttcc ccaacctcgt gttgttcgga    5460
```

```
gcgcacacac acacaaccag atctccccca aatccacccg tcggcacctc cgcttcaagg   5520
tacgccgctc gtcctccccc ccccccctct ctaccttctc tagatcggcg ttccggtcca   5580
tggttagggc ccggtagttc tacttctgtt catgtttgtg ttagatccgt gtttgtgtta   5640
gatccgtgct gctagcgttc gtacacggat gcgacctgta cgtcagacac gttctgattg   5700
ctaacttgcc agtgtttctc tttggggaat cctgggatgg ctctagccgt tccgcagacg   5760
ggatcgattt catgattttt tttgtttcgt tgcatagggt ttggtttgcc cttttccttt   5820
atttcaatat atgccgtgca cttgtttgtc gggtcatctt ttcatgcttt tttttgtctt   5880
ggttgtgatg atgtggtctg gttgggcggt cgttctagat cggagtagaa ttctgtttca   5940
aactacctgg tggatttatt aattttggat ctgtatgtgt gtgccataca tattcatagt   6000
tacgaattga agatgatgga tggaaatatc gatctaggat aggtatacat gttgatgcgg   6060
gttttactga tgcatataca gagatgcttt ttgttcgctt ggttgtgatg atgtggtgtg   6120
gttgggcggt cgttcattcg ttctagatcg gagtagaata ctgtttcaaa ctacctggtg   6180
tatttattaa ttttggaact gtatgtgtgt gtcatacatc ttcatagtta cgagtttaag   6240
atggatggaa atatcgatct aggataggta tacatgttga tgtgggtttt actgatgcat   6300
atacatgatg gcatatgcag catctattca tatgctctaa ccttgagtac ctatctatta   6360
taataaacaa gtatgtttta taattatttt gatcttgata tacttggatg atggcatatg   6420
cagcagctat atgtggattt ttttagccct gccttcatac gctatttatt tgcttggtac   6480
tgtttctttt gtcgatgctc accctgttgt ttggtgttac ttctgcaggt cgaccgccgg   6540
ggatccacac gacaccatgg ctattgaggt taagcctatc aacgcagagg atacctatga   6600
ccttaggcat agagtgctca gaccaaacca gcctatcgaa gcctgcatgt ttgagtctga   6660
ccttactagg agtgcatttc accttggtgg attctacgga ggtaaactga tttccgtggc   6720
ttcattccac caagctgagc actctgaact tcaaggtaag aagcagtacc agcttagagg   6780
tgtggctacc ttggaaggtt atagagagca gaaggctggt tccagtctcg tgaaacacgc   6840
tgaagagatt ctcagaaaga gaggtgctga catgatctgg tgtaatgcca ggacatctgc   6900
ttcaggatac tacaggaagt tgggattcag tgagcaagga gaggtgttcg atactcctcc   6960
agttggacct cacatcctga tgtataagag gatcacataa ctagctagtc agttaaccta   7020
gacttgtcca tcttctggat tggccaactt aattaatgta tgaaataaaa ggatgcacac   7080
atagtgacat gctaatcact ataatgtggg catcaaagtt gtgtgttatg tgtaattact   7140
agttatctga ataaaagaga aagagatcat ccatatttct tatcctaaat gaatgtcacg   7200
tgtctttata attctttgat gaaccagatg catttcatta accaaatcca tatacatata   7260
aatattaatc atatataatt aatatcaatt gggttagcaa aacaaatcta gtctaggtgt   7320
gttttgcgaa ttcagtacat taaaaacgtc cgcaatgtgt tattaagttg tctaagcgtc   7380
aatttgctgt acatgtaacc agctttccta gaaaaaaaac acagtaatat ttacagtata   7440
caataatgct cattgattag atccaaaatt atgaaatgta tatttttt gccataactt   7500
ttattacagt cttatactga agtaaagttg tatcacgtca tgaacataga ataagactga   7560
gatagttgac taatccagtc atatcctata gtacactagt aaggtgcatg tgctaacaat   7620
atgacaaatc tagtatttct ttatagttta tcatccataa atcgcaaaat acctaagcat   7680
aattttattt gaatagagag agtactgccc gttattgtat gaggtaatga cttccatata   7740
tacaacatag tcataagaac acaattatga aaaaatctca tttaaaattg aaatgcgttg   7800
agatcttgtc ttgcatacta aacatagtaa atataaatta atgcataaat gactgttata   7860
```

```
acagacaatg ctggtgacaa tagacaatgt actgaatcta actggatacg taggatgctg    7920
ctatcttatt cactcatagt tattcagata gtggtcattc tttttgaccc atagaaaact    7980
gtgtgctata atacaccaaa aggaaagcaa agtgaaaagg aaactttgaa tagccaagaa    8040
gactcggagt gcttcacgcc ttcacctatc ccacataggt gatgagctaa gagtaaaatg    8100
tagattctct cgagtactga atattgcctg cacttttcct tgcagtaaat acacctttaa    8160
tccatgacga gagtccactc tttgagtccg tcttgagatt cttccattga tcatacaaca    8220
tgacctcgaa gtcctgatgg agaacaactt atataattaa aactacaata cagaaagttc    8280
ctgacaatta aaacctttgg tggtggcatg ccgtaggtta aaaaaaatag ataatgacaa    8340
cacaactgga gacacgctct tgccgagtg ctcacgtt tgctgagagc gagcactcgg       8400
caaatatatg atttgccgaa taccaccctc ctcggcaaaa caatacacta ggcaaaaagg    8460
tagtttccca tcaccatgat gcccgccgtt aatgtacctt ctatgccgag tatgttggcg    8520
ctcagcaaag agatcgttac cggcgtttgt ttcaccaaga gctctttgac gagtgtggca    8580
cacgacaaaa ccttttgccg agtgtaatta gtcgtttgcc aagtgactgg tgcagttggc    8640
aaaggagtcg tttattatgt gtgggcaaaa tgatatatgg tgccagttag ggctagc      8697
```

<210> SEQ ID NO 50
<211> LENGTH: 8112
<212> TYPE: DNA
<213> ORGANISM: Artificial Sequence
<220> FEATURE:
<223> OTHER INFORMATION: right genomic border and complete internal
      transgene in maize event DP-098140-6 (UD)

<400> SEQUENCE: 50

```
atgaaaaagt ccaagtcgag caagggtacg taccgcggcc ggcggctaat tacggaggac      60
atgtcgtagt agctggtagt aaattaacac acgcgtacga gtagcggagt taaatgggg      120 catgcatgca gcaggacgtg gtattagtaa gcttactact ctagctttat ccatccatcc    180
atcgcgctag ctggctgcag gcacgggtta tcttatcttg tcgtccagag gacgacacac    240
ggccggccgg tgaagtaaaa gggagtaatc ttattttgcc aggacgaggg gcggtacatg    300
atattacaca cgtaccatgc atgcatatat gcatggacaa ggtacgtcgt cgtcgatcga    360
cgtcgatgca tatgtgtgta tgtatgtacg tgcataatgc atggtaccag ctgctggctt    420
atatatattt gtcaccgatc gatgcatgct gctgctctac acggtttgac acttttaattt    480 gactcatcga tgaccttgct agatagtagc ggctcgtcaa ttaatgagcc atcaagttaa    540
caagagggca cgggcttgcg cgactgattc caccttatta acatacgccc tgcgcccgcg    600
cgtgctgtac gtacgagaat ttcgaattac attaattcaa agctgtgtat gtatgtatat    660
atatatgtgc gtttttttgt gtgtgtatgt ctctttgctt ggtctttctc tatcgatccc    720 cctcttttgat agtttaaact gaaggcggga acgacaatc tgatcatgag cggagaatta    780
agggagtcac gttatgaccc ccgccgatga cgcgggacaa gccgttttac gtttggaact    840
gacagaaccg caacgttgaa ggagccactc agcaagctgg gccccccctc gaggtcggcc    900
gcattcgcaa aacacaccta gactagattt gttttgctaa cccaattgat attaattata    960
tatgattaat atttatatgt atatggattt ggttaatgaa atgcatctgg ttcatcaaag    1020
aattataaag acacgtgaca ttcatttagg ataagaaata tggatgatct ctttctcttt    1080
tattcagata actagtaatt acacataaca cacaactttg atgcccacat tatagtgatt    1140
agcatgtcac tatgtgtgca tcctttttatt tcatacatta attaagttgg ccaatccaga    1200
```

```
agatggacaa gtctaggtta actgactagc tagtcagtac acagtcctgc catcaccatc    1260
caggatcata tccttgaaag ccccaccact agggatcata gcaacacat gctcctggtg     1320 tgggacgatt atatccaaga ggtacggccc tggagtctcg agcatcttct ttatcgctgc    1380
gcggacttcg ttcttctttg tcacacggac cgctggaatg ttgaaccctt ggcgatcgt    1440 cacgaaatct ggatatatct cactttcatt ctctgggttt cccaagtatg tgtgcgctct    1500
gttggcctta tagaacctgt cctccaactg caccaccatc cccaggtgct ggttgtttag    1560
cacaaagacc ttcactggga ggttctcaat tcggatcata gctagctcct gaacgttcat    1620
gagaaagcta ccatctccat cgatgtcaac aacagtgaca cctgggtttg ccacagaagc    1680
accagcagca gccggcaaac caaatcccat agccccaaga ccagctgaag caaccactg    1740 ccttggccgc ttgtaagtgt agtactgtgc cgcccacatc tggtgctgcc caacacctgt    1800
gccgatgatg gcctcgcctt tcgtcagctc atcaagaacc tgaatagcat attgtggctg    1860
gatctcctca ttagatgttt tatacccaag gggaattcc ctcttctgct gatccaactc     1920
atcgttccat gagccaaagt caaagctctt ctttgatgtg cttccttcaa gaagagcatt    1980
catgccctgc aaagcaagct taacatctgc acagatggac acatgtggct gcttgttctt    2040
gccaatctca gccggatcaa tatcaacgtg cacaatctta gccctgcttg caaaagcctc    2100
aatcttccct gtcacgcgat catcaaaccg cacaccaagt gcaagcaaca gatcggcctt    2160
atccactgca taatttgcat acaccgtccc atgcatacct agcatgcgca gagacagtgg    2220
gtcgtcgctg gggaagttgc cgaggcccat aagagtagtt gtgaccggga ttccagtcag    2280
ctccacaaag cgtcgcaact cctcaccaga tgctgcgcag ccaccgccca cataaagaac    2340
agggcgccgc gattcaccaa caagacgcag cacctgctca gcaactcag tcgcaggggg     2400 cttgggaagg cgcgcaatgt acccaggcag actcatgggc ttgtcccaga caggcaccgc    2460
catctgctgc tggatgtcct tggggatgtc gacaagcacc ggccctggtc gaccagagga    2520
ggcgaggaag aaagcctcct gcacgacgcg ggggatgtcg tcgacgtcga ggaccaggta    2580
gttgtgcttg gtgatggagc gggtgacctc gacgatgggc gtctcctgga aggcgtcggt    2640
gccaatcatg cgtcgcgcca cctgtcccgt gatggcgacc atggggacgg aatcgagcag    2700
cgcgtcggcg agcgcggaga ctaggttggt ggcgccgggg ccggaggtgg cgatgcagac    2760
gccgacgcgc cccgaggagc gcgcgtagcc ggaggcggca aaggcctccc cttgctcgtg    2820
gcggaagagg tggttggcga tgacggggga gcgggtgagt gcctggtgga tctccatgga    2880
cgcgccgccg gggtaggcga agacgtcgcg gacgccgcag cgctcgaggg actcgacgag    2940
gatgtcagca cccttgcggg gctcggtggg gccccacggc cggagcgggg tggccggggg    3000
agccatcggc atggcgggtg acgccgctga gcacctgatg ggcgcggcga gggcgcggcg    3060
ggtggccagg aggtgcgccc ggcgcctcgc cttgggcgca gcggtagtgg cgccagtgag    3120
cgcggtagac gcggcggcgg cggtggccat ggttgcggcg gctgtctcgg aggcggcgcg    3180
agggtttggg gtgggtgcca cggacacgga gtgggagaaa ggggatgtg cgtggaggcc     3240 tccctgcttt tgttcagagg atgtgtggct cagatggtga tgggaatggg actcgcaaga    3300
cgacgacgac acgtccgtcg cccgaatacg tacacgctac agaccggacg gtggggcctg    3360
tcgacgtggg accgacgtgt cggcctggat tacaaacgtg gtgtccaccg agtgctggta    3420
cacgacagcg tgcgtcaagg aggttttgaa ctgttccgtt aaaaaaagag gggagatttt    3480
ggacttgact gtggacgacg gtgcatgtca tcggagtaca gacggtactg acacaagggg    3540
cccagacaag ggaatccaaa cgggtcgcac ccacctgcca ggctgccacc cgcaatccgc    3600
```

```
aacagggaaa ccgggcacag cccacaacca caagatgagc agctgcggcg acagcgtcag    3660
gcccggtgtc ggtgttaggg atggcaccct ttggctcccc gtatccgtcc ccgcgacaaa    3720
aaaatttccc gcggggattc ccacgaactc ttgcgagaga catttcttcc ccatccccgt    3780
tccccacggg gataaatccc catcggggat cctctagagt cgacctgcag gcatgcaagc    3840
ttcggtccgc ggccagcttg ctaacccggg ccccccctcg aggtcatcac atcaatccac    3900
ttgctttgaa gacgtggttg gaacgtcttc tttttccacg atgctcctcg tgggtggggg    3960
tccatctttg ggaccactgt cggcagaggc atcttcaacg atggcctttc ctttatcgca    4020
atgatggcat ttgtaggagc caccttcctt ttccactatc ttcacaataa agtgacagat    4080
agctgggcaa tggaatccga ggaggtttcc ggatattacc ctttgttgaa aagtctcaat    4140
tgcccttttgg tcttctgaga ctgtatcttt gatattttttg gagtagacaa gcgtgtcgtg    4200
ctccaccatg ttgacgaaga ttttcttctt gtcattgagt cgtaagagac tctgtatgaa    4260
ctgttcgcca gtctttacgg cgagttctgt taggtcctct atttgaatct ttgactccat    4320
ggacggtatc gataagctag cttgatatca catcaatcca cttgctttga agacgtggtt    4380
ggaacgtctt ctttttccac gatgctcctc gtgggtgggg gtccatcttt gggaccactg    4440
tcggcagagg catcttcaac gatggccttt cctttatcgc aatgatggca tttgtaggag    4500
ccaccttcct tttccactat cttcacaata agtgacaga tagctgggca atggaatccg    4560
aggaggtttc cggatattac cctttgttga aaagtctcaa ttgcccttttg tcttctgag    4620
actgtatctt tgatatttttt ggagtagaca agcgtgtcgt gctccaccat gttgacgaag    4680
attttcttct tgtcattgag tcgtaagaga ctctgtatga actgttcgcc agtctttacg    4740
gcgagtctg ttaggtcctc tatttgaatc tttgactcca tgatcgaatt atcacatcaa    4800
tccacttgct ttgaagacgt ggttggaacg tcttcttttt ccacgatgct cctcgtgggt    4860
gggggtccat ctttgggacc actgtcggca gaggcatctt caacgatggc ctttcctttta    4920
tcgcaatgat ggcatttgta ggagccacct tcctttttcca ctatcttcac aataaagtga    4980
cagatagctg gcaatggaa tccgaggagg tttccggata ttaccctttg ttgaaaagtc    5040
tcaattgccc tttggtcttc tgagactgta tctttgatat ttttggagta gacaagcgtg    5100
tcgtgctcca ccatgttgac gaagattttc ttcttgtcat tgagtcgtaa gagactctgt    5160
atgaactgtt cgccagtctt tacggcgagt tctgttaggt cctctatttg aatctttgac    5220
tccatgggaa ttcctgcagc ccgggattag agcttgcat gcctgcagtg cagcgtgacc    5280
cggtcgtgcc cctctctaga gataatgagc attgcatgtc taagttataa aaaattacca    5340
catattttttt ttgtcacact tgtttgaagt gcagtttatc tatctttata catatattta    5400
aactttactc tacgaataat ataatctata gtactacaat aatatcagtg ttttagagaa    5460
tcatataaat gaacagttag acatggtcta aaggacaatt gagtattttg acaacaggac    5520
tctacagttt tatctttttta gtgtgcatgt gttctccttt tttttttgcaa atagcttcac    5580
ctatataata cttcatccat tttattagta catccattta gggtttaggg ttaatggttt    5640
ttatagacta attttttttag tacatctatt ttattctatt ttagcctcta aattaagaaa    5700
actaaaactc tatttttagtt tttttatttta ataatttaga tataaaatag aataaaataa    5760
agtgactaaa aattaaacaa atacccttta agaaattaaa aaaactaagg aaacatttttt    5820
cttgttttcga gtagataatg ccagcctgtt aaacgccgtc gacgagtcta acggacacca    5880
accagcgaac cagcagcgtc gcgtcgggcc aagcgaagca gacggcacgg catctctgtc    5940
gctgcctctg gaccctctc gagagttccg ctccaccgtt ggacttgctc cgctgtcggc    6000
```

```
atccagaaat tgcgtggcgg agcggcagac gtgagccggc acggcaggcg gcctcctcct   6060
cctctcacgg caccggcagc tacgggggat tcctttccca ccgctccttc gctttccctt   6120
cctcgcccgc cgtaataaat agacaccccc tccacaccct ctttccccaa cctcgtgttg   6180
ttcggagcgc acacacacac aaccagatct cccccaaatc cacccgtcgg cacctccgct   6240
tcaaggtacg ccgctcgtcc tccccccccc ccctctctac cttctctaga tcggcgttcc   6300
ggtccatggt tagggcccgg tagttctact tctgttcatg tttgtgttag atccgtgttt   6360
gtgttagatc cgtgctgcta gcgttcgtac acggatgcga cctgtacgtc agacacgttc   6420
tgattgctaa cttgccagtg tttctctttg gggaatcctg ggatggctct agccgttccg   6480
cagacgggat cgatttcatg attttttttg tttcgttgca tagggtttgg tttgcccttt   6540
tcctttattt caatatatgc cgtgcacttg tttgtcgggt catcttttca tgcttttttt   6600
tgtcttggtt gtgatgatgt ggtctggttg ggcggtcgtt ctagatcgga gtagaattct   6660
gtttcaaact acctggtgga tttattaatt ttggatctgt atgtgtgtgc catacatatt   6720
catagttacg aattgaagat gatggatgga aatatcgatc taggataggt atacatgttg   6780
atgcgggttt tactgatgca tatacagaga tgctttttgt tcgcttggtt gtgatgatgt   6840
ggtgtggttg ggcggtcgtt cattcgttct agatcggagt agaatactgt ttcaaactac   6900
ctggtgtatt tattaattt ggaactgtat gtgtgtgtca tacatcttca tagttacgag   6960
tttaagatgg atggaaatat cgatctagga taggtataca tgttgatgtg ggttttactg   7020
atgcatatac atgatggcat atgcagcatc tattcatatg ctctaacctt gagtacctat   7080
ctattataat aaacaagtat gttttataat tattttgatc ttgatatact tggatgatgg   7140
catatgcagc agctatatgt ggattttttt agccctgcct tcatacgcta tttatttgct   7200
tggtactgtt tcttttgtcg atgctcaccc tgttgtttgg tgttacttct gcaggtcgac   7260
cgccggggat ccacacgaca ccatggctat tgaggttaag cctatcaacg cagaggatac   7320
ctatgacctt aggcatagag tgctcagacc aaaccagcct atcgaagcct gcatgtttga   7380
gtctgacctt actaggagtg catttcacct tggtggattc tacggaggta aactgatttc   7440
cgtggcttca ttccaccaag ctgagcactc tgaacttcaa ggtaagaagc agtaccagct   7500
tagaggtgtg gctaccttgg aaggttatag agagcagaag gctggttcca gtctcgtgaa   7560
acacgctgaa gagattctca gaaagagagg tgctgacatg atctggtgta atgccaggac   7620
atctgcttca ggatactaca ggaagttggg attcagtgag caaggagagg tgttcgatac   7680
tcctccagtt ggacctcaca tcctgatgta taagaggatc acataactag ctagtcagtt   7740
aacctagact tgtccatctt ctggattggc caacttaatt aatgtatgaa ataaaaggat   7800
gcacacatag tgcatgcta atcactataa tgtgggcatc aaagtgtgt gttatgtgta   7860
attactagtt atctgaataa aagagaaaga gatcatccat atttcttatc ctaaatgaat   7920
gtcacgtgtc tttataattc tttgatgaac cagatgcatt tcattaacca aatccatata   7980
catataaata ttaatcatat ataattaata tcaattgggt tagcaaaaca aatctagtct   8040
aggtgtgttt tgcgaattca gtacattaaa aacgtccgca atgtgttatt aagttgtcta   8100
agcgtcaatt tg                                                       8112
```

<210> SEQ ID NO 51
<211> LENGTH: 25
<212> TYPE: DNA
<213> ORGANISM: Artificial Sequence
<220> FEATURE:
<223> OTHER INFORMATION: Primer DP098-3'-f12

```
<400> SEQUENCE: 51
tgcgaattca gtacattaaa aacgt                                          25

<210> SEQ ID NO 52
<211> LENGTH: 25
<212> TYPE: DNA
<213> ORGANISM: Artificial Sequence
<220> FEATURE:
<223> OTHER INFORMATION: Primer DP098-3'-r12

<400> SEQUENCE: 52 tgttttttt ctaggaaagc tggtt                                           25

<210> SEQ ID NO 53
<211> LENGTH: 32
<212> TYPE: DNA
<213> ORGANISM: Artificial Sequence
<220> FEATURE:
<223> OTHER INFORMATION: Primer DP098-3'-p6
<220> FEATURE:
<221> NAME/KEY: misc_feature
<222> LOCATION: (1)...(1)
<223> OTHER INFORMATION: nucleotide at position 1 is modified to have a
      FAM fluorophore
<220> FEATURE:
<221> NAME/KEY: misc_feature
<222> LOCATION: (32)...(32)
<223> OTHER INFORMATION: Nucleotide at position 32 is modified to have a
      TAMRA fluorophore.

<400> SEQUENCE: 53
ccgcaatgtg ttattaagtt gtctaagcgt ca                                  32

<210> SEQ ID NO 54
<211> LENGTH: 26
<212> TYPE: DNA
<213> ORGANISM: Artificial Sequence
<220> FEATURE:
<223> OTHER INFORMATION: Primer DP098-f6

<400> SEQUENCE: 54
gtgtgtatgt ctctttgctt ggtctt                                         26

<210> SEQ ID NO 55
<211> LENGTH: 20
<212> TYPE: DNA
<213> ORGANISM: Artificial Sequence
<220> FEATURE:
<223> OTHER INFORMATION: Primer DP098-r2

<400> SEQUENCE: 55
gattgtcgtt tcccgccttc                                                20

<210> SEQ ID NO 56
<211> LENGTH: 33
<212> TYPE: DNA
<213> ORGANISM: Artificial Sequence
<220> FEATURE:
<223> OTHER INFORMATION: DP098-p5
<220> FEATURE:
<221> NAME/KEY: misc_feature
<222> LOCATION: (1)...(1)
<223> OTHER INFORMATION: nucleotide at position 1 is modified to have a
      FAM fluorophore
<220> FEATURE:
<221> NAME/KEY: misc_feature
<222> LOCATION: (33)...(33)
<223> OTHER INFORMATION: Nucleotide at position 33 is modified to have a
      TAMRA fluorophore.
```

-continued

```
<400> SEQUENCE: 56
ctctatcgat cccctctttt gatagtttaa act                                  33

<210> SEQ ID NO 57
<211> LENGTH: 931
<212> TYPE: DNA
<213> ORGANISM: Artificial Sequence
<220> FEATURE:
<223> OTHER INFORMATION: Zm-HRA 3' probe (ud#2)

<400> SEQUENCE: 57
tcagtacaca gtcctgccat caccatccag gatcatatcc ttgaaagccc caccactagg     60
gatcataggc aacacatgct cctggtgtgg gacgattata tccaagaggt acggccctgg    120
agtctcgagc atcttcttta tcgctgcgcg gacttcgttc ttctttgtca cacgaccgc     180 tggaatgttg aaccctttgg cgatcgtcac gaaatctgga tatatctcac tttcattctc    240
tgggtttccc aagtatgtgt gcgctctgtt ggccttatag aacctgtcct ccaactgcac    300
caccatcccc aggtgctggt tgtttagcac aaagaccttc actgggaggt tctcaattcg    360
gatcatagct agctcctgaa cgttcatgag aaagctacca tctccatcga tgtcaacaac    420
agtgacacct gggtttgcca cagaagcacc agcagcagcc ggcaaaccaa atcccatagc    480
cccaagacca gctgaagaca accactgcct tggccgcttg taagtgtagt actgtgccgc    540
ccacatctgg tgctgcccaa cacctgtgcc gatgatggcc tcgcctttcg tcagctcatc    600
aagaacctga atagcatatt gtggctggat ctcctcatta gatgttttat acccaagggg    660
gaattccctc ttctgctgat ccaactcatc gttccatgag ccaaagtcaa agctcttctt    720
tgatgtgctt ccttcaagaa gagcattcat gccctgcaaa gcaagcttaa catctgcaca    780
gatggacaca tgtggctgct tgttcttgcc aatctcagcc ggatcaatat caacgtgcac    840
aatcttagcc ctgcttgcaa aagcctcaat cttccctgtc acgcgatcat caaaccgcac    900
accaagtgca agcaacagat cggccttatc c                                   931
```

MAIZE EVENT DP-098140-6 AND COMPOSITIONS AND METHODS FOR THE IDENTIFICATION AND/OR DETECTION THEREOF

CROSS-REFERENCE TO RELATED APPLICATIONS

This application claims the benefit of U.S. Provisional Application No. 60/940,567, filed May 29, 2007 and U.S. Provisional Application No. 60/855,308, filed Oct. 30, 2006, each of which are herein incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 334449 SEQLIST.txt, a creation date of Oct. 9, 2007, and a size of 100 Kb. The sequence listing filed via EFS-Web is part of the specification and is hereby incorporated in its entirety by reference herein.

FIELD OF THE INVENTION

This invention is in the field of molecular biology. More specifically, this invention pertains to multiple herbicide tolerances conferred by expression of a sequence that confers tolerance to glyphosate in conjunction with the expression of sequence that confers tolerance to one or more ALS inhibitor chemistries.

BACKGROUND OF THE INVENTION

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al. (1988) *Ann. Rev. Genet.* 22: 421-477, 1988). At the same time the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. It is also observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, or for use in environmental monitoring, monitoring traits in crops in the field, or monitoring products derived from a crop harvest, as well as, for use in ensuring compliance of parties subject to regulatory or contractual terms.

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system would involve the use of crop plants which are tolerant to an herbicide so that when the herbicide was sprayed on a field of herbicide-tolerant crop plants, the crop plants would continue to thrive while non-herbicide-tolerant weeds were killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

Due to local and regional variation in dominant weed species as well as preferred crop species, a continuing need exists for customized systems of crop protection and weed management which can be adapted to the needs of a particular region, geography, and/or locality. Method and compositions that allow for the rapid identification of events in plants that produce such qualities are needed. For example, a continuing need exists for methods of crop protection and weed management which can reduce: the number of herbicide applications necessary to control weeds in a field; the amount of herbicide necessary to control weeds in a field; the amount of tilling necessary to produce a crop; and/or programs which delay or prevent the development and/or appearance of herbicide-resistant weeds. A continuing need exists for methods and compositions of crop protection and weed management which allow the targeted use of particular herbicide combinations and for the efficient detection of such an event.

BRIEF SUMMARY OF THE INVENTION

Compositions and methods related to transgenic glyphosate/ALS inhibitor-tolerant maize plants are provided. Specifically, the present invention provides maize plants containing the DP-098140-6 event which imparts tolerance to glyphosate and at least one ALS-inhibiting herbicide. The maize plant harboring the DP-098140-6 event at the recited chromosomal location comprises genomic/transgene junctions having at least the polynucleotide sequence of SEQ ID NO: 5 and/or 6. Further provided are the seeds deposited as Patent Deposit No. PTA-8296 and plants, plant cells, plant parts, grain and plant products derived therefrom. The characterization of the genomic insertion site of event DP-098140-6 provides for an enhanced breeding efficiency and enables the use of molecular markers to track the transgene insert in the breeding populations and progeny thereof. Various methods and compositions for the identification, detection, and use of the maize event DP-098140-6 are provided.

DETAILED DESCRIPTION OF THE INVENTION

Figure 1:
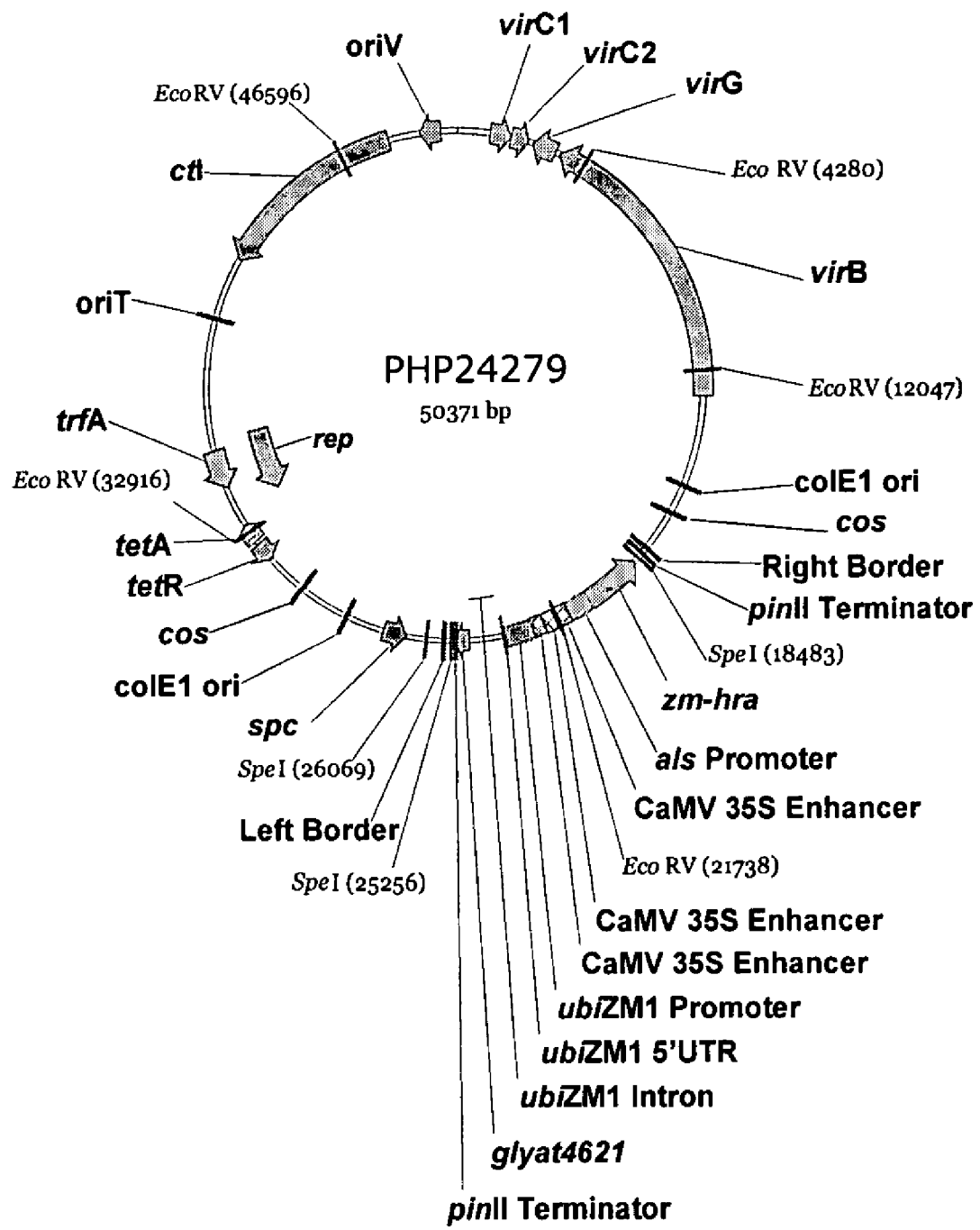
FIG. 1 shows the plasmid map of PHP24279. Plasmid PHP24279 was used to produce the DP-098140-6 maize line.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods related to transgenic glyphosate/ALS inhibitor-tolerant maize plants are provided. Specifically, the present invention provides maize plants having event DP-098140-6. The DP-098140-6 is also known as event E6631.98.40 or event 98140. A maize plant having "event DP-098140-6" has been modified by the insertion of the glyphosate acetyltransferase (glyat4621) gene derived from Bacillus licheniformis and a modified version of the maize acetolactate synthase gene (zm-hra). The glyat4621 gene was functionally improved by a gene shuffling process to optimize the kinetics of glyphosate acetyltransferase (GLYAT) activity for acetylating the herbicide glyphosate. The insertion of the glyat4621 gene in the plant confers tolerance to the herbicidal active ingredient glyphosate through the conversion of glyphosate to the non-toxic acetylated form. The insertion of the zm-hra gene produces a modified form of the acetolactate synthase (ALS) enzyme. ALS is essential for branched chain amino acid biosynthesis and is inhibited by certain herbicides. The modification in the zm-hra gene overcomes this inhibition and thus provides tolerance to a wide range of ALS-inhibiting herbicides. Thus, a maize plant having the event DP-098140-6 is tolerant to glyphosate and at least one ALS-inhibiting herbicide.

The polynucleotides conferring the glyphosate and ALS inhibitor tolerance are linked on the same DNA construct and are inserted at a characterized position in the maize genome and thereby produce the DP-098140-6 maize event. The maize plant harboring the DP-098140-6 event at the recited chromosomal location comprises genomic/transgene junctions having at least the polynucleotide sequence of SEQ ID NO: 5 and/or 6. The characterization of the genomic insertion site of the DP-098140-6 event provides for an enhanced breeding efficiency and enables the use of molecular markers to track the transgene insert in the breeding populations and progeny thereof. Various methods and compositions for the identification, detection, and use of the maize DP-098140-6 event are provided herein. As used herein, the term "event DP-098140-6 specific" refers to a polynucleotide sequence which is suitable for discriminatively identifying event DP-098140-6 in plants, plant material, or in products such as, but not limited to, food or feed products (fresh or processed) comprising, or derived from plant material.

Compositions further include seed deposited as Patent Deposit Nos. PTA-8296 and plants, plant cells, and seed derived therefrom. Applicant(s) have made a deposit of at least 2500 seeds of maize event DP-098140-6 with the American Type Culture Collection (ATCC), Manassas, Va. 20110-2209 USA, on Mar. 28, 2007, and the deposits were assigned ATCC Deposit No. PTA-8296. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112. The seeds deposited with the ATCC on Mar. 28, 2007 were taken from the deposit maintained by Pioneer Hi-Bred International, Inc., 7250 NW 62$^{nd}$ Avenue, Johnston, Iowa 50131-1000. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit of at least 2500 seeds of hybrid maize 38N86 with the American Type Culture Collection (ATCC), 10801 University Boulevard, Manassas, Va. 20110-2209. This deposit of seed of maize event DP-098140-6 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have satisfied all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event DP-098140-6 under the Plant Variety Protection Act (7 USC 2321 et seq.). Unauthorized seed multiplication prohibited. The seed may be regulated.

As used herein, the term "maize" means any maize plant and includes all plant varieties that can be bred with maize. As used herein, the term plant includes plant cells, plant organs, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise a DP-098140-6 event.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene(s). At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule. Non-limiting examples of the flanking regions of the DP-098140-6 event comprise polynucleotide sequences that are set forth in SEQ ID NO: 1, 2, and 46 and variants and fragments thereof.

Transformation procedures leading to random integration of the foreign DNA will result in transformants containing different flanking regions characteristic of and unique for each transformant. When recombinant DNA is introduced into a plant through traditional crossing, its flanking regions will generally not be changed. Transformants will also contain unique junctions between a piece of heterologous insert DNA and genomic DNA, or two pieces of genomic DNA, or two pieces of heterologous DNA. A "junction" is a point where two specific DNA fragments join. For example, a junction exists where insert DNA joins flanking DNA. A junction point also exists in a transformed organism where two DNA fragments join together in a manner that is modified from that found in the native organism. As used herein, "junction DNA" refers to DNA that comprises a junction point. Non-limiting examples of junction DNA from the DP-098140-6 event set are set forth in SEQ ID NO: 4, 5, 6, 7, 8, 9, 10, 11, 12, 48, 49, or 50 or variants and fragments thereof.

A DP-098140-6 plant can be bred by first sexually crossing a first parental maize plant grown from the transgenic DP-098140-6 maize plant (or progeny thereof derived from transformation with the expression cassettes of the embodiments of the present invention that confer herbicide tolerance) and a second parental maize plant that lacks the herbicide tolerance phenotype, thereby producing a plurality of first progeny plants; and then selecting a first progeny plant that displays the desired herbicide tolerance; and selfing the first progeny plant, thereby producing a plurality of second progeny plants; and then selecting from the second progeny plants which display the desired herbicide tolerance. These steps can further include the back-crossing of the first herbicide tolerant progeny plant or the second herbicide tolerant progeny plant to the second parental maize plant or a third parental maize plant, thereby producing a maize plant that displays the desired herbicide tolerance. It is further recognized that assaying progeny for phenotype is not required. Various methods and compositions, as disclosed elsewhere herein, can be used to detect and/or identify the DP-098140-6 event.

Two different transgenic plants can also be sexually crossed to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos J. ed., American Society of Agronomy, Madison Wis. (1987).

The term "germplasm" refers to an individual, a group of individuals, or a clone representing a genotype, variety, species or culture, or the genetic material thereof.

A "line" or "strain" is a group of individuals of identical parentage that are generally inbred to some degree and that are generally isogenic or near isogenic.

Inbred maize lines are typically developed for use in the production of maize hybrids and for use as germplasm in breeding populations for the creation of new and distinct inbred maize lines. Inbred maize lines are often used as targets for the introgression of novel traits through traditional breeding and/or molecular introgression techniques. Inbred maize lines need to be highly homogeneous, homozygous and reproducible to be useful as parents of commercial hybrids. Many analytical methods are available to determine the homozygosity and phenotypic stability of inbred lines.

The phrase "hybrid plants" refers to plants which result from a cross between genetically different individuals.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and, ovule are from the same plant).

The term "introgression" refers to the transmission of a desired allele of a genetic locus from one genetic background to another. In one method, the desired alleles can be introgressed through a sexual cross between two parents, wherein at least one of the parents has the desired allele in its genome.

In some embodiments, the polynucleotide conferring the maize DP-098140-6 event of the invention are engineered into a molecular stack. In other embodiments, the molecular stack further comprises at least one additional polynucleotide that confers tolerance to a 3$^{rd}$ herbicide. In one embodiment, the sequence confers tolerance to glufosinate, and in a specific embodiment, the sequence comprises pat gene.

In other embodiments, the maize DP-098140-6 event of the invention comprise one or more traits of interest, and in more specific embodiments, the plant is stacked with any combination of polynucleotide sequences of interest in order to create plants with a desired combination of traits. A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) *Gene* 48: 109; Lee et al. (2003) *Appl. Environ. Microbiol.* 69: 4648-4657 Vip3A); Galitzky et al. (2001) *Acta Crystallogr. D. Biol. Crystallogr.* 57: 1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In some embodiments, maize DP-098140-6 event may be stacked with other herbicide-tolerance traits to create a transgenic plant of the invention with further improved properties. Other herbicide-tolerance polynucleotides that could be used in such embodiments include those conferring tolerance to glyphosate or to ALS inhibitors by other modes of action, such as, for example, a gene that encodes a glyphosate oxidoreductase enzyme as described more fully in U.S. Pat. Nos. 5,776,760 and 5,463,175. Other traits that could be combined with the maize DP-098140-6 events include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747. Other traits that could be combined with the maize DP-098140-6 event include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

In some embodiments, the maize DP-098140-6 event may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268,549; and 6,069,115; and international publication WO 99/23886. Other examples of suitable herbicide-tolerance traits that could be stacked with the maize DP-098140-6 event include aryloxyalkanoate dioxygenase polynucleotides (which reportedly confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767.

Other examples of herbicide-tolerance traits that could be combined with the maize DP-098140-6 event include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the maize DP-098140-6 event include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with the maize DP-098140-6 event include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with the maize DP-098140-6 event to provide a plant of the invention as well as methods of use thereof.

The maize DP-098140-6 event can also be combined with at least one other trait to produce plants of the present invention that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

The maize DP-098140-6 event can also be combined with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In another embodiment, the maize DP-098140-6 event can also be combined with the Rcg1 sequence or biologically active variant or fragment thereof. The Rcg1 sequence is an anthracnose stalk rot resistance gene in corn. See, for example, U.S. patent application Ser. Nos. 11/397,153, 11/397,275, and 11/397,247, each of which is herein incorporated by reference.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

As used herein, the use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

A DP-098140-6 plant comprises an expression cassette having a glyphosate acetyltransferase polynucleotide and a genetically modified acetolactate synthase gene (zm-hra). The cassette can include 5' and 3' regulatory sequences operably linked to the glyat and the zm-hra polynucleotides. "Operably linked" is intended to mean a functional linkage between two or more elements. For example, an operable linkage between a polynucleotide of interest and a regulatory sequence (i.e., a promoter) is functional link that allows for the expression of the polynucleotide of interest. Operably linked elements may be contiguous or non-contiguous. When used to refer to the joining of two protein coding regions, by operably linked it is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a coding region, and a transcriptional and translational termination region functional in plants. "Promoter" refers to a nucleotide sequence capable of controlling the expression of a coding sequence or functional RNA. In general, a coding sequence is located 3' to a promoter sequence. The promoter sequence can comprise proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15: 1-82. It is further recognized that since in most cases the exact boundaries of regulatory sequences have not been completely defined, nucleic acid fragments of different lengths may have identical promoter activity.

The expression cassettes may also contain 5' leader sequences. Such leader sequences can act to enhance translation. The regulatory regions (i.e., promoters, transcriptional regulatory regions, RNA processing or stability regions, introns, polyadenylation signals, transcriptional termination regions, and translational termination regions) and/or the coding region may be native/analogous or heterologous to the host cell or to each other.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3: 225-236). The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The use of different 3' non-coding sequences is exemplified by Ingelbrecht et al. (1989) *Plant Cell* 1: 671-680.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. The expression cassette can also comprise a selectable marker gene for the selection of transformed cells. Selectable marker genes are utilized for the selection of transformed cells or tissues.

Isolated polynucleotides are provided that can be used in various methods for the detection and/or identification of the maize DP-098140-6 event. An "isolated" or "purified" polynucleotide, or biologically active portion thereof, is substantially or essentially free from components that normally accompany or interact with the polynucleotide as found in its naturally occurring environment. Thus, an isolated or purified polynucleotide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

In specific embodiments, the polynucleotides of the invention comprise the junction DNA sequence set forth in SEQ ID NO: 5 or 6. In other embodiments, the polynucleotides of the invention comprise the junction DNA sequences set forth in SEQ ID NO: 4, 5, 6, 7, 8, 9, 10, 11, 12, 48, 49, or 50 or variants and fragments thereof. In specific embodiments, methods of detection described herein amplify a polynucleotide comprising the junction of the DP-098140-6 specific event. Fragments and variants of junction DNA sequences are suitable for discriminatively identifying event DP-098140-6. As discussed elsewhere herein, such sequences find use as primers and/or probes.

In other embodiments, the polynucleotides of the invention comprise polynucleotides that can detect a DP-098140-6 event or a DP-098140-6 specific region. Such sequences include any polynucleotide set forth in SEQ ID NOS: 1, 2, 3, 4, 5, 6, 7, 8, 9, 10, 11, 12, 13, 14, 15, 16, 17, 18, 19, 20, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 or variants and fragments thereof. Fragments and variants of polynucleotides that detect a DP-098140-6 event or a DP-098140-6 specific region are suitable for discriminatively identifying event DP-098140-6. As discussed elsewhere herein, such sequences find use as primers and/or probes. Further provided are isolated DNA nucleotide primer sequences comprising or consisting of a sequence set forth in SEQ ID NO: 13, 14, 15, 16, 17, 18, 19, 20, 23, 25, 26, 27, 28, 29, 30, 31, 32, 33, 34, 35, 36, 37, 38, 39, 40, 41, 42, 43, 44, 45, 51, 52, 53, 54, 55, 56, or a complement thereof.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, in the case of the present invention, to a strand of isolated DNA from maize event DP-098140-6 whether from a maize plant or from a sample that includes DNA from the event. Probes according to the present invention include not only deoxyribonucleic or ribonucleic acids but also polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference). Any combination of primers (i.e., SEQ ID NO: 13, 14, 15, 16, 17, 18, 19, 20, 21, 25, 26, 27, 28, 29, 30, 31, 32, 34, 35, 36, 37, 38, 39, 40, 41, 42, 43, 44, 45, 51, 52, 53, 54, 55, or 56) disclosed herein can be used such that the pair allows for the detection of a DP-098140-6 event or specific region. Non-limiting examples of primer pairs include SEQ ID NOS: 13 and 14; SEQ ID NOS: 15 and 16; SEQ ID NOS: 17 and 18; SEQ ID NO: 20 and 21; SEQ ID NO:51 and 52; and, SEQ ID NO:54 and 55.

Probes and primers are of sufficient nucleotide length to bind to the target DNA sequence and specifically detect and/or identify a polynucleotide having a DP-098140-6 event. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length are used. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide (i.e., SEQ ID NO: 1-57), or can differ from the target sequence (i.e., SEQ ID NO: 1-57) by 1, 2, 3, 4, 5, 6 or more nucleotides. Probes can be used as primers, but are generally designed to bind to the target DNA or RNA and are not used in an amplification process. In one non-limiting embodiment, a probe can comprises a polynucleotide encoding the glyat4621 or the zm-hra sequence or any variant or fragment of these sequences.

Specific primers can be used to amplify an integration fragment to produce an amplicon that can be used as a "specific probe" or can itself be detected for identifying event DP-098140-6 in biological samples. Alternatively, a probe of the invention can be used during the PCR reaction to allow for the detection of the amplification event (i.e., a Taqman™ probe or an MGB probe, so called real-time PCR). When the probe is hybridized with the polynucleotides of a biological sample under conditions which allow for the binding of the probe to the sample, this binding can be detected and thus allow for an indication of the presence of event DP-098140-6 in the biological sample. Such identification of a bound probe has been described in the art. In an embodiment of the invention, the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the DP-098140-6 event.

Figure 2:
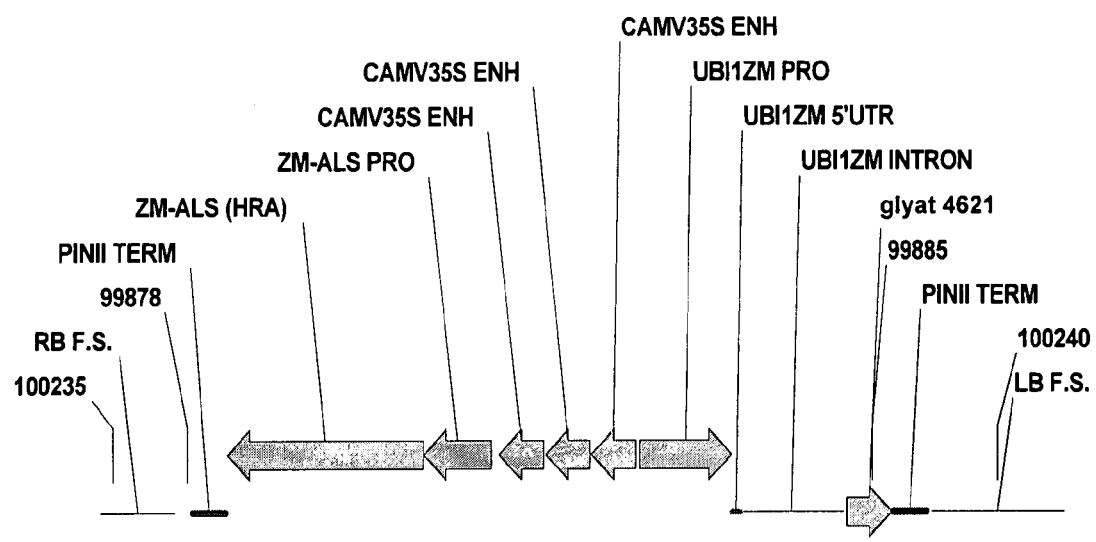
FIG. 2 provides a schematic map of the T-DNA from Plasmid PHP24279 showing various genetic elements with additional flanking border sequence. RB denotes the right flanking border sequence and LB denotes the left flanking border sequence. The location of primers 100235, 99878, 99885, and 100240 are shown.

As used herein, "amplified DNA" or "amplicon" refers to the product of polynucleotide amplification of a target polynucleotide that is part of a nucleic acid template. For example, to determine whether a maize plant resulting from a sexual cross contains the DP-098140-6 event, DNA extracted from the maize plant tissue sample may be subjected to a polynucleotide amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the DP-098140-6 event DNA. In specific embodiments, the amplicon comprises a DP-098140-6 junction polynucleotide (i.e., SEQ ID NO: 4, 5, 6, 7, 8, 9, 10, 11, 12, 48, 49, or 50). By "diagnostic" for a DP-098140-6 event the use of any method or assay which discriminates between the presence or the absence of a DP-098140-6 event in a biological sample is intended. Alternatively, the second primer may be derived from the flanking sequence. In still other embodiments, primer pairs can be derived from flanking sequence on both sides of the inserted DNA so as to produce an amplicon that includes the entire insert polynucleotide of the expression construct as well as the sequence flanking the transgenic insert. See, FIG. 2. The amplicon is of a length and has a sequence that is also diagnostic for the event (i.e., has a junction DNA from a DP-098140-6 event). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Methods for preparing and using probes and primers are described, for example, in *Molecular Cloning: A Laboratory Manual,* 2.sup.nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5©, 1991, Whitehead Institute for Biomedical Research, Cambridge, Mass.). Additionally, the sequence can be visually scanned and primers manually identified using guidelines known to one of skill in the art.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143: 277) and particle-accelerated or "gene gun" transformation technology (Klein et al. (1987) *Nature* (London) 327: 70-73; U.S. Pat. No. 4,945,050, incorporated herein by reference). Additional transformation methods are disclosed below.

Thus, isolated polynucleotides of the invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. (1985; Supp. 1987) *Cloning Vectors: A Laboratory Manual*, Weissbach and Weissbach (1989) *Methods for Plant Molecular Biology* (Academic Press, New York); and Flevin et al. (1990) *Plant Molecular Biology Manual* (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Various methods and compositions for identifying event DP-098140-6 are provided. Such methods find use in identifying and/or detecting a DP-098140-6 event in any biological material. Such methods include, for example, methods to confirm seed purity and methods for screening seeds in a seed lot for a DP-098140-6 event. In one embodiment, a method for identifying event DP-098140-6 in a biological sample is provided and comprises contacting the sample with a first and a second primer; and, amplifying a polynucleotide comprising a DP-098140-6 specific region.

A biological sample can comprise any sample in which one desires to determine if DNA having event DP-098140-6 is present. For example, a biological sample can comprise any plant material or material comprising or derived from a plant material such as, but not limited to, food or feed products. As used herein, "plant material" refers to material which is obtained or derived from a plant or plant part. In specific embodiments, the biological sample comprises a maize tissue.

Primers and probes based on the flanking DNA and insert sequences disclosed herein can be used to confirm (and, if necessary, to correct) the disclosed sequences by conventional methods, e.g., by re-cloning and sequencing such sequences. The polynucleotide probes and primers of the present invention specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a DP-098140-6 specific region or the polynucleotide can be used as a probe that hybridizes under stringent conditions to a polynucleotide from a DP-098140-6 event. The level or degree of hybridization which allows for the specific detection of a DP-098140-6 event or a specific region of a DP-098140-6 event is sufficient to distinguish the polynucleotide with the DP-098140-6 specific region from a polynucleotide lacking this region and thereby allow for discriminately identifying a DP-098140-6 event. By "shares sufficient sequence identity or complementarity to allow for the amplification of a DP-098140-6 specific event" is intended the sequence shares at least 80%, 85%, 90%, 91%, 92%, 93%, 94%, 95%, 96%, 97%, 98%, 99% or 100% identity or complementarity to a fragment or across the full length of the polynucleotide from the DP-098140-6 specific region.

Regarding the amplification of a target polynucleotide (e.g., by PCR) using a particular amplification primer pair, "stringent conditions" are conditions that permit the primer pair to hybridize to the target polynucleotide to which one primer having the corresponding wild-type sequence (or its complement) and another primer having the corresponding DP-098140-6 inserted DNA sequence would bind and preferably to produce an identifiable amplification product (the amplicon) having a DP-098140-6 specific region in a DNA thermal amplification reaction. In a PCR approach, oligonucleotide primers can be designed for use in PCR reactions to amplify a DP-098140-6 specific region. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Methods of amplification are further described in U.S. Pat. Nos. 4,683,195, 4,683, 202 and Chen et al. (1994) *PNAS* 91:5695-5699. These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the DP-098140-6 event or a DP-098140-6 specific region. For example, the amplicon can be about 10, 50, 100, 200, 300, 500, 700, 100, 2000, 3000, 4000, 5000 nucleotides in length or longer.

In specific embodiments, the specific region of the DP-098140-6 event is detected.

Any primer can be employed in the methods of the invention that allows a DP-098140-6 specific region to be amplified and/or detected. For example, in specific embodiments, the first primer comprises a fragment of a polynucleotide of SEQ ID NO: 1, 2, or 46, wherein the first or the second primer shares sufficient sequence identity or complementarity to the polynucleotide to amplify the DP-098140-6 specific region. The primer pair can comprise a fragment of SEQ ID NO: 1 and a fragment of SEQ ID NO: 2, 3, 46, or 47; or alternatively, the primer pair can comprise a fragment of SEQ ID NO: 2 or 46 and a fragment of SEQ ID NO: 3, 47, or 1. In still further embodiments, the first and the second primer can comprise any one or any combination of the sequences set forth in SEQ ID NO: 13, 14, 15, 16, 17, 18, 19, 20, 21, 25, 26, 27, 28, 29, 30, 34, 35, 36, 37, 38, 39, 40, 41, 42, 43, 44, 45, 51, 52, 53, 54, 55, or 56. The primers can be of any length sufficient to amplify a DP-098140-6 specific region including, for example, at least 6, 7, 8, 9, 10, 15, 20, 15, or 30 or about 7-10, 10-15, 15-20, 20-25, 25-30, 30-35, 35-40, 40-45 nucleotides or longer.

As discussed elsewhere herein, any method to PCR amplify the DP-098140-6 event or specific region can be employed, including for example, real time PCR. See, for example, Livak et al. (1995a) Oligonucleotides with fluorescent dyes at opposite ends provide a quenched probe system for detecting PCR product and nucleic acid hybridization. PCR methods and Applications. 4:357-362; U.S. Pat. No. 5,538,848; U.S. Pat. No. 5,723,591; Applied Biosystems User Bulletin No. 2, "Relative Quantitation of Gene Expression," P/N 4303859; and, Applied Biosystems User Bulletin No. 5, "Multiplex PCR with Taqman VIC probes," P/N 4306236; each of which is herein incorporated by reference.

Thus, in specific embodiments, a method of detecting the presence of maize event DP-098140-6 or progeny thereof in a biological sample is provided. The method comprises (a) extracting a DNA sample from the biological sample; (b) providing a pair of DNA primer molecules, including, but not limited to, any combination of sequences in SEQ ID NO: 13-21, 25-30, 34-45, 51-56, including for example, i) the sequences of SEQ ID NO:13 and SEQ ID NO:14, ii) the sequences of SEQ ID NO:15 and SEQ ID NO:16; iii) the sequences of SEQ ID NO:17 and SEQ ID NO:18; iv) the sequences of SEQ ID NO: 20 and 21; (v) the sequences of SEQ ID NO:51 and 52; and, (vi) SEQ ID NO:54 and 55; (c) providing DNA amplification reaction conditions; (d) performing the DNA amplification reaction, thereby producing a DNA amplicon molecule; and (e) detecting the DNA amplicon molecule, wherein the detection of said DNA amplicon molecule in the DNA amplification reaction indicates the presence of maize event DP-098140-6. In order for a nucleic acid molecule to serve as a primer or probe it needs only be sufficiently complementary in sequence to be able to form a stable double-stranded structure under the particular solvent and salt concentrations employed.

In hybridization techniques, all or part of a polynucleotide that selectively hybridizes to a target polynucleotide having a DP-098140-6 specific event is employed. By "stringent conditions" or "stringent hybridization conditions" when referring to a polynucleotide probe conditions under which a probe will hybridize to its target sequence to a detectably greater degree than to other sequences (e.g., at least 2-fold over background) are intended. Regarding the amplification of a target polynucleotide (e.g., by PCR) using a particular amplification primer pair, "stringent conditions" are conditions that permit the primer pair to hybridize to the target polynucleotide to which one primer having the corresponding wild-type sequence and another primer having the corresponding DP-098140-6 inserted DNA sequence. Stringent conditions are sequence-dependent and will be variable in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138: 267-284: $T_m=81.5° C.+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.) and Haymes et al. (1985) In: *Nucleic Acid Hybridization, a Practical Approach*, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Further provided are methods of detecting the presence of DNA corresponding to the DP-098140-6 event in a sample. In one embodiment, the method comprises (a) contacting the biological sample with a polynucleotide probe that hybridizes under stringent hybridization conditions with DNA from maize event DP-098140-6 and specifically detects the DP-098140-6 event; (b) subjecting the sample and probe to stringent hybridization conditions; and (c) detecting hybridization of the probe to the DNA, wherein detection of hybridization indicates the presence of the DP-098140-6 event.

Various methods can be used to detect the DP-098140-6 specific region or amplicon thereof, including, but not limited to, Genetic Bit Analysis (Nikiforov et al. (1994) *Nucleic Acid Res.* 22: 4167-4175) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be annealed to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge ((2000) *Innov. Pharma. Tech.* 00: 18-24). In this method, an oligonucleotide is designed that overlaps the adjacent DNA and insert DNA junction. The oligonucleotide is annealed to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al. ((1999) *Genome Res.* 9: 492-498) is also a method that can be used to detect an amplicon of the invention. Using this method, an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. ((1996) *Nature Biotech.* 14: 303-308). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the method embodiments of the invention, more particularly, the identification and/or the detection of the DP-098140-6 event in biological samples. The kit of the invention can be used, and its components can be specifically adjusted, for purposes of quality control (e.g. purity of seed lots), detection of event DP-098140-6 in plant material, or material comprising or derived from plant material, such as but not limited to food or feed products.

In specific embodiments, a kit for identifying event DP-098140-6 in a biological sample is provided. The kit comprises a first and a second primer, wherein the first and second primer amplify a polynucleotide comprising a DP-098140-6 specific region. In further embodiments, the kit also comprises a polynucleotide for the detection of the DP-098140-6 specific region. The kit can comprise, for example, a first primer comprising a fragment of a polynucleotide of SEQ ID NO: 1, 2, 3, 46, 47, or 48, wherein the first or the second primer shares sufficient sequence homology or complementarity to the polynucleotide to amplify said DP-098140-6 specific region. For example, in specific embodiments, the first primer comprises a fragment of a polynucleotide of SEQ ID NO: 1, 2, 3, 46, 47 or 48, wherein the first or the second primer shares sufficient sequence homology or complementarity to the polynucleotide to amplify the DP-098140-6 specific region. The primer pair can comprise a fragment of SEQ ID NO: 1 and a fragment of SEQ ID NO: 2, 3, 46, or 47 or alternatively, the primer pair can comprises a fragment of SEQ ID NO: 2 or 46 and a fragment of SEQ ID NO:3, 47, or 1. In still further embodiments, the first and the second primer can comprise any one or any combination of the sequences set forth in SEQ ID NO:13, 14, 15, 16, 17, 18, 19, 20, 21, 25, 26, 27, 28, 29, 30, 31, 32, 33, 34, 35, 36, 37, 38, 39, 40, 41, 42, 43, 44, 45, 47, 51, 52, 53, 54, 55, or 56. The primers can be of any length sufficient to amplify the DP-098140-6 region including, for example, at least 6, 7, 8, 9, 10, 15, 20, 15, or 30 or about 7-10, 10-15, 15-20, 20-25, 25-30, 30-35, 35-40, 40-45 nucleotides or longer. In one embodiment, the primer comprises a fragment of SEQ ID NO: 24. The fragment can comprise 10, 20, 30, 40, 50, 60, 70, or greater consecutive nucleotides of SEQ ID NO: 24. In other embodiments, SEQ ID NO: 24 or a fragment thereof can be used as a probe. Such fragments can be used as a probe having at least 10, 20, 30, 40, 50, 60, 70, 80, 90, 100, 110, 120, 130, 140, 150, 160, or 170 or greater consecutive nucleotides of SEQ ID NO:24. In other embodiments, a probe comprising SEQ ID NO: 24 is used.

Further provided are DNA detection kits comprising at least one polynucleotide that can specifically detect a DP-098140-6 specific region or insert DNA, wherein said polynucleotide comprises at least one DNA molecule of a sufficient length of contiguous nucleotides homologous or complementary to SEQ ID NO: 1, 2, 3, 24, 47, 31-33, or 57. In specific embodiments, the DNA detection kit comprises a polynucleotide having SEQ ID NO: 5 or 6 or comprises a sequence which hybridizes with sequences selected from the group consisting of: a) the sequences of SEQ ID NO: 1 and SEQ ID NO: 3 or 47; and, b) the sequences of SEQ ID NO:2 or 46 and SEQ ID NO: 3 or 47.

Any of the polynucleotides and fragments and variants thereof employed in the methods and compositions of the invention can share sequence identity to a region of the transgene insert of the DP-098140-6 event, a junction sequence of the DP-098140-6 event or a flanking sequence of the DP-098140-6 event. Methods to determine the relationship of various sequences are known. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" any sequence comparison program that, for any two sequences in question, generates an alignment having identical nucleotide or amino acid residue matches and an identical percent sequence identity when compared to the corresponding alignment generated by GAP Version 10 is intended.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present invention provides methods for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of, and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The methods of the invention comprise planting the area of cultivation with the maize DP-098140-6 seeds or plants, and in specific embodiments, applying to the crop, seed, weed or area of cultivation thereof an effective amount of a herbicide of interest. It is recognized that the herbicide can be applied before or after the crop is planted in the area of cultivation. Such herbicide applications can include an application of glyphosate, an ALS inhibitor chemistry, or any combination thereof. In specific embodiments, a mixture of an ALS inhibitor chemistry in combination with glyphosate is applied to the maize DP-098140-6, wherein the effective concentration of at least the ALS inhibitor chemistry would significantly damage an appropriate control plant. In one non-limiting embodiment, the herbicide comprises at least one of a sulfonylaminocarbonyltriazolinone; a triazolopyrimidine; a pyrimidinyl (thio)benzoate; an imidazolinone; a triazine; and/or a phosphinic acid.

In another non-limiting embodiment, the combination of herbicides comprises glyphosate, imazapyr, chlorimuron-ethyl, quizalofop, and fomesafen, wherein an effective amount is tolerated by the crop and controls weeds. As disclosed elsewhere herein, any effective amount of these herbicides can be applied. In specific embodiments, this combination of herbicides comprises an effective amount of glyphosate comprising about 1110 to about 1130 g ai/hectare; an effective amount of imazapyr comprising about 7.5 to about 27.5 g ai/hectare; an effective amount of chlorimuron-ethyl comprising about 7.5 to about 27.5 g ai/hectare; an effective amount of quizalofop comprising about 50 to about 70 g ai/hectare; and, an effective amount of fomesafen comprising about 240 to about 260 g ai/hectare.

In other embodiments, a combination of at least two herbicides are applied, wherein the combination does not include glyphosate. In other embodiments, at least one ALS inhibitor and glyphosate is applied to the plant. More details regarding the various herbicide combinations that can be employed in the methods of the invention are discussed elsewhere herein.

In one embodiment, the method of controlling weeds comprises planting the area with the DP-098140-6 maize seeds or plants and applying to the crop, crop part, seed of said crop or the area under cultivation, an effective amount of a herbicide, wherein said effective amount comprises i) an amount that is not tolerated by a first control crop when applied to the first control crop, crop part, seed or the area of cultivation, wherein said first control crop expresses a first GLYAT polynucleotide that confers tolerance to glyphosate and does not express a second polynucleotide that encodes the zm-hra polypeptide;

ii) an amount that is not tolerated by a second control crop when applied to the second crop, crop part, seed or the area of cultivation, wherein said second control crop expresses the zm-hra polynucleotide and does not express the GLYAT polynucleotide; and, iii) an amount that is tolerated when applied to the DP-098140-6 maize crop, crop part, seed, or the area of cultivation thereof. The herbicide can comprise a combination of herbicides that either includes or does not include glyphosate. In specific embodiments, the combination of herbicides comprises ALS inhibitor chemistries as discussed in further detail below.

In another embodiment, the method of controlling weeds comprises planting the area with a DP-098140-6 maize crop seed or plant and applying to the crop, crop part, seed of said crop or the area under cultivation, an effective amount of a herbicide, wherein said effective amount comprises a level that is above the recommended label use rate for the crop, wherein said effective amount is tolerated when applied to the DP-098140-6 maize crop, crop part, seed, or the area of cultivation thereof. The herbicide applied can comprise a combination of herbicides that either includes or does not include glyphosate. In specific embodiments, the combination of herbicides comprises at least one ALS inhibitor chemistries as discussed in further detail below. Further herbicides and combinations thereof that can be employed in the various methods of the invention are discussed in further detail below.

A "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed; or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green (1998) *Weed Technology* 12: 474-477; Green and Ulrich (1993) *Weed Science* 41: 508-516. In some instances, an appropriate control maize plant is a "Jack" maize plant (Illinois Foundation Seed, Champaign, Ill.). In other embodiments, the null segregant can be used as a control, as they are genetically identical to DP-098140-6 with the exception of the transgenic insert DNA.

Any herbicide can be applied to the DP-098140-6 maize crop, crop part, or the area of cultivation containing the crop plant. Classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application), or by how they are taken up by or affect the plant. For example, thifensulfuron-methyl and tribenuron-methyl are applied to the foliage of a crop and are generally metabolized there, while rimsulfuron and chlorimuron-ethyl are generally taken up through both the roots and foliage of a plant. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1).

Often, a herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments of the invention, a transgenic plant of the invention is tolerant to more than one herbicide or chemical in the same class or subclass, such as, for example, an inhibitor of PPO, a sulfonylurea, or a synthetic auxin.

Typically, the plants of the present invention can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

The invention thereby provides a transgenic maize plant which can be selected for use in crop production based on the prevalence of herbicide-tolerant weed species in the area where the transgenic crop is to be grown. Methods are known in the art for assessing the herbicide tolerance of various weed species. Weed management techniques are also known in the art, such as for example, crop rotation using a crop that is tolerant to a herbicide to which the local weed species are not tolerant. A number of entities monitor and publicly report the incidence and characteristics of herbicide-tolerant weeds, including the Herbicide Resistance Action Committee (HRAC), the Weed Science Society of America, and various state agencies (see, e.g., see, for example, herbicide tolerance scores for various broadleaf weeds from the 2004 Illinois Agricultural Pest Management Handbook), and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler (2004), 2005 *Herbicide Manual for Agricultural Professionals*, Pub. WC 92 Revised (Iowa State University Extension, Iowa State University of Science and Technology, Ames, Iowa); *Weed Control for Corn, Maizes, and Sorghum*, Chapter 2 of "2004 Illinois Agricultural Pest Management Handbook" (University of Illinois Extension, University of Illinois at Urbana-Champaign, Ill.); *Weed Control Guide for Field Crops*, MSU Extension Bulletin E434 (Michigan State University, East Lansing, Mich.)).

TABLE 1

Abbreviated version of HRAC Herbicide Classification

I. ALS Inhibitors (WSSA Group 2)
   A. Sulfonylureas
      1. Azimsulfuron
      2. Chlorimuron-ethyl
      3. Metsulfuron-methyl
      4. Nicosulfuron
      5. Rimsulfuron
      6. Sulfometuron-methyl
      7. Thifensulfuron-methyl
      8. Tribenuron-methyl
      9. Amidosulfuron
     10. Bensulfuron-methyl
     11. Chlorsulfuron
     12. Cinosulfuron
     13. Cyclosulfamuron
     14. Ethametsulfuron-methyl
     15. Ethoxysulfuron
     16. Flazasulfuron
     17. Flupyrsulfuron-methyl
     18. Foramsulfuron
     19. Imazosulfuron
     20. Iodosulfuron-methyl
     21. Mesosulfuron-methyl
     22. Oxasulfuron
     23. Primisulfuron-methyl
     24. Prosulfuron
     25. Pyrazosulfuron-ethyl
     26. Sulfosulfuron
     27. Triasulfuron
     28. Trifloxysulfuron
     29. Triflusulfuron-methyl
     30. Tritosulfuron
     31. Halosulfuron-methyl
     32. Flucetosulfuron
   B. Sulfonylaminocarbonyltriazolinones
      1. Flucarbazone
      2. Procarbazone
   C. Triazolopyrimidines
      1. Cloransulam-methyl
      2. Flumetsulam
      3. Diclosulam
      4. Florasulam
      5. Metosulam
      6. Penoxsulam
      7. Pyroxsulam TABLE 1-continued Abbreviated version of HRAC Herbicide Classification

- D. Pyrimidinyloxy(thio)benzoates
  1. Bispyribac
  2. Pyriftalid
  3. Pyribenzoxim
  4. Pyrithiobac
  5. Pyriminobac-methyl
- E. Imidazolinones
  1. Imazapyr
  2. Imazethapyr
  3. Imazaquin
  4. Imazapic
  5. Imazamethabenz-methyl
  6. Imazamox II. Other Herbicides - Active Ingredients/ Additional Modes of Action
- A. Inhibitors of Acetyl CoA carboxylase (ACCase) (WSSA Group 1)
  1. Aryloxyphenoxypropionates ('FOPs')
     a. Quizalofop-P-ethyl
     b. Diclofop-methyl
     c. Clodinafop-propargyl
     d. Fenoxaprop-P-ethyl
     e. Fluazifop-P-butyl
     f. Propaquizafop
     g. Haloxyfop-P-methyl
     h. Cyhalofop-butyl
     i. Quizalofop-P-ethyl
  2. Cyclohexanediones ('DIMs')
     a. Alloxydim
     b. Butroxydim
     c. Clethodim
     d. Cycloxydim
     e. Sethoxydim
     f. Tepraloxydim
     g. Tralkoxydim
- B. Inhibitors of Photosystem II-HRAC Group C1/WSSA Group 5
  1. Triazines
     a. Ametryne
     b. Atrazine
     c. Cyanazine
     d. Desmetryne
     e. Dimethametryne
     f. Prometon
     g. Prometryne
     h. Propazine
     i. Simazine
     j. Simetryne
     k. Terbumeton
     l. Terbuthylazine
     m. Terbutryne
     n. Trietazine
  2. Triazinones
     a. Hexazinone
     b. Metribuzin
     c. Metamitron
  3. Triazolinone
     a. Amicarbazone
  4. Uracils
     a. Bromacil
     b. Lenacil
     c. Terbacil
  5. Pyridazinones
     a. Pyrazon
  6. Phenyl carbamates
     a. Desmedipham
     b. Phenmedipham
- C. Inhibitors of Photosystem II-HRAC Group C2/WSSA Group 7
  1. Ureas
     a. Fluometuron
     b. Linuron
     c. Chlorobromuron
     d. Chlorotoluron
     e. Chloroxuron
     f. Dimefuron
     g. Diuron
     h. Ethidimuron
     i. Fenuron
     j. Isoproturon
     k. Isouron
     l. Methabenzthiazuron
     m. Metobromuron
     n. Metoxuron
     o. Monolinuron
     p. Neburon
     q. Siduron
     r. Tebuthiuron
  2. Amides
     a. Propanil
     b. Pentanochlor
- D. Inhibitors of Photosystem II-HRAC Group C3/WSSA Group 6
  1. Nitriles
     a. Bromofenoxim
     b. Bromoxynil
     c. Ioxynil
  2. Benzothiadiazinone (Bentazon)
     a. Bentazon
  3. Phenylpyridazines
     a. Pyridate
     b. Pyridafol
- E. Photosystem-I-electron diversion (Bipyridyliums) (WSSA Group 22)
  1. Diquat
  2. Paraquat
- F. Inhibitors of PPO (protoporphyrinogen oxidase) (WSSA Group 14)
  1. Diphenylethers
     a. Acifluorfen-Na
     b. Bifenox
     c. Chlomethoxyfen
     d. Fluoroglycofen-ethyl
     e. Fomesafen
     f. Halosafen
     g. Lactofen
     h. Oxyfluorfen
  2. Phenylpyrazoles
     a. Fluazolate
     b. Pyraflufen-ethyl
  3. N-phenylphthalimides
     a. Cinidon-ethyl
     b. Flumioxazin
     c. Flumiclorac-pentyl
  4. Thiadiazoles
     a. Fluthiacet-methyl
     b. Thidiazimin
  5. Oxadiazoles
     a. Oxadiazon
     b. Oxadiargyl
  6. Triazolinones
     a. Carfentrazone-ethyl
     b. Sulfentrazone
  7. Oxazolidinediones
     a. Pentoxazone
  8. Pyrimidindiones
     a. Benzfendizone
     b. Butafenicil
  9. Others
     a. Pyrazogyl
     b. Profluazol
- G. Bleaching: Inhibition of carotenoid biosynthesis at the phytoene desaturase step (PDS) (WSSA Group 12)
  1. Pyridazinones
     a. Norflurazon
  2. Pyridinecarboxamides
     a. Diflufenican
     b. Picolinafen
  3. Others
     a. Beflubutamid
     b. Fluridone
     c. Flurochloridone
     d. Flurtamone TABLE 1-continued Abbreviated version of HRAC Herbicide Classification

- H. Bleaching: Inhibition of 4-hydroxyphenyl-pyruvate-dioxygenase (4-HPPD) (WSSA Group 28)
  1. Triketones
     a. Mesotrione
     b. Sulcotrione
     c. topremezone
     d. temtorione
  2. Isoxazoles
     a. Isoxachlortole
     b. Isoxaflutole
  3. Pyrazoles
     a. Benzofenap
     b. Pyrazoxyfen
     c. Pyrazolynate
  4. Others
     a. Benzobicyclon
- I. Bleaching: Inhibition of carotenoid biosynthesis (unknown target) (WSSA Group 11 and 13)
  1. Triazoles (WSSA Group 11)
     a. Amitrole
  2. Isoxazolidinones (WSSA Group 13)
     a. Clomazone
  3. Ureas
     a. Fluometuron
  3. Diphenylether
     a. Aclonifen
- J. Inhibition of EPSP Synthase
  1. Glycines (WSSA Group 9)
     a. Glyphosate
     b. Sulfosate
- K. Inhibition of glutamine synthetase
  1. Phosphinic Acids
     a. Glufosinate-ammonium
     b. Bialaphos
- L. Inhibition of DHP (dihydropteroate) synthase (WSSA Group 18)
  1 Carbamates
     a. Asulam
- M. Microtubule Assembly Inhibition (WSSA Group 3)
  1. Dinitroanilines
     a. Benfluralin
     b. Butralin
     c. Dinitramine
     d. Ethalfluralin
     e. Oryzalin
     f. Pendimethalin
     g. Trifluralin
  2. Phosphoroamidates
     a. Amiprophos-methyl
     b. Butamiphos
  3. Pyridines
     a. Dithiopyr
     b. Thiazopyr
  4. Benzamides
     a. Pronamide
     b. Tebutam
  5. Benzenedicarboxylic acids
     a. Chlorthal-dimethyl
- N. Inhibition of mitosis/microtubule organization WSSA Group 23)
  1. Carbamates
     a. Chlorpropham
     b. Propham
     c. Carbetamide
- O. Inhibition of cell division (Inhibition of very long chain fatty acids as proposed mechanism; WSSA Group 15)
  1. Chloroacetamides
     a. Acetochlor
     b. Alachlor
     c. Butachlor
     d. Dimethachlor
     e. Dimethanamid
     f. Metazachlor
     g. Metolachlor
     h. Pethoxamid
     i. Pretilachlor
     j. Propachlor
     k. Propisochlor
     l. Thenylchlor
  2. Acetamides
     a. Diphenamid
     b. Napropamide
     c. Naproanilide
  3. Oxyacetamides
     a. Flufenacet
     b. Mefenacet
  4. Tetrazolinones
     a. Fentrazamide
  5. Others
     a. Anilofos
     b. Cafenstrole
     c. Indanofan
     d. Piperophos
- P. Inhibition of cell wall (cellulose) synthesis
  1. Nitriles (WSSA Group 20)
     a. Dichlobenil
     b. Chlorthiamid
  2. Benzamides (isoxaben (WSSA Group 21))
     a. Isoxaben
  3. Triazolocarboxamides (flupoxam)
     a. Flupoxam
- Q. Uncoupling (membrane disruption): (WSSA Group 24)
  1. Dinitrophenols
     a. DNOC
     b. Dinoseb
     c. Dinoterb
- R. Inhibition of Lipid Synthesis by other than ACC inhibition
  1. Thiocarbamates (WSSA Group 8)
     a. Butylate
     b. Cycloate
     c. Dimepiperate
     d. EPTC
     e. Esprocarb
     f. Molinate
     g. Orbencarb
     h. Pebulate
     i. Prosulfocarb
     j. Benthiocarb
     k. Tiocarbazil
     l. Triallate
     m. Vernolate
  2. Phosphorodithioates
     a. Bensulide
  3. Benzofurans
     a. Benfuresate
     b. Ethofumesate
  4. Halogenated alkanoic acids (WSSA Group 26)
     a. TCA
     b. Dalapon
     c. Flupropanate
- S. Synthetic auxins (IAA-like) (WSSA Group 4)
  1. Phenoxycarboxylic acids
     a. Clomeprop
     b. 2,4-D
     c. Mecoprop
  2. Benzoic acids
     a. Dicamba
     b. Chloramben
     c. TBA
  3. Pyridine carboxylic acids
     a. Clopyralid
     b. Fluroxypyr
     c. Picloram
     d. Tricyclopyr

TABLE 1-continued

Abbreviated version of HRAC Herbicide Classification

4. Quinoline carboxylic acids
    a. Quinclorac
    b. Quinmerac
5. Others (benazolin-ethyl)
    a. Benazolin-ethyl T. Inhibition of Auxin Transport
1. Phthalamates; semicarbazones (WSSA Group 19)
    a. Naptalam
    b. Diflufenzopyr-Na U. Other Mechanism of Action
1. Arylaminopropionic acids
    a. Flamprop-M-methyl/-isopropyl
2. Pyrazolium
    a. Difenzoquat
3. Organoarsenicals
    a. DSMA
    b. MSMA
4. Others
    a. Bromobutide
    b. Cinmethylin
    c. Cumyluron
    d. Dazomet
    e. Daimuron-methyl
    f. Dimuron
    g. Etobenzanid
    h. Fosamine
    i. Metam
    j. Oxaziclomefone
    k. Oleic acid
    l. Pelargonic acid
    m. Pyributicarb In one embodiment, one ALS inhibitor or at least two ALS inhibitors are applied to the DP-098140-6 maize crop or area of cultivation. In non-limiting embodiments, the combination of ALS inhibitor herbicides can include or does not include glyphosate. The ALS inhibitor can be applied at any effective rate that selectively controls weeds and does not significantly damage the crop. In specific embodiments, at least one ALS inhibitor is applied at a level that would significantly damage an appropriate control plant. In other embodiments, at least one ALS inhibitor is applied above the recommended label use rate for the crop. In still other embodiments, a mixture of ALS inhibitors is applied at a lower rate than the recommended use rate and weeds continue to be selectively controlled. Herbicides that inhibit acetolactate synthase (also known as acetohydroxy acid synthase) and are therefore useful in the methods of the invention include sulfonylureas as listed in Table 1, including agriculturally suitable salts (e.g., sodium salts) thereof, sulfonylaminocarbonyltriazolinones as listed in Table 1, including agriculturally suitable salts (e.g., sodium salts) thereof, triazolopyrimidines as listed in Table 1, including agriculturally suitable salts (e.g., sodium salts) thereof, pyrimidinyloxy(thio)benzoates as listed in Table 1, including agriculturally suitable salts (e.g., sodium salts) thereof, and imidazolinones as listed in Table 1, including agriculturally suitable salts (e.g., sodium salts) thereof. In some embodiments, methods of the invention comprise the use of a sulfonylurea which is not chlorimuron-ethyl, chlorsulfuron, rimsulfuron, thifensulfuron-methyl, or tribenuron-methyl.

In still further methods, glyphosate, alone or in combination with another herbicide of interest, can be applied to the DP-098140-6 maize plants or their area of cultivation. Non-limiting examples of glyphosate formations are set forth in Table 2. In specific embodiments, the glyphosate is in the form of a salt, such as, ammonium, isopropylammonium, potassium, sodium (including sesquisodium) or trimesium (alternatively named sulfosate). In still further embodiments, a mixture of a synergistically effective amount of a combination of glyphosate and an ALS inhibitor (such as a sulfonylurea) is applied to the DP-098140-6 maize plants or their area of cultivation.

TABLE 2

Glyphosate formulations comparisons.

| Herbicide by Registered Trademark | Manufacturer | Salt | Active ingredient per gallon | Acid equivalent per gallon | Apply: fl oz/ acre | Acid equivalent per acre |
|---|---|---|---|---|---|---|
| Roundup Original | Monsanto | Isopropylamine | 4 | 3 | 32 | 0.750 |
| Roundup Original II | Monsanto | Isopropylamine | 4 | 3 | 32 | 0.750 |
| Roundup Original MAX | Monsanto | Potassium | 5.5 | 4.5 | 22 | 0.773 |
| Roundup UltraMax | Monsanto | Isopropylamine | 5 | 3.68 | 26 | 0.748 |
| Roundup UltraMax II | Monsanto | Potassium | 5.5 | 4.5 | 22 | 0.773 |
| Roundup Weathermax | Monsanto | Potassium | 5.5 | 4.5 | 22 | 0.773 |
| Touchdown | Syngenta | Diammonium | 3.7 | 3 | 32 | 0.750 |
| Touchdown HiTech | Syngenta | Potassium | 6.16 | 6 | 20 | 0.781 |
| Touchdown Total | Syngenta | Potassium | 5.14 | 4.17 | 24 | 0.782 |
| Durango | Dow AgroSciences | Isopropylamine | 5.4 | 4 | 24 | 0.750 |
| Glyphomax | Dow AgroSciences | Isopropylamine | 4 | 3 | 32 | 0.750 |
| Glyphomax Plus | Dow AgroSciences | Isopropylamine | 4 | 3 | 32 | 0.750 |
| Glyphomax XRT | Dow AgroSciences | Isopropylamine | 4 | 3 | 32 | 0.750 |
| Gly Star Plus | Albaugh/Agri Star | Isopropylamine | 4 | 3 | 32 | 0.750 |
| Gly Star 5 | Albaugh/Agri Star | Isopropylamine | 5.4 | 4 | 24 | 0.750 |
| Gly Star Original | Albaugh/Agri Star | Isopropylamine | 4 | 3 | 32 | 0.750 |
| Gly-Flo | Micro Flo | Isopropylamine | 4 | 3 | 32 | 0.750 |
| Credit | Nufarm | Isopropylamine | 4 | 3 | 32 | 0.750 |
| Credit Extra | Nufarm | Isopropylamine | 4 | 3 | 32 | 0.750 |
| Credit Duo | Nufarm | Isopro. + monoamm. | 4 | 3 | 32 | 0.750 |
| Credit Duo Extra | Nufarm | Isopro. + monoamm. | 4 | 3 | 32 | 0.750 |
| Extra Credit 5 | Nufarm | Isopropylamine | 5 | 3.68 | 26 | 0.748 |
| Cornerstone | Agriliance | Isopropylamine | 4 | 3 | 32 | 0.750 |
| Cornerstone Plus | Agriliance | Isopropylamine | 4 | 3 | 32 | 0.750 |
| Glyfos | Cheminova | Isopropylamine | 4 | 3 | 32 | 0.750 |
| Glyfos X-TRA | Cheminova | Isopropylamine | 4 | 3 | 32 | 0.750 |
| Rattler | Helena | Isopropylamine | 4 | 3 | 32 | 0.750 |

TABLE 2-continued

Glyphosate formulations comparisons.

| Herbicide by Registered Trademark | Manufacturer | Salt | Active ingredient per gallon | Acid equivalent per gallon | Apply: fl oz/ acre | Acid equivalent per acre |
|---|---|---|---|---|---|---|
| Rattler Plus | Helena | Isopropylamine | 4 | 3 | 32 | 0.750 |
| Mirage | UAP | Isopropylamine | 4 | 3 | 32 | 0.750 |
| Mirage Plus | UAP | Isopropylamine | 4 | 3 | 32 | 0.750 |
| Glyphosate 41% | Helm Agro USA | Isopropylamine | 4 | 3 | 32 | 0.750 |
| Buccaneer | Tenkoz | Isopropylamine | 4 | 3 | 32 | 0.750 |
| Buccaneer Plus | Tenkoz | Isopropylamine | 4 | 3 | 32 | 0.750 |
| Honcho | Monsanto | Isoproylamine | 4 | 3 | 32 | 0.750 |
| Honcho Plus | Monsanto | Isoproylamine | 4 | 3 | 32 | 0.750 |
| Gly-4 | Univ. Crop Prot. Alli | Isopropylamine | 4 | 3 | 32 | 0.750 |
| Gly-4 Plus | Univ. Crop Prot. Alli | Isopropylamine | 4 | 3 | 32 | 0.750 |
| ClearOut 41 | Chemical Products Tech. | Isopropylamine | 4 | 3 | 32 | 0.750 |
| ClearOut 41 Plus | Chemical Products Tech. | Isopropylamine | 4 | 3 | 32 | 0.750 |
| Spitfire | Control Solutions | Isopropylamine | 4 | 3 | 32 | 0.750 |
| Spitfire Plus | Control Solutions | Isopropylamine | 4 | 3 | 32 | 0.750 |
| Glyphosate 4 | FarmerSaver.com | Isopropylamine | 4 | 3 | 32 | 0.750 |
| FS Glyphosate Plus | Growmark | Isopropylamine | 4 | 3 | 32 | 0.750 |
| Glyphosate Original | Griffin, LLC | Isopropylamine | 4 | 3 | 32 | 0.750 |

Thus, in some embodiments, a transgenic plant of the invention is used in a method of growing a DP-098140-6 maize crop by the application of herbicides to which the plant is tolerant. In this manner, treatment with a combination of one of more herbicides which include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benzolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxium, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chloroflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl CUH-35 (2-methoxyethyl 2-[[[4-chloro-2-fluoro-5-[(1-methyl-2-propynyl)oxy]phenyl](3-fluoro-benzoyl)amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and it dimethylammonium, diolamine and trolamine salts, daimurton, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salts, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamethabenz-methyl, imazamox, imazapic, imazapyr, imazaquin, imazagin-ammonium, imazethapyr, imazaethapyr-ammonium, imazosulfuron, indanofan, iodosulfuron-methyl, ioxynil, ioxynil octanoate, ioxynil-sodium, isoproturon, isouron, isoaben, isoxaflutole, isoxachlortole, lactofen, lenacil, linuron, maleic hydrazide, MCPA and its salts (e.g., MCPA-dimethylammonium, MCPA-potassium and MCPA-sodium, ester (e.g., MCPA-2-ethylhexyl, MCPA-butotyl) and thioester (e.g., MCPA-thioethyl), MCPB and its salts (e.g., MCPB-sodium) and esters (e.g., MCPB-ethyl), mecoprop, mecoprop-P, mefenacet, mefluidid, mesosulfuron-methyl, mesotrione, metam-sodium, metamifop, metamitron, metazachlor, methabenzthiazuron, methylarsonic acid and its calcium, monoammonium, monosodium and disodium salts, methldymron, metobenzuron, metobromuron, metolachlor, S-metholachlor, metosulam, metoxuron, metribuzin, metsulfuron-methyl, molinate, monolinuron, naproanilide, napropamide, naptalam, neburon, nicosulfuran, norflurazon, orbencarb, oryzalin, oxadiargyl, oxadiazon, oxasulfuron, oxaziclomefone, oxyflurorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quinalofop-ethyl, quizalofop-P-ethyl, quizalofop-P-tefuryl, rumsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate is disclosed.

Other suitable herbicides and agricultural chemicals are known in the art, such as, for example, those described in WO 2005/041654. Other herbicides also include bioherbicides such as *Alternaria destruens* Simmons, *Colletotrichum gloeosporioides* (Penz.) Penz. & Sacc., *Drechsiera monoceras* (MTB-951), *Myrothecium verrucaria* (Albertini & Schweinitz) Ditmar: Fries, *Phytophthora palmivora* (Butyl.) Butyl. and *Puccinia thlaspeos* Schub. Combinations of various herbicides can result in a greater-than-additive (i.e., synergistic) effect on weeds and/or a less-than-additive effect (i.e. safening) on crops or other desirable plants. In certain instances, combinations of glyphosate with other herbicides having a similar spectrum of control but a different mode of action will be particularly advantageous for preventing the development of resistant weeds. Herbicidally effective amounts of any particular herbicide can be easily determined by one skilled in the art through simple experimentation.

Herbicides may be classified into groups and/or subgroups as described herein above with reference to their mode of action, or they may be classified into groups and/or subgroups in accordance with their chemical structure.

Sulfonamide herbicides have as an essential molecular structure feature a sulfonamide moiety (—S(O)$_2$NH—). As referred to herein, sulfonamide herbicides particularly comprise sulfonylurea herbicides, sulfonylaminocarbonyltriazolinone herbicides and triazolopyrimidine herbicides. In sulfonylurea herbicides the sulfonamide moiety is a component in a sulfonylurea bridge (—S(O)$_2$NHC(O)NH(R)—). In sulfonylurea herbicides the sulfonyl end of the sulfonylurea bridge is connected either directly or by way of an oxygen atom or an optionally substituted amino or methylene group to a typically substituted cyclic or acyclic group. At the opposite end of the sulfonylurea bridge, the amino group, which may have a substituent such as methyl (R being CH$_3$) instead of hydrogen, is connected to a heterocyclic group, typically a symmetric pyrimidine or triazine ring, having one or two substituents such as methyl, ethyl, trifluoromethyl, methoxy, ethoxy, methylamino, dimethylamino, ethylamino and the halogens. In sulfonylaminocarbonyltriazolinone herbicides, the sulfonamide moiety is a component of a sulfonylaminocarbonyl bridge (—S(O)$_2$NHC(O)—). In sulfonylaminocarbonyltriazolinone herbicides the sulfonyl end of the sulfonylaminocarbonyl bridge is typically connected to substituted phenyl ring. At the opposite end of the sulfonylaminocarbonyl bridge, the carbonyl is connected to the 1-position of a triazolinone ring, which is typically substituted with groups such as alkyl and alkoxy. In triazolopyrimidine herbicides the sulfonyl end of the sulfonamide moiety is connected to the 2-position of a substituted [1,2,4]triazolopyrimidine ring system and the amino end of the sulfonamide moiety is connected to a substituted aryl, typically phenyl, group or alternatively the amino end of the sulfonamide moiety is connected to the 2-position of a substituted [1,2,4]triazolopyrimidine ring system and the sulfonyl end of the sulfonamide moiety is connected to a substituted aryl, typically pyridinyl, group.

Representative of the sulfonylurea herbicides useful in the present invention are those of the formula:

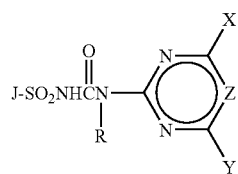

wherein:

J is selected from the group consisting of

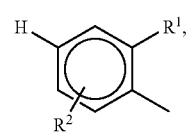

J-1

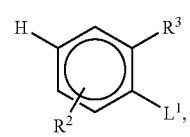

J-2

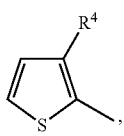

J-3

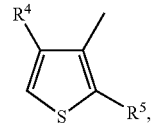

J-4

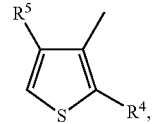

J-5

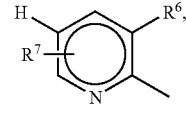

J-6

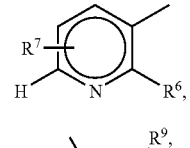

J-7

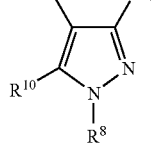

J-8

-continued

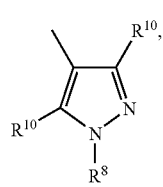
J-9

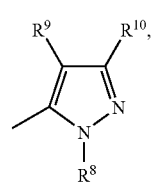
J-10

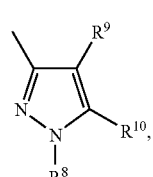
J-11

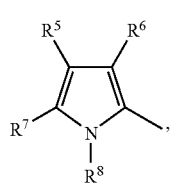
J-12

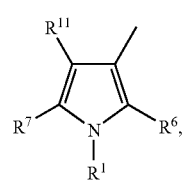
J-13

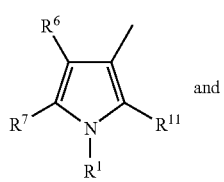
J-14

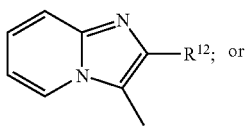
J-15

J is $R^{13}SO_2N(CH_3)$—;

R is H or $CH_3$;

$R^1$ is F, Cl, Br, $NO_2$, $C_1$-$C_4$ alkyl, $C_1$-$C_4$ haloalkyl, $C_3$-$C_4$ cycloalkyl, $C_2$-$C_4$ haloalkenyl, $C_1$-$C_4$ alkoxy, $C_1$-$C_4$ haloalkoxy, $C_2$-$C_4$ alkoxyalkoxy, $CO_2R^{14}$, $C(O)NR^{15}R^{16}$, $SO_2NR^{17}R^{18}$, $S(O)_nR^{19}$, $C(O)R^{20}$, $CH_2CN$ or L;

$R^2$ is H, F, Cl, Br, I, CN, $CH_3$, $OCH_3$, $SCH_3$, $CF_3$ or $OCF_2H$;

$R^3$ is Cl, $NO_2$, $CO_2CH_3$, $CO_2CH_2CH_3$, $C(O)CH_3$, $C(O)CH_2CH_3$, C(O)-cyclopropyl, $SO_2N(CH_3)_2$, $SO_2CH_3$, $SO_2CH_2CH_3$, $OCH_3$ or $OCH_2CH_3$;

$R^4$ is $C_1$-$C_3$ alkyl, $C_1$-$C_2$ alkoxy, $C_2$-$C_4$ haloalkenyl, F, Cl, Br, $NO_2$, $CO_2R^{14}$, $C(O)NR^{15}R^{16}$, $SO_2NR^{17}R^{18}$, $S(O)_nR^{19}$, $C(O)R^{20}$ or L;

$R^5$ is H, F, Cl, Br or $CH_3$;

$R^6$ is $C_1$-$C_3$ alkyl optionally substituted with 0-3 F, 0-1 Cl and 0-1 $C_3$-$C_4$ alkoxyacetyloxy, or $R^6$ is $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^7$ is H, F, Cl, $CH_3$ or $CF_3$;

$R^8$ is H, $C_1$-$C_3$ alkyl or pyridinyl;

$R^9$ is $C_1$-$C_3$ alkyl, $C_1$-$C_2$ alkoxy, F, Cl, Br, $NO_2$, $CO_2R^{14}$, $SO_2NR^{17}R^{18}$, $S(O)_nR^{19}$, $OCF_2H$, $C(O)R^{20}$, $C_2$-$C_4$ haloalkenyl or L;

$R^{10}$ is H, Cl, F, Br, $C_1$-$C_3$ alkyl or $C_1$-$C_2$ alkoxy;

$R^{11}$ is H, $C_1$-$C_3$ alkyl, $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^{12}$ is halogen, $C_1$-$C_4$ alkyl or $C_1$-$C_3$ alkylsulfonyl;

$R^{13}$ is $C_1$-$C_4$ alkyl;

$R^{14}$ is allyl, propargyl or oxetan-3-yl; or $R^{14}$ is $C_1$-$C_3$ alkyl optionally substituted by at least one member independently selected from halogen, $C_1$-$C_2$ alkoxy and CN;

$R^{15}$ is H, $C_1$-$C_3$ alkyl or $C_1$-$C_2$ alkoxy;

$R^{16}$ is $C_1$-$C_2$ alkyl;

$R^{17}$ is H, $C_1$-$C_3$ alkyl, $C_1$-$C_2$ alkoxy, allyl or cyclopropyl;

$R^{18}$ is H or $C_1$-$C_3$ alkyl;

$R^{19}$ is $C_1$-$C_3$ alkyl, $C_1$-$C_3$ haloalkyl, allyl or propargyl;

$R^{20}$ is $C_1$-$C_4$ alkyl, $C_1$-$C_4$ haloalkyl or $C_3$-$C_5$ cycloalkyl optionally substituted by halogen;

n is 0, 1 or 2;

L is

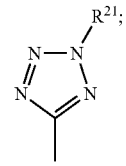

$L^1$ is $CH_2$, NH or O;

$R^{21}$ is H or $C_1$-$C_3$ alkyl;

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido or cyano; and Z is CH or N;

provided that (i) when one or both of X and Y is $C_1$ haloalkoxy, then Z is CH; and (ii) when X is halogen, then Z is CH and Y is $OCH_3$, $OCH_2CH_3$, $N(OCH_3)CH_3$, $NHCH_3$, $N(CH_3)_2$ or $OCF_2H$. Of note is the present single liquid herbicide composition comprising one or more sulfonylureas of Formula I wherein when $R^6$ is alkyl, said alkyl is unsubstituted.

Representative of the triazolopyrimidine herbicides contemplated for use in this invention are those of the formula:

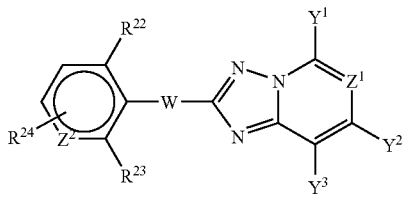

wherein:
R$^{22}$ and R$^{23}$ each independently halogen, nitro, C$_1$-C$_4$ alkyl, C$_1$-C$_4$ haloalkyl, C$_1$-C$_4$ alkoxy, C$_1$-C$_4$ haloalkoxy or C$_2$-C$_3$ alkoxycarbonyl;
R$^{24}$ is H, halogen, C$_1$-C$_2$ alkyl or C$_1$-C$_2$ alkoxy;
W is —NHS(O)$_2$— or —S(O)$_2$NH—;
Y$^1$ is H, C$_1$-C$_2$ alkyl or C$_1$-C$_2$ alkoxy;
Y$^2$ is H, F, Cl, Br, C$_1$-C$_2$ alkyl or C$_1$-C$_2$ alkoxy;
Y$^3$ is H, F or methoxy;
Z$^1$ is CH or N; and
Z$^2$ is CH or N;
provided that at least one of Y$^1$ and Y$^2$ is other than H.

In the above Markush description of representative triazolopyrimidine herbicides, when W is —NHS(O)$_2$— the sulfonyl end of the sulfonamide moiety is connected to the [1,2,4]triazolopyrimidine ring system, and when W is —S(O)$_2$ NH— the amino end of the sulfonamide moiety is connected to the [1,2,4]triazolopyrimidine ring system.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. "Cycloalkyl" includes, for example, cyclopropyl, cyclobutyl and cyclopentyl. "Alkenyl" includes straight-chain or branched alkenes such as ethenyl, 1-propenyl, 2-propenyl, and the different butenyl isomers. "Alkenyl" also includes polyenes such as 1,2-propadienyl and 2,4-butadienyl. "Alkynyl" includes straight-chain or branched alkynes such as ethynyl, 1-propynyl, 2-propynyl and the different butynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkoxyalkoxy" denotes alkoxy substitution on alkoxy. "Alkenyloxy" includes straight-chain or branched alkenyloxy moieties. Examples of "alkenyloxy" include H$_2$C=CHCH$_2$O, (CH$_3$)CH=CHCH$_2$O and CH$_2$=CHCH$_2$CH$_2$O. "Alkynyloxy" includes straight-chain or branched alkynyloxy moieties. Examples of "alkynyloxy" include HC≡CCH$_2$O and CH$_3$C≡CCH$_2$O "Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include CH$_3$SCH$_2$, CH$_3$SCH$_2$CH$_2$, CH$_3$CH$_2$SCH$_2$, CH$_3$CH$_2$CH$_2$CH$_2$SCH$_2$ and CH$_3$ CH$_2$SCH$_2$CH$_2$; "alkylsulfinylalkyl" and "alkylsulfonylalkyl" include the corresponding sulfoxides and sulfones, respectively. Other substituents such as "alkylamino", "dialkylamino" are defined analogously.

The total number of carbon atoms in a substituent group is indicated by the "C$_i$-C$_j$" prefix where i and j are numbers from 1 to 5. For example, C$_1$-C$_4$ alkyl designates methyl through butyl, including the various isomers. As further examples, C$_2$ alkoxyalkyl designates CH$_3$OCH$_2$; C$_3$ alkoxyalkyl designates, for example, CH$_3$CH(OCH$_3$), CH$_3$OCH$_2$CH$_2$ or CH$_3$CH$_2$OCH$_2$; and C$_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. The terms "haloalkoxy", "haloalkylthio", and the like, are defined analogously to the term "haloalkyl". Examples of "haloalkoxy" include CF$_3$O, CCl$_3$CH$_2$O, HCF$_2$CH$_2$CH$_2$O and CF$_3$CH$_2$O. Examples of "haloalkylthio" include CCl$_3$S, CF$_3$S, CCl$_3$CH$_2$S and ClCH$_2$CH$_2$CH$_2$S.

The following sulfonylurea herbicides illustrate the sulfonylureas useful for this invention: amidosulfuron (N-[[[[(4,6-dimethoxy-2-pyrimdinyl)amino]carbonyl]amino]-sulfonyl]-N-methylmethanesulfonamide), azimsulfuron (N-[[(4,6-dimethoxy-2-pyrimidinyl)amino]carbonyl]-1-methyl-4-(2-methyl-2H-tetrazol-5-yl)-1H-pyrazole-5-sulfonamide), bensulfuron-methyl (methyl 2-[[[[[(4,6-dimethoxy-2-pyrimidinyl)amino]carbonyl]amino]sulfonyl]methyl]benzoate), chlorimuron-ethyl (ethyl 2-[[[[(4-chloro-6-methoxy-2-pyrimidinyl)amino]carbonyl]amino]sulfonyl]-benzoate), chlorsulfuron (2-chloro-N-[[(4-methoxy-6-methyl-1,3,5-triazin-2-yl)amino]-carbonyl]benzenesulfonamide), cinosulfuron (N-[[(4,6-dimethoxy-1,3,5-triazin-2-yl)amino]carbonyl]-2-(2-methoxyethoxy)benzenesulfonamide), cyclosulfamuron (N-[[[2-(cyclopropylcarbonyl)phenyl]amino]sulfonyl]-N$^1$-(4,6-dimethoxypyrimidin-2-yl)urea), ethametsulfuron-methyl (methyl 2-[[[[[4-ethoxy-6-(methylamino)-1,3,5-triazin-2-yl]amino]carbonyl]amino]sulfonyl]benzoate), ethoxysulfuron (2-ethoxyphenyl[[(4,6-dimethoxy-2-pyrimidinyl)amino]carbonyl]sulfamate), flazasulfuron (N-[[(4,6-dimethoxy-2-pyrimidinyl) amino]carbonyl]-3-(trifluoromethyl)-2-pyridinesulfonamide), flucetosulfuron (1-[3-[[[[(4,6-dimethoxy-2-pyrimidinyl)amino]carbonyl]amino]sulfonyl]-2-pyridinyl]-2-fluoropropyl methoxyacetate), flupyrsulfuron-methyl (methyl 2-[[[[(4,6-dimethoxy-2-pyrimidinyl)amino]carbonyl]amino]sulfonyl]-6-(trifluoromethyl)-3-pyridinecarboxylate), foramsulfuron (2-[[[[(4,6-dimethoxy-2-pyrimidinyl)amino]carbonyl]amino]sulfonyl]-4-(formylamino)-N,N-dimethylbenzamide), halosulfuron-methyl (methyl 3-chloro-5-[[[[(4,6-dimethoxy-2-pyrimidinyl)amino]-carbonyl]amino]sulfonyl]-1-methyl-1H-pyrazole-4-carboxylate), imazosulfuron (2-chloro-N-[[(4,6-dimethoxy-2-pyrimidinyl)amino]carbonyl]imidazo[1,2-a]pyridine-3-sulfonamide), iodosulfuron-methyl (methyl 4-iodo-2-[[[[(4-methoxy-6-methyl-1,3,5-triazin-2-yl)amino]carbonyl]amino]sulfonyl]benzoate), mesosulfuron-methyl (methyl 2-[[[[(4,6-dimethoxy-2-pyrimidinyl)amino]carbonyl]amino]sulfonyl]-4-[[(methylsulfonyl)-amino]methyl]benzoate), metsulfuron-methyl (methyl 2-[[[[(4-methoxy-6-methyl-1,3,5-triazin-2-yl)amino]carbonyl]amino]sulfonyl]benzoate), nicosulfuron (2-[[[[(4,6-dimethoxy-2-pyrimidinyl)amino]carbonyl]amino]sulfonyl]-N,N-dimethyl-3-pyridinecarboxamide), oxasulfuron (3-oxetanyl 2-[[[[(4,6-dimethyl-2-pyrimidinyl)-amino]carbonyl]amino]sulfonyl]benzoate), primisulfuron-methyl (methyl 2-[[[[[4,6-bis(trifluoromethoxy)-2-pyrimidinyl]amino]carbonyl]amino]sulfonyl]benzoate), prosulfuron (N-[[(4-methoxy-6-methyl-1,3,5-triazin-2-yl)amino]carbonyl]-2-(3,3,3-trifluoropropyl)benzenesulfonamide), pyrazosulfuron-ethyl (ethyl 5-[[[[(4,6-dimethoxy-2-pyrimidinyl)amino]carbonyl]amino]sulfonyl]-1-methyl-1H-pyrazole-4- carboxylate), rimsulfuron (N-[[(4,6-dimethoxy-2-pyrimidinyl) amino]carbonyl]-3-(ethylsulfonyl)-2-pyridinesulfonamide), sulfometuron-methyl (methyl 2-[[[[(4,6-dimethyl-2-pyrimidinyl)amino]carbonyl]amino]sulfonyl]-benzoate), sulfosulfuron (N-[[(4,6-dimethoxy-2-pyrimidinyl)amino]carbonyl]-2-(ethylsulfonyl)imidazo[1,2-a]pyridine-3-sulfonamide), thifensulfuron-methyl (methyl 3-[[[[(4-methoxy-6-methyl-1,3,5-triazin-2-yl)amino]carbonyl]amino]sulfonyl]-2-thiophenecarboxylate), triasulfuron (2-(2-chloroethoxy)-N-[[(4-methoxy-6-methyl-1,3,5-triazin-2-yl)amino]carbonyl]benzenesulfonamide), tribenuron-methyl (methyl 2-[[[[N-(4-methoxy-6-methyl-1,3,5-triazin-2-yl)-N-methylamino]carbonyl]-amino]sulfonyl]benzoate), trifloxysulfuron (N-[[(4,6-dimethoxy-2-pyrimidinyl)amino]-carbonyl]-3-(2,2,2-trifluoroethoxy)-2-pyridinesulfonamide), triflusulfuron-methyl (methyl 2-[[[[[4-dimethylamino)-6-(2,2,2-trifluoroethoxy)-1,3,5-triazin-2-yl]amino]-carbonyl] amino]sulfonyl]-3-methylbenzoate) and tritosulfuron (N-[[[4-methoxy-6-(trifluoromethyl)-1,3,5-triazin-2-yl]amino] carbonyl]-2-(trifluoromethyl)benzene-sulfonamide).

The following triazolopyrimidine herbicides illustrate the triazolopyrimidines useful for this invention: cloransulam-methyl (methyl 3-chloro-2-[[(5-ethoxy-7-fluoro-[1,2,4]triazolo[1,5-c]pyrimidin-2-yl)sulfonyl]amino]benzoate, diclosulam (N-(2,6-dichlorophenyl)-5-ethoxy-7-fluoro[1,2,4] triazolo[1,5-c]pyrimidine-2-sulfonamide, florasulam (N-(2,6-difluorophenyl)-8-fluoro-5-methoxy[1,2,4]triazolo[1,5-c] pyrimidine-2-sulfonamide), flumetsulam (N-(2,6-difluorophenyl)-5-methyl[1,2,4]triazolo[1,5-a]pyrimidine-2-sulfonamide), metosulam (N-(2,6-dichloro-3-methylphenyl)-5,7-dimethoxy[1,2,4]triazolo[1,5-a] pyrimidine-2-sulfonamide), penoxsulam (2-(2,2-difluoroethoxy)-N-(5,8-dimethoxy[1,2,4]triazolo[1,5-c] pyrimidin-2-yl)-6-(trifluoromethyl)benzenesulfonamide) and pyroxsulam (N-(5,7-dimethoxy[1,2,4]triazolo[1,5-a]pyrimidin-2-yl)-2-methoxy-4-(trifluoromethyl)-3-pyridine-sulfonamide).

The following sulfonylaminocarbonyltriazolinone herbicides illustrate the sulfonylaminocarbonyltriazolinones useful for this invention: flucarbazone (4,5-dihydro-3-methoxy-4-methyl-5-oxo-N-[[2-(trifluoromethoxy)phenyl]sulfonyl]-1H-1,2,4-triazole-1-carboxamide) and procarbazone (methyl 2-[[[(4,5-dihydro-4-methyl-5-oxo-3-propoxy-1H-1,2,4-triazol-1-yl) carbonyl]amino]sulfonyl]benzoate).

Additional herbicides include phenmedipham, triazolinones, and the herbicides disclosed in WO2006/012981, herein incorporated by reference in its entirety.

The methods further comprise applying to the crop and the weeds in a field a sufficient amount of at least one herbicide to which the crop seeds or plants is tolerant, such as, for example, glyphosate, a hydroxyphenylpyruvatedioxygenase inhibitor (e.g., mesotrione or sulcotrione), a phytoene desaturase inhibitor (e.g., diflufenican), a pigment synthesis inhibitor, sulfonamide, imidazolinone, bialaphos, phosphinothricin, azafenidin, butafenacil, sulfosate, glufosinate, triazolopyrimidine, pyrimidinyloxy(thio)benzoate, or sulonylaminocarbonyltriazolinone, an acetyl Co-A carboxylase inhibitor such as quizalofop-P-ethyl, a synthetic auxin such as quinclorac, KIH-485, or a protox inhibitor to control the weeds without significantly damaging the crop plants.

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a maize plant. Thus, in some embodiments, a weed is a non-crop plant or a non-crop species, while in some embodiments, a weed is a crop species which is sought to be eliminated from a particular area, such as, for example, an inferior and/or non-transgenic maize plant in a field planted with maize event DP-098140-6, or a maize plant in a field planted with DP-098140-6. Weeds can be either classified into two major groups: monocots and dicots.

Many plant species can be controlled (i.e., killed or damaged) by the herbicides described herein. Accordingly, the methods of the invention are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass, and a non-selective herbicide resistant ryegrass. In some embodiments, the undesired plants are proximate the crop plants.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

In some embodiments, a maize DP-098140-6 plant of the invention is not significantly damaged by treatment with a particular herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000 or more grams or ounces (1 ounce=29.57 ml) of active ingredient or commercial product or herbicide formulation per acre or per hectare, whereas an appropriate control plant is significantly damaged by the same treatment.

In specific embodiments, an effective amount of an ALS inhibitor herbicide comprises at least about 0.1, 1, 5, 10, 25, 50, 75, 100, 150, 200, 250, 300, 350, 400, 450, 500, 600, 700, 750, 800, 850, 900, 950, 1000, 2000, 3000, 4000, 5000, or more grams or ounces (1 ounce=29.57 ml) of active ingredient per hectare. In other embodiments, an effective amount of an ALS inhibitor comprises at least about 0.1-50, about 25-75, about 50-100, about 100-110, about 110-120, about 120-130, about 130-140, about 140-150, about 150-200, about 200-500, about 500-600, about 600-800, about 800-1000, or greater grams or ounces (1 ounce=29.57 ml) of active ingredient per hectare. Any ALS inhibitor, for example, those listed in Table 1 can be applied at these levels.

In other embodiments, an effective amount of a sulfonylurea comprises at least 0.1, 1, 5, 10, 25, 50, 75, 100, 150, 200, 250, 300, 350, 400, 450, 500, 600, 700, 800, 900, 1000, 5000 or more grams or ounces (1 ounce=29.57 ml) of active ingredient per hectare. In other embodiments, an effective amount of a sulfonylurea comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) of active ingredient per hectare. Representative sulfonylureas that can be applied at this level are set forth in Table 1.

In other embodiments, an effective amount of a sulfonylaminocarbonyltriazolinones, triazolopyrimidines, pyrimidinyloxy(thio)benzoates, and imidazolinones can comprise at least about 0.1, 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1550, 1600, 1650, 1700, 1800, 1850, 1900, 1950, 2000, 2500, 3500, 4000, 4500, 5000 or greater grams or ounces (1 ounce=29.57 ml) active ingredient per hectare. In other embodiments, an effective amount of a sulfonyluminocarbonyltriazolines, triazolopyrimidines, pyrimidinyloxy(thio)benzoates, or imidazolinones comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) active ingredient per hectare.

Additional ranges of the effective amounts of herbicides can be found, for example, in various publications from University Extension services. See, for example, Bernards et al. (2006) *Guide for Weed Management in Nebraska* (www.ianrpubs.url.edu/sendlt/ec130); Regher et al. (2005) *Chemical Weed Control for Fields Crops, Pastures, Rangeland, and Noncropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

In some embodiments of the invention, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28, and 30 ounces of acid equivalent per acre at the lower end of the range of application and between 12, 14, 16, 18, 20, 22, 24, 26, 28, 30, and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). In some embodiments of the invention, a sulfonylurea herbicide is applied to a field and/or to at least one plant in a field at rates between 0.04 and 1.0 ounces of active ingredient per acre, or at rates between 0.1, 0.2, 0.4, 0.6, and 0.8 ounces of active ingredient per acre at the lower end of the range of application and between 0.2, 0.4, 0.6, 0.8, and 1.0 ounces of active ingredient per acre at the higher end of the range of application. (1 ounce=29.57 ml)

As is known in the art, glyphosate herbicides as a class contain the same active ingredient, but the active ingredient is present as one of a number of different salts and/or formulations. However, herbicides known to inhibit ALS vary in their active ingredient as well as their chemical formulations. One of skill in the art is familiar with the determination of the amount of active ingredient and/or acid equivalent present in a particular volume and/or weight of herbicide preparation.

In some embodiments, an ALS inhibitor herbicide is employed. Rates at which the ALS inhibitor herbicide is applied to the crop, crop part, seed or area of cultivation can be any of the rates disclosed herein. In specific embodiments, the rate for the ALS inhibitor herbicide is about 0.1 to about 5000 g ai/hectare, about 0.5 to about 300 g ai/hectare, or about 1 to about 150 g ai/hectare.

Generally, a particular herbicide is applied to a particular field (and any plants growing in it) no more than 1, 2, 3, 4, 5, 6, 7, or 8 times a year, or no more than 1, 2, 3, 4, or 5 times per growing season.

By "treated with a combination of" or "applying a combination of" herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. In some embodiments, weeds which are susceptible to each of the herbicides exhibit damage from treatment with each of the herbicides which is additive or synergistic. The application of each herbicide and/or chemical may be simultaneous or the applications may be at different times, so long as the desired effect is achieved. Furthermore, the application can occur prior to the planting of the crop.

The proportions of herbicides used in the methods of the invention with other herbicidal active ingredients in herbicidal compositions are generally in the ratio of 5000:1 to 1:5000, 1000:1 to 1:1000, 100:1 to 1:100, 10:1 to 1:10 or 5:1 to 1:5 by weight. The optimum ratios can be easily determined by those skilled in the art based on the weed control spectrum desired. Moreover, any combinations of ranges of the various herbicides disclosed in Table 1 can also be applied in the methods of the invention.

Thus, in some embodiments, the invention provides improved methods for selectively controlling weeds in a field wherein the total herbicide application may be less than 90%, 85%, 80%, 75%, 70%, 65%, 60%, 55%, 50%, 45%, 40%, 35%, 30%, 25%, 20%, 15%, 10%, 5%, or 1% of that used in other methods. Similarly, in some embodiments, the amount of a particular herbicide used for selectively controlling weeds in a field may be less than 90%, 85%, 80%, 75%, 70%, 65%, 60%, 55%, 50%, 45%, 40%, 35%, 30%, 25%, 20%, 15%, 10%, 5%, or 1% of the amount of that particular herbicide that would be used in other methods, i.e., methods not utilizing a plant of the invention.

In some embodiments, a DP-098140-6 maize plant of the invention benefits from a synergistic effect wherein the herbicide tolerance conferred by the GLYAT polypeptide and the zm-hra polypeptide is greater than expected from simply combining the herbicide tolerance conferred by each gene separately to a transgenic plant containing them individually. See, e.g., McCutchen et al. (1997) *J. Econ. Entomol.* 90: 1170-1180; Priesler et al. (1999) *J. Econ. Entomol.* 92: 598-603. As used herein, the terms "synergy," "synergistic," "synergistically" and derivations thereof, such as in a "synergistic effect" or a "synergistic herbicide combination" or a "synergistic herbicide composition" refer to circumstances under which the biological activity of a combination of herbicides, such as at least a first herbicide and a second herbicide, is greater than the sum of the biological activities of the individual herbicides. Synergy, expressed in terms of a "Synergy Index (SI)," generally can be determined by the method described by Kull et al. *Applied Microbiology* 9, 538 (1961). See also Colby "Calculating Synergistic and Antagonistic Responses of Herbicide Combinations," *Weeds* 15, 20-22 (1967).

In other instances, the herbicide tolerance conferred on a DP-098140-6 plant of the invention is additive; that is, the herbicide tolerance profile conferred by the herbicide tolerance genes is what would be expected from simply combining the herbicide tolerance conferred by each gene separately to a transgenic plant containing them individually. Additive and/or synergistic activity for two or more herbicides against key weed species will increase the overall effectiveness and/or reduce the actual amount of active ingredient(s) needed to control said weeds. Where such synergy is observed, the plant of the invention may display tolerance to a higher dose or rate of herbicide and/or the plant may display tolerance to additional herbicides or other chemicals beyond those to which it would be expected to display tolerance. For example, a DP-098140-6 maize plant may show tolerance to organophosphate compounds such as insecticides and/or inhibitors of 4-hydroxyphenylpyruvate dioxygenase.

Thus, for example, the DP-098140-6 maize plants of the invention can exhibit greater than expected tolerance to various herbicides, including but not limited to glyphosate, ALS inhibitor chemistries, and sulfonylurea herbicides. The DP-098140-6 maize plant plants of the invention may show tolerance to a particular herbicide or herbicide combination that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, or 500% or more higher than the tolerance of an appropriate control plant that contains only a single herbicide tolerance gene which confers tolerance to the same herbicide or herbicide combination. Thus, DP-098140-6 maize plants may show decreased damage from the same dose of herbicide in comparison to an appropriate control plant, or they may show the same degree of damage in response to a much higher dose of herbicide than the control plant. Accordingly, in specific embodiments, a particular herbicide used for selectively containing weeds in a field is more than 1%, 5%, 10%, 15%, 20%, 25%, 30%, 35%, 40%, 45%, 50%, 60%, 70%, 80%, 90%, 100% or greater than the amount of that particular herbicide that would be used in other methods, i.e., methods not utilizing a plant of the invention.

In the same manner, in some embodiments, a DP-098140-6 maize plant of the invention shows improved tolerance to a particular formulation of a herbicide active ingredient in comparison to an appropriate control plant. Herbicides are sold commercially as formulations which typically include other ingredients in addition to the herbicide active ingredient; these ingredients are often intended to enhance the efficacy of the active ingredient. Such other ingredients can include, for example, safeners and adjuvants (see, e.g., Green and Foy (2003) "Adjuvants: Tools for Enhancing Herbicide Performance," in *Weed Biology and Management*, ed. Inderjit (Kluwer Academic Publishers, The Netherlands)). Thus, a DP-098140-6 maize plant of the invention can show tolerance to a particular formulation of a herbicide (e.g., a particular commercially available herbicide product) that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, 500%, 600%, 700%, 800%, 900%, 1000%, 1100%, 1200%, 1300%, 1400%, 1500%, 1600%, 1700%, 1800%, 1900%, or 2000% or more higher than the tolerance of an appropriate control plant that contains only a single herbicide tolerance gene which confers tolerance to the same herbicide formulation.

In some embodiments, a DP-098140-6 maize plant of the invention shows improved tolerance to a herbicide or herbicide class to which at least one other herbicide tolerance gene confers tolerance as well as improved tolerance to at least one other herbicide or chemical which has a different mechanism or basis of action than either glyphosate or the herbicide corresponding to said at least one other herbicide tolerance gene. This surprising benefit of the invention finds use in methods of growing crops that comprise treatment with various combinations of chemicals, including, for example, other chemicals used for growing crops. Thus, for example, a DP-098140-6 maize plant may also show improved tolerance to chlorpyrifos, a systemic organophosphate insecticide. Thus, the invention also provides a DP-098140-6 maize plant that confers tolerance to glyphosate (i.e., a GLYAT gene) and a sulfonylurea herbicide tolerance gene which shows improved tolerance to chemicals which affect the cytochrome P450 gene, and methods of use thereof. In some embodiments, the DP-098140-6 maize plants also show improved tolerance to dicamba. In these embodiments, the improved tolerance to dicamba may be evident in the presence of glyphosate and a sulfonylurea herbicide.

In other methods, a herbicide combination is applied over a DP-098140-6 maize plant, where the herbicide combination produces either an additive or a synergistic effect for controlling weeds. Such combinations of herbicides can allow the application rate to be reduced, a broader spectrum of undesired vegetation to be controlled, improved control of the undesired vegetation with fewer applications, more rapid onset of the herbicidal activity, or more prolonged herbicidal activity.

An "additive herbicidal composition" has a herbicidal activity that is about equal to the observed activities of the individual components. A "synergistic herbicidal combination" has a herbicidal activity higher than what can be expected based on the observed activities of the individual components when used alone. Accordingly, the presently disclosed subject matter provides a synergistic herbicide combination, wherein the degree of weed control of the mixture exceeds the sum of control of the individual herbicides. In some embodiments, the degree of weed control of the mixture exceeds the sum of control of the individual herbicides by any statistically significant amount including, for example, about 1% to 5%, about 5% to about 10%, about 10% to about 20%, about 20% to about 30%, about 30% to 40%, about 40% to about 50%, about 50% to about 60%, about 60% to about 70%, about 70% to about 80%, about 80% to about 90%, about 90% to about 100%, about 100% to 120% or greater. Further, a "synergistically effective amount" of a herbicide refers to the amount of one herbicide necessary to elicit a synergistic effect in another herbicide present in the herbicide composition. Thus, the term "synergist," and derivations thereof, refer to a substance that enhances the activity of an active ingredient (ai), i.e., a substance in a formulation from which a biological effect is obtained, for example, a herbicide.

Accordingly, in some embodiments, the presently disclosed subject matter provides a method for controlling weeds in an area of cultivation. In some embodiments, the method comprises: (a) planting the area with a DP-098140-6 crop seeds or crop plants; and (b) applying to the weed, the crop plants, a crop part, the area of cultivation, or a combination thereof, an effective amount of a herbicide composition comprising at least one of a synergistically effective amount of glyphosate and a synergistically effective amount of an ALS inhibitor (for example, but not limited to, a sulfonylurea herbicide), or agriculturally suitable salts thereof, wherein at least one of: (i) the synergistically effective amount of the glyphosate is lower than an amount of glyphosate required to control the weeds in the absence of the sulfonylurea herbicide; (ii) the synergistically effective amount of the ALS inhibitor herbicide is lower than an amount of the ALS inhibitor required to control the weeds in the absence of glyphosate; and (iii) combinations thereof, and wherein the effective amount of the herbicide composition is tolerated by the crop seeds or crop plants and controls the weeds in the area of cultivation.

In some embodiments, the herbicide composition used in the presently disclosed method for controlling weeds comprises a synergistically effective amount of glyphosate and a sulfonylurea herbicide. In further embodiments, the presently disclosed synergistic herbicide composition comprises glyphosate and a sulfonylurea herbicide selected from the group consisting of metsulfuron-methyl, chlorsulfuron, and triasulfuron.

In particular embodiments, the synergistic herbicide combination further comprises an adjuvant such as, for example, an ammonium sulfate-based adjuvant, e.g., ADD-UP® (Wenkem S.A., Halfway House, Midrand, South Africa). In additional embodiments, the presently disclosed synergistic herbicide compositions comprise an additional herbicide, for example, an effective amount of a pyrimidinyloxy(thio)benzoate herbicide. In some embodiments, the pyrimidinyloxy(thio)benzoate herbicide comprises bispyribac, e.g., (VELOCITY®, Valent U.S.A. Corp., Walnut Creek, Calif., United States of America), or an agriculturally suitable salt thereof.

In some embodiments of the presently disclosed method for controlling undesired plants, the glyphosate is applied pre-emergence, post-emergence or pre- and post-emergence to the undesired plants or plant crops; and/or the ALS inhibitor herbicide (i.e., the sulfonylurea herbicide) is applied pre-emergence, post-emergence or pre- and post-emergence to the undesired plants or plant crops. In other embodiments, the glyphosate and/or the ALS inhibitor herbicide (i.e., the sulfonylurea herbicide) are applied together or are applied separately. In yet other embodiments, the synergistic herbicide composition is applied, e.g. step (b) above, at least once prior to planting the crop(s) of interest, e.g., step (a) above.

Weeds that can be difficult to control with glyphosate alone in fields where a crop is grown (such as, for example, a maize crop) include but are not limited to the following: horseweed (e.g., *Conyza canadensis*); rigid ryegrass (e.g., *Lolium rigidum*); goosegrass (e.g., *Eleusine indica*); Italian ryegrass (e.g., *Lolium multiflorum*); hairy fleabane (e.g., *Conyza bonariensis*); buckhorn plantain (e.g., *Plantago lanceolata*); common ragweed (e.g., *Ambrosia artemisifolia*); morning glory (e.g., *Ipomoea* spp.); waterhemp (e.g., *Amaranthus* spp.); field bindweed (e.g., *Convolvulus arvensis*); yellow nutsedge (e.g., *Cyperus esculentus*); common lambsquarters (e.g., *Chenopodium album*); wild buckwheat (e.g., *Polygonium convolvulus*); velvetleaf (e.g., *Abutilon theophrasti*); kochia (e.g., *Kochia scoparia*); and Asiatic dayflower (e.g., *Commelina* spp.). In areas where such weeds are found, the DP-098140-6 maizes are particularly useful in allowing the treatment of a field (and therefore any crop growing in the field) with combinations of herbicides that would cause unacceptable damage to crop plants that did not contain both of these polynucleotides. Plants of the invention that are tolerant to glyphosate and other herbicides such as, for example, sulfonylurea, imidazolinone, triazolopyrimidine, pyrimidinyl(thio)benzoate, and/or sulfonylaminocarbonyltriazolinone herbicides in addition to being tolerant to at least one other herbicide with a different mode of action or site of action are particularly useful in situations where weeds are tolerant to at least two of the same herbicides to which the plants are tolerant. In this manner, plants of the invention make possible improved control of weeds that are tolerant to more than one herbicide.

For example, some commonly used treatments for weed control in fields where current commercial crops (including, for example, maizes) are grown include glyphosate and, optionally, 2,4-D; this combination, however, has some disadvantages. Particularly, there are weed species that it does not control well and it also does not work well for weed control in cold weather. Another commonly used treatment for weed control in maize fields is the sulfonylurea herbicide chlorimuron-ethyl, which has significant residual activity in the soil and thus maintains selective pressure on all later-emerging weed species, creating a favorable environment for the growth and spread of sulfonylurea-resistant weeds. However, the DP-098140-6 maize can be treated with herbicides (e.g., chlorimuron-ethyl) and combinations of herbicides that would cause unacceptable damage to standard plant varieties. Thus, for example, fields containing the DP-098140-6 maize can be treated with sulfonylurea, imidazolinone, triazolopyrimidines, pyrimidiny(thio)benzoates, and/or sulfonylaminocarbonyltriazonlinone such as the sulfonylurea chlorimuron-ethyl, either alone or in combination with other herbicides. For example, fields containing maize plants of the invention can be treated with a combination of glyphosate and tribenuron-methyl (available commercially as Express®). This combination has several advantages for weed control under some circumstances, including the use of herbicides with different modes of action and the use of herbicides having a relatively short period of residual activity in the soil. A herbicide having a relatively short period of residual activity is desirable, for example, in situations where it is important to reduce selective pressure that would favor the growth of herbicide-tolerant weeds. Of course, in any particular situation where weed control is required, other considerations may be more important, such as, for example, the need to prevent the development of and/or appearance of weeds in a field prior to planting a crop by using a herbicide with a relatively long period of residual activity. The DP-098140-6 maize plants can also be treated with herbicide combinations that include at least one of nicosulfuron, metsulfuron-methyl, tribenuron-methyl, thifensulfuron-methyl, and/or rimsulfuron. Treatments that include both tribenuron-methyl and thifensulfuron-methyl may be particularly useful.

Other commonly used treatments for weed control in fields where current commercial varieties of crops (including, for example, maizes) are grown include the sulfonylurea herbicide thifensulfuron-methyl (available commercially as Harmony GT®). However, one disadvantage of thifensulfuron-methyl is that the higher application rates required for consistent weed control often cause injury to a crop growing in the same field. The DP-098140-6 maize plants can be treated with a combination of glyphosate and thifensulfuron-methyl, which has the advantage of using herbicides with different modes of action. Thus, weeds that are resistant to either herbicide alone are controlled by the combination of the two herbicides, and the DP-098140-6 maize plants of the invention are not significantly damaged by the treatment.

Other herbicides which are used for weed control in fields where current commercial varieties of crops (including, for example, maizes) are grown are the triazolopyrimidine herbicide cloransulam-methyl (available commercially as FirstRate®) and the imidazolinone herbicide imazaquin (available commercially as Sceptor®). When these herbicides are used individually they may provide only marginal control of weeds. However, fields containing the DP-098140-6 maize can be treated, for example, with a combination of glyphosate (e.g., Roundup® (glyphosate isopropylamine salt)), imazapyr (currently available commercially as Arsenal®), chlorimuron-ethyl (currently available commercially as Classic®), quizalofop-P-ethyl (currently available commercially as Assure II®), and fomesafen (currently available commercially as Flexstar®). This combination has the advantage of using herbicides with different modes of action. Thus, weeds that are tolerant to just one or several of these herbicides are controlled by the combination of the five herbicides, and the DP-098140-6 maizes are not significantly damaged by treatment with this herbicide combination. This combination provides an extremely broad spectrum of protection against the type of herbicide-tolerant weeds that might be expected to arise and spread under current weed control practices.

Fields containing the DP-098140-6 maize plants may also be treated, for example, with a combination of herbicides including glyphosate, rimsulfuron, and dicamba or mesotrione. This combination may be particularly useful in controlling weeds which have developed some tolerance to herbicides which inhibit ALS. Another combination of herbicides which may be particularly useful for weed control includes glyphosate and at least one of the following: metsulfuron-methyl (commercially available as Ally®), imazapyr (commercially available as Arsenal®), imazethapyr, imazaquin, and sulfentrazone. It is understood that any of the combinations discussed above or elsewhere herein may also be used to treat areas in combination with any other herbicide or agricultural chemical.

Some commonly-used treatments for weed control in fields where current commercial crops (including, for example, maize) are grown include glyphosate (currently available commercially as Roundup®), rimsulfuron (currently available commercially as Resolve® or Matrix®), dicamba (commercially available as Clarity®), atrazine, and mesotrione (commercially available as Callisto®). These herbicides are sometimes used individually due to poor crop tolerance to multiple herbicides. Unfortunately, when used individually, each of these herbicides has significant disadvantages. Particularly, the incidence of weeds that are tolerant to individual herbicides continues to increase, rendering glyphosate less effective than desired in some situations. Rimsulfuron provides better weed control at high doses which can cause injury to a crop, and alternatives such as dicamba are often more expensive than other commonly-used herbicides. However, DP-098140-6 maize can be treated with herbicides and combinations of herbicides that would cause unacceptable damage to standard plant varieties, including combinations of herbicides that comprise rimsulfuron and/or dicamba. Other suitable combinations of herbicides for use with DP-098140-6 maize plants of the invention include glyphosate, sulfonylurea, imidazolinone, triazolopyrimidine, pryimidinyloxy(thio)benzoates, and/or sulfonylaminocarbonyl-triazonlinone herbicides, including, for example, and at least one of the following: metsulfuron-methyl, tribenuron-methyl, chlorimuron-ethyl, imazethapyr, imazapyr, and imazaquin.

For example, DP-098140-6 maize plants can be treated with a combination of glyphosate and rimsulfuron, or a combination or rimsulfuron and at least one other herbicide. DP-098140-6 maize plants can also be treated with a combination of glyphosate, rimsulfuron, and dicamba, or a combination of glyphosate, rimsulfuron, and at least one other herbicide. In some embodiments, at least one other herbicide has a different mode of action than both glyphosate and rimsulfuron. The combination of glyphosate, rimsulfuron, and dicamba has the advantage that these herbicides have different modes of action and short residual activity, which decreases the risk of incidence and spread of herbicide-tolerant weeds.

Some commonly-used treatments for weed control in fields where current commercial crops are grown include glyphosate (currently available commercially as Roundup®), chlorimuron-ethyl, tribenuron-methyl, rimsulfuron (currently available commercially as Resolve® or Matrix®), imazethapyr, imazapyr, and imazaquin. Unfortunately, when used individually, each of these herbicides has significant disadvantages. Particularly, the incidence of weeds that are tolerant to individual herbicides continues to increase, rendering each individual herbicide less effective than desired in some situations. However, DP-098140-6 maize can be treated with a combination of herbicides that would cause unacceptable damage to standard plant varieties, including combinations of herbicides that include at least one of those mentioned above.

In the methods of the invention, a herbicide may be formulated and applied to an area of interest such as, for example, a field or area of cultivation, in any suitable manner. A herbicide may be applied to a field in any form, such as, for example, in a liquid spray or as solid powder or granules. In specific embodiments, the herbicide or combination of herbicides that are employed in the methods comprise a tankmix or a premix. A herbicide may also be formulated, for example, as a "homogenous granule blend" produced using blends technology (see, e.g., U.S. Pat. No. 6,022,552, entitled "Uniform Mixtures of Pesticide Granules"). The blends technology of U.S. Pat. No. 6,022,552 produces a nonsegregating blend (i.e., a "homogenous granule blend") of formulated crop protection chemicals in a dry granule form that enables delivery of customized mixtures designed to solve specific problems. A homogenous granule blend can be shipped, handled, subsampled, and applied in the same manner as traditional premix products where multiple active ingredients are formulated into the same granule.

Briefly, a "homogenous granule blend" is prepared by mixing together at least two extruded formulated granule products. In some embodiments, each granule product comprises a registered formulation containing a single active ingredient which is, for example, a herbicide, a fungicide, and/or an insecticide. The uniformity (homogeneity) of a "homogenous granule blend" can be optimized by controlling the relative sizes and size distributions of the granules used in the blend. The diameter of extruded granules is controlled by the size of the holes in the extruder die, and a centrifugal sifting process may be used to obtain a population of extruded granules with a desired length distribution (see, e.g., U.S. Pat. No. 6,270,025).

A homogenous granule blend is considered to be "homogenous" when it can be subsampled into appropriately sized aliquots and the composition of each aliquot will meet the required assay specifications. To demonstrate homogeneity, a large sample of the homogenous granule blend is prepared and is then subsampled into aliquots of greater than the minimum statistical sample size.

In non-limiting embodiments, the 3560.4.5.3 maize plant can be treated with herbicides (e.g., chlorimuron-ethyl and combinations of other herbicides that without the DP-098140-6 event would have caused unacceptable crop response to plant varieties without the glyphosate/ALS inhibitor genetics). Thus, for example, fields planted with and containing DP-098140-6 maizes can be treated with sulfonylurea, imidazolinone, triazolopyrimidine, pyrimidinyl(thio) benzoate, and/or sulfonylaminocarbonyltriazonlinone herbicides, either alone or in combination with other herbicides. Since ALS inhibitor chemistries have different herbicidal attributes, blends of ALS plus other chemistries will provide superior weed management strategies including varying and increased weed spectrum, the ability to provide specified residual activity (SU/ALS inhibitor chemistry with residual activity leads to improved foliar activity which leads to a wider window between glyphosate applications, as well as, an added period of control if weather conditions prohibit timely application).

Blends also afford the ability to add other agrochemicals at normal, labeled use rates such as additional herbicides (a $3^{rd}/4^{th}$ mechanism of action), fungicides, insecticides, plant growth regulators and the like thereby saving costs associated with additional applications.

Any herbicide formulation applied over the DP-098140-6 maize plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. For additional guidance regarding the art of formulation, see T. S. Woods, "The Formulator's Toolbox—Product Forms for Modern Agriculture" *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989, each of which is incorporated herein by reference in their entirety.

The methods of the invention further allow for the development of herbicide combinations to be used with the DP-098140-6 maize plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, seed of the crop or area of cultivation.

In some embodiments, the herbicide applied to the DP-098140-6 maize plants of the invention serves to prevent the initiation of growth of susceptible weeds and/or serve to cause damage to weeds that are growing in the area of interest. In some embodiments, the herbicide or herbicide mixture exert these effects on weeds affecting crops that are subsequently planted in the area of interest (i.e., field or area of cultivation). In the methods of the invention, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention. Thus, methods of the invention encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein).

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

Thus, the invention provides improved methods of growing a crop and/or controlling weeds such as, for example, "pre-planting burn down," wherein an area is treated with herbicides prior to planting the crop of interest in order to better control weeds. The invention also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The methods of the invention encompass the use of simultaneous and/or sequential applications of multiple classes of herbicides. In some embodiments, the methods of the invention involve treating a plant of the invention and/or an area of interest (e.g., a field or area of cultivation) and/or weed with just one herbicide or other chemical such as, for example, a sulfonylurea herbicide.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area. The stages of growth and/or development of plants are known in the art. For example, corn plants normally progress through the following vegetative stages VE (emergence); V1 (first leaf); V2 (second leaf); V3 (third leaf); V(n) (Nth/leaf); and VT (tasseling). Progression of maize through the reproductive phase is as follows: R1 (silking); R2 (blistering); R3 (milk); R4 (dough); R5 (dent); and R6 (physiological maturity). Cotton plants normally progress through $V_E$ (emergence), $V_C$ (cotyledon), $V_1$ (first true leaf), and $V_2$ to $V_N$. Then, reproductive stages beginning around $V_{14}$ include $R_1$ (beginning bloom), $R_2$ (full bloom), $R_3$ (beginning boll), $R_4$ (cutout, boll development), $R_5$ (beginning maturity, first opened boll), $R_6$ (maturity, 50% opened boll), and $R_7$ (full maturity, 80-90% open bolls). Thus, for example, the time at which a herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

In some embodiments, the DP-098140-6 maize plants of the invention show improved tolerance to postemergence herbicide treatments. For example, plants of the invention may be tolerant to higher doses of herbicide, tolerant to a broader range of herbicides (i.e., tolerance to more ALS inhibitor chemistries), and/or may be tolerant to doses of herbicide applied at earlier or later times of development in comparison to an appropriate control plant. For example, in some embodiments, the DP-098140-6 maize plants of the invention show an increased resistance to morphological defects that are known to result from treatment at particular stages of development. Thus, for example, a phenomenon known as "ear pinch" often results when maize plants are treated with herbicide at a stage later than V5, V6, V7, V8, V9, V10, V11, V12, V13, or a later stage, whereas the glyphosate/ALS inhibitor-tolerant plants of the invention show a decreased incidence of "ear pinch" when treated at the same stage. Thus, the glyphosate/ALS inhibitor-tolerant plants of the invention find use in methods involving herbicide treatments at later stages of development than were previously feasible. Thus, plants of the invention may be treated with a particular herbicide that causes morphological defects in a control plant treated at the same stage of development, but the glyphosate/ALS inhibitor-tolerant plants of the invention will not be significantly damaged by the same treatment.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of a herbicide; for example, generally, glyphosate has very little or no soil residual activity, while herbicides that act to inhibit ALS vary in their residual activity levels. Residual activities for various herbicides are known in the art, and are also known to vary with various environmental factors such as, for example, soil moisture levels, temperature, pH, and soil composition (texture and organic matter). The DP-098140-6 maize plants find particular use in methods of growing a crop where improved tolerance to residual activity of a herbicide is beneficial.

For example, in one embodiment, the DP-098140-6 maize plants have an improved tolerance to glyphosate as well as to ALS inhibitor chemistries (such as sulfonylurea herbicides) when applied individually, and further provide improved tolerance to combinations of herbicides such as glyphosate and/or ALS inhibitor chemistries. Moreover, the transgenic plants of the invention provide improved tolerance to treatment with additional chemicals commonly used on crops in conjunction with herbicide treatments, such as safeners, adjuvants such as ammonium sulfonate and crop oil concentrate, and the like.

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the invention can involve the use of herbicides in combination with herbicide safeners such as benoxacor, BCS (1-bromo-4-[(chloromethyl) sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this invention, or applied as seed treatments. Therefore an aspect of the present invention relates to the use of a mixture comprising glyphosate, at least one other herbicide, and an antidotally effective amount of a herbicide safener.

Seed treatment is particularly useful for selective weed control, because it physically restricts antidoting to the crop plants. Therefore a particularly useful embodiment of the present invention is a method for selectively controlling the growth of weeds in a field comprising treating the seed from which the crop is grown with an antidotally effective amount of safener and treating the field with an effective amount of herbicide to control weeds. Antidotally effective amounts of safeners can be easily determined by one skilled in the art through simple experimentation. An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

In specific embodiments, the herbicide or herbicide combination applied to the plant of the invention acts as a safener. In this embodiment, a first herbicide or a herbicide mixture is applied at an antidotally effect amount to the plant. Accordingly, a method for controlling weeds in an area of cultivation is provided. The method comprises planting the area with crop seeds or plants which comprise a first polynucleotide encoding a polypeptide that can confer tolerance to glyphosate operably linked to a promoter active in a plant; and, a second polynucleotide encoding an ALS inhibitor-tolerant polypeptide operably linked to a promoter active in a plant. A combination of herbicides comprising at least an effective amount of a first and a second herbicide is applied to the crop, crop part, weed or area of cultivation thereof. The effective amount of the herbicide combination controls weeds; and, the effective amount of the first herbicide is not tolerated by the crop when applied alone when compared to a control crop that has not been exposed to the first herbicide; and, the effective amount of the second herbicide is sufficient to produce a safening effect, wherein the safening effect provides an increase in crop tolerance upon the application of the first and the second herbicide when compared to the crop tolerance when the first herbicide is applied alone.

In specific embodiments, the combination of safening herbicides comprises a first ALS inhibitor and a second ALS inhibitor. In other embodiments, the safening effect is achieved by applying an effective amount of a combination of glyphosate and at least one ALS inhibitor chemistry. In still other embodiments, a safening affect is achieved when the DP-098140-6 maize crops, crop part, crop seed, weed, or area of cultivation is treated with at least one herbicide from the sulfonylurea family of chemistries in combination with at least one herbicide from the ALS family of chemistries (such as, for example, an imidazolinone).

Such mixtures provides increased crop tolerance (i.e., a decrease in herbicidal injury). This method allows for increased application rates of the chemistries post or pre-treatment. Such methods find use for increased control of unwanted or undesired vegetation. In still other embodiments, a safening affect is achieved when the DP-098140-6 maize crops, crop part, crop seed, weed, or area of cultivation is treated with at least one herbicide from the sulfonylurea family of chemistry in combination with at least one herbicide from the imidazolinone family. This method provides increased crop tolerance (i.e., a decrease in herbicidal injury). In specific embodiments, the sulfonylurea comprises rimsulfuron and the imidazolinone comprises imazethapyr. In other embodiments, glyphosate is also applied to the crop, crop part, or area of cultivation.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

In addition, methods of the invention can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. Examples of such agricultural protectants which can be used in methods of the invention include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. The weight ratios of these various mixing partners to other compositions (e.g., herbicides) used in the methods of the invention typically are between 100:1 and 1:100, or between 30:1 and 1:30, between 10:1 and 1:10, or between 4:1 and 1:4.

The present invention also pertains to a composition comprising a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), metrafenone (AC375839), myclobutanil, neo-asozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods of the invention may also comprise the use of plants genetically transformed to express proteins toxic to invertebrate pests (such as *Bacillus thuringiensis* delta-endotoxins). In such embodiments, the effect of exogenously applied invertebrate pest control compounds may be synergistic with the expressed toxin proteins.

General references for these agricultural protectants include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this invention can also provide a broader spectrum of plant protection and be advantageous for resistance management.

Thus, methods of the invention employ a herbicide or herbicide combination and may further comprise the use of insecticides and/or fungicides, and/or other agricultural chemicals such as fertilizers. The use of such combined treatments of the invention can broaden the spectrum of activity against additional weed species and suppress the proliferation of any resistant biotypes.

Methods of the invention can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as Bacillus cereus strain BP01.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXPERIMENTAL

The following abbreviations are used in describing the present invention.

| | |
|---|---|
| ALS | acetolactate synthase protein |
| bp | base pair |
| glyat4621 | glyphosate acetyltransferase gene |
| GLYAT4621 | glyphosate acetyltransferase protein |
| zm-als | wild type acetolactate synthase gene from maize |
| zm-hra | modified version of acetolactate synthase gene from maize |
| kb | kilobase |
| PCR | polymerase chain reaction |
| UTR | untranslated region |

Example 1

Insert and Flanking Border Sequence Characterization of Maize Event DP-098140-6

Maize (Zea mays) has been modified by the insertion of the glyphosate acetyltransferase gene (glyat4621) derived from Bacillus licheniformis and a modified version of the maize acetolactate synthase gene (zm-hra). The vector used for the genetic modification was a plasmid of the Agrobacterium tumefaciens, strain LBA4404, whose pathogenicity has been disarmed by removing its native T-DNA. Maize event DP-098140-6 was obtained by Agrobacterium-mediated transformation with plasmid PHP24279 (FIG. 1). The T-DNA of plasmid PHP24279 contains two expression cassettes as further described hereafter.

Immature embryos of maize were aseptically removed from the developing caryopsis and treated with Agrobacterium tumefaciens strain LBA4404 containing GLYAT4621 and ZM-HRA expression cassettes. After a period of embryo and Agrobacterium co-cultivation on solid culture medium without glyphosate present, the embryos were transferred to fresh selection medium that contained antibiotics and glyphosate. The antibiotics kill any remaining Agrobacterium. The selection medium is stimulatory to maize somatic embryogenesis and selective for those cells that contain an integrated glyat4621 gene cassette. Therefore, calli that survive glyphosate proliferate and produce embryogenic tissue which is presumably genetically transformed. Callus samples were taken for molecular analysis to verify the presence of the transgenes by PCR. The embryonic tissue is then manipulated to regenerate whole transgenic plants with glyphosate present, which are transferred to the greenhouse. T0 plants were then subjected to glyphosate and sulfonylurea spray at different concentrations. Surviving plants were crossed with inbred lines to obtain seeds for further evaluation.

The glyat4621 gene was derived from the soil bacterium Bacillus licheniformis and was synthesized by a gene shuffling process to optimize the acetyltransferase activity of the GLYAT4621 enzyme (Castle et al. (2004) Science 304:1151-1154). The ZM-HRA expression cassette contains a modified maize acetolactate synthase gene, zm-hra (Zea mays-highly resistant allele), encoding the ZM-HRA protein, which confers tolerance to a range of ALS-inhibiting herbicides, such as sulfonylureas.

Figure 3:
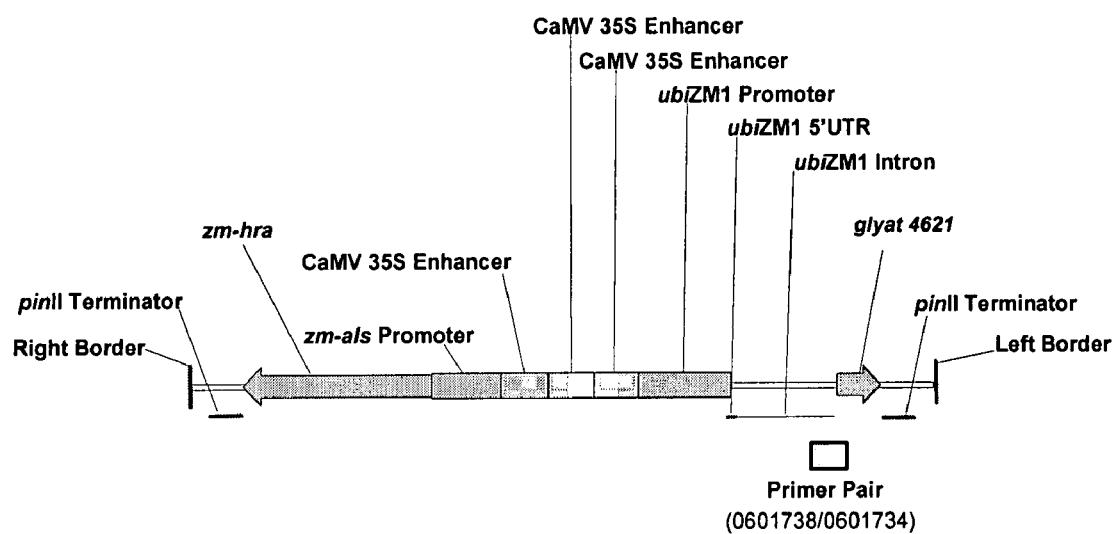
FIG. 3 shows the map of T-DNA from PHP24279 and displays the positions of primers 0601738 and 0601734 are shown.
Figure 4:
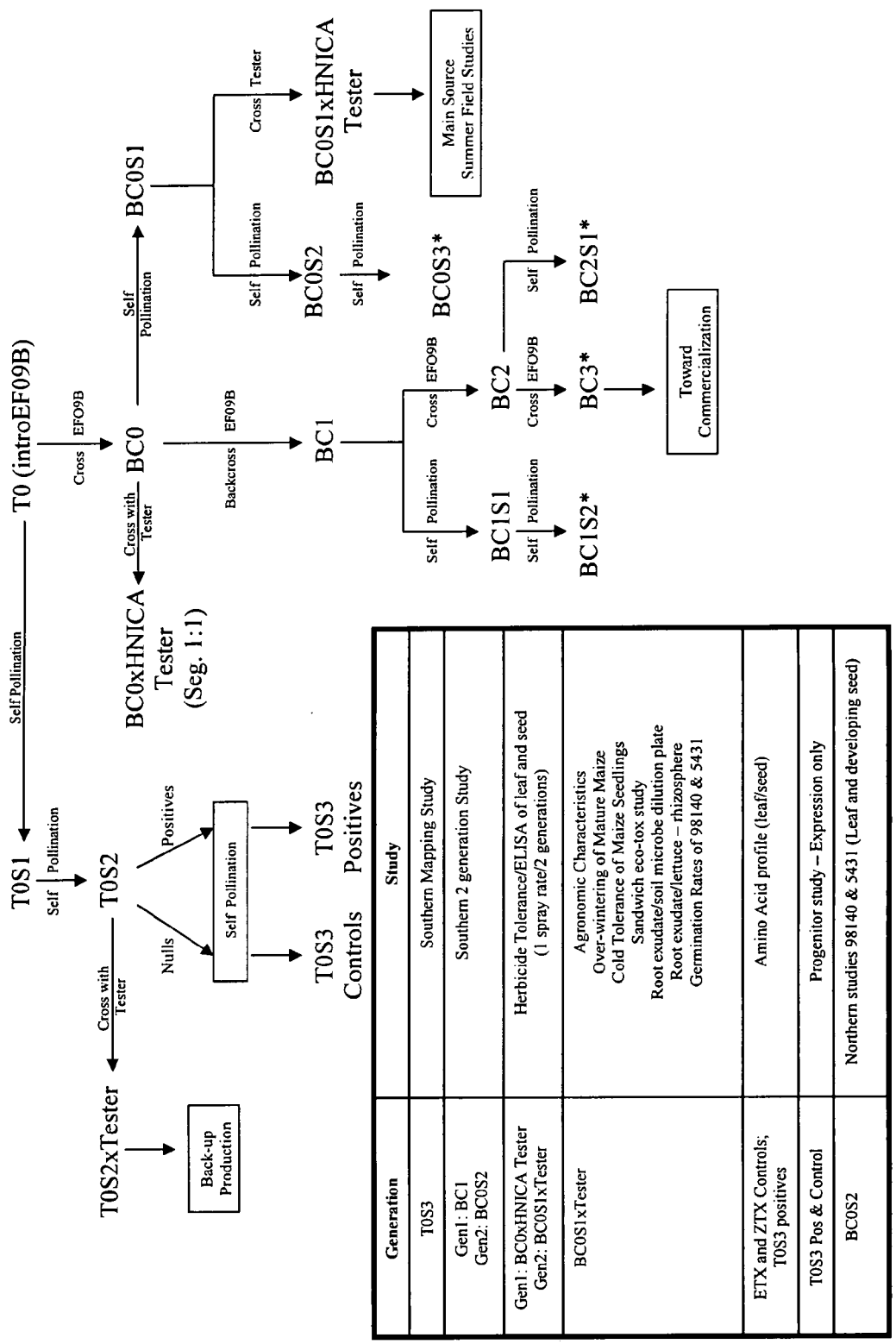
FIG. 4 provides a breeding diagram for event DP-098140-6.

The inserted T-DNA (FIGS. 2 and 3) from this plasmid contains the glyat4621 gene cassette and the zm-hra gene cassette, in reverse orientation. The expression of the glyat4621 gene is controlled by the ubiquitin regulatory region from maize (ubiZM1 promoter, 5'UTR, and intron (Christensen et al. (1992)) and the pinII terminator (An et al. (1989) Plant Cell 1:115-122). The expression of the zm-hra gene is controlled by the native maize acetolactate synthase promoter (zm-als promoter) (Fang et al. (2000)). The terminator for the zm-hra gene is the 3' terminator sequence from the proteinase inhibitor II gene of Solanum tuberosum (pinII terminator). Upstream of both cassettes are three copies of the enhancer region from the cauliflower mosaic virus (CaMV 35S enhancer, U.S. application Ser. No. 11/508,045, herein incorporated by reference) providing expression enhancement to both cassettes on the T-DNA. A summary of the T-DNA region of plasmid PHP24279 is shown in Table 3. The genetic elements of plasmid PHP24279 used in the creation of DP-098140-6 are shown in Table 4.

TABLE 3

Description of Genetic Elements in the T-DNA of PHP24279

| Location on T-DNA (base pair position) | Genetic Element | Size (base pairs) | Description |
|---|---|---|---|
| 1 to 25 | Right Border | 25 | T-DNA Right Border region, from Ti plasmid of Agrobacterium tumefaciens |
| 26 to 177 | Ti Plasmid Region | 152 | Non-functional sequence from Ti plasmid of A. tumefaciens |

TABLE 3-continued

Description of Genetic Elements in the T-DNA of PHP24279

| Location on T-DNA (base pair position) | Genetic Element | Size (base pairs) | Description |
|---|---|---|---|
| 178 to 210 | Polylinker Region | 33 | Region required for cloning genetic elements |
| 211 to 521 | pinII Terminator | 311 | Terminator region from *Solanum tuberosum* proteinase inhibitor II gene (Keil et al., 1986; An et al., 1989). (reverse orientation) |
| 522 to 537 | Polylinker Region | 33 | Region required for cloning genetic elements |
| 538 to 2454 | zm-hra Gene | 1917 | Modified endogenous *Zea mays* acetolactate synthase gene (Fang et al., 1992). (reverse orientation) |
| 2455 to 3115 | zm-als Promoter | 661 | Promoter region from *Zea mays* acetolactate synthase gene (Fang et al., 1992). (reverse orientation) |
| 3116 to 3189 | Polylinker Region | 74 | Region required for cloning genetic elements |
| 3190 to 3625 | CaMV 35S Enhancer | 436 | Enhancer region from the Cauliflower Mosaic Virus genome (Franck et al., 1980; Odell et al., 1985). |
| 3626 to 3648 | Polylinker Region | 23 | Region required for cloning genetic elements |
| 3649 to 4086 | CaMV 35S Enhancer | 438 | Enhancer region from the Cauliflower Mosaic Virus genome (Franck et al., 1980; Odell et al., 1985). |
| 4087 to 4093 | Polylinker Region | 7 | Region required for cloning genetic elements |
| 4094 to 4531 | CaMV 35S Enhancer | 438 | Enhancer region from the Cauliflower Mosaic Virus genome (Franck et al., 1980; Odell et al., 1985). |
| 4532 to 4566 | Polylinker Region | 35 | Region required for cloning genetic elements |
| 4567 to 5466 | ubiZM1 Promoter | 900 | Promoter region from *Zea mays* ubiquitin gene (Christensen et al., 1992). |
| 5467 to 5549 | ubiZM1 5' UTR | 83 | 5' untranslated region from *Zea mays* ubiquitin gene (Christensen et al., 1992). |
| 5550 to 6558 | ubiZM1 Intron | 1009 | Intron region from *Zea mays* ubiquitin gene (Christensen et al., 1992). |
| 6559 to 6586 | Polylinker Region | 28 | Region required for cloning genetic elements |
| 6587 to 7030 | glyat4621 Gene | 444 | Synthetic glyphosate N-acetyltransferase gene (Castle et al., 2004. Siehl et al., 2007). |
| 7031 to 7046 | Polylinker Region | 16 | Region required for cloning genetic elements |
| 7047 to 7362 | pinII Terminator | 316 | Terminator region from *Solanum tuberosum* proteinase inhibitor II gene (Keil et al., 1986; An et al., 1989). |
| 7363 to 7415 | Ti Plasmid Region | 53 | Non-functional sequence from Ti plasmid of *A. tumefaciens* |
| 7416 to 7440 | Left Border | 25 | T-DNA Left Border region, from Ti plasmid of *Agrobacterium tumefaciens* |

TABLE 4

Description of Genetic Elements of Plasmid PHP24279 used for the creation of DP-098140-6 maize

| Region | Location on plasmid (base pair position) | Known Genetic Element | Size (base pairs) | Description |
|---|---|---|---|---|
| Plasmid Construct | 1 to 40 | | 40 | DNA for plasmid construction and plasmid replication |
| Ti Plasmid Backbone | 41 to 14855 | includes elements below | 14815 | Virulence (vir) gene region and intergenic regions from Ti plasmid of *Agrobacterium tumefaciens*. (GenBank Accession No. AB027255) |
| | 1065 to 1759 | virC1 | 695 | Virulence gene important for T-DNA insertion into genome. |
| | 1762 to 2370 | virC2 | 609 | Virulence gene important for T-DNA insertion into genome. |
| | 2481 to 3284 | virG | 804 | Virulence gene important for T-DNA insertion into genome. |
| | 3416 to 12851 | virB | 9436 | Virulence gene important for T-DNA insertion into genome. |
| Plasmid Construct | 14856 to 18087 | includes elements below | 3232 | DNA from various sources for plasmid construction and plasmid replication |

TABLE 4-continued

Description of Genetic Elements of Plasmid PHP24279 used for the creation of DP-098140-6 maize

| Region | Location on plasmid (base pair position) | Known Genetic Element | Size (base pairs) | Description |
|---|---|---|---|---|
|  | 15152 to 15521 | colE1 ori | 370 | bacterial origin of replication region (*E. coli*) (Tomizawa et al., 1977) |
|  | 16614 to 16626 | cos | 13 | cos site; cohesive ends from lambda bacteriophage DNA (GenBank Accession No. AB027255) |
| T-DNA | 18088 to 25527 |  | 7440 | see Table 3 for information on the elements in this region |
| Plasmid Construct | 25528 to 50371 | includes elements below | 24844 | DNA from various sources for plasmid construction and plasmid replication |
|  | 26703 to 27491 | spc | 789 | Spectinomycin resistance gene from bacteria. (GenBank Accession No. CP000038) |
|  | 28614 to 28983 | colE1 ori | 370 | bacterial origin of replication region (*E. coli*) (Tomizawa et al., 1977) |
|  | 30080 to 30092 | cos | 13 | cos site; cohesive ends from lambda bacteriophage DNA (GenBank Accession No. AB027255) |
|  | 31794 to 32444 | tetR | 651 | Tetracycline resistance regulation gene from bacteria (GenBank Accession No. AB027255) |
|  | 32550 to 33749 | tetA | 1200 | Tetracycline resistance gene from bacteria (GenBank Accession No. AB027255) |
|  | 34380 to 36569 | rep | 2190 | rep operon (includes trfA below) (GenBank Accession No. AB027255) |
|  | 35022 to 36170 | trfA | 1149 | Trans-acting replication gene from bacteria (GenBank Accession No. AB027255) |
|  | 39984 to 40095 | oriT | 112 | oriT origin of transfer region from bacteria (GenBank Accession No. AB027255) |
|  | 41935 to 48205 | ctl | 6271 | Central control operon region from bacteria (GenBank Accession No. AB027255) |
|  | 49213 to 49923 | oriV | 711 | oriV origin of replication region from bacteria (GenBank Accession No. AB027255) |

The nucleotide sequence of the inserted T-DNA in the DP-098140-6 event has been determined. PCR amplification of the unique junctions spanning the introduced genetic elements can distinguish DP-098140-6 plants from their non-genetically modified counterparts and can be used to screen for the presence of the inserted T-DNA, even at very low concentrations. Provided below is a construct-specific polymerase chain reaction (PCR) assay on genomic DNA from leaf and mature seed of DP-098140-6 maize.

Specifically, genomic DNA from leaf tissue and mature seed of the test substance (seed from event DP-098140-6) and the control substance (seed from a non-genetically modified maize with a genetic background) representative of the event background was isolated and subjected to qualitative PCR amplification using a construct-specific primer pair. The PCR products were separated on 10.5% or 2% agarose gels to confirm the presence of the inserted construct in the genomic DNA generated from the test substance, and absence in the genomic DNA generated from the control substance. A reference standard (100 base pair DNA Ladder; Invitrogen Corporation Catalog #10380-012) was used to determine the PCR product size.

Test and control leaf samples (V5-V7 leaf stage) were harvested from plants. Genomic DNA extraction from the test and control leaf tissues was performed using a standard urea extraction protocol. Genomic DNA from the test and control seed samples was isolated using Wizard® Magnetic 96 DNA Plant System (Promega Corporation Catalog #FF3760). Genomic DNA was quantified on a spectrofluorometer using PicoGreen® reagent (Molecular Probes, Inc., Eugene, Oreg.), and/or visualized on an agarose gel to confirm quantitation values and to determine the DNA quality.

Genomic DNA isolated from leaf and mature seed of event DP-098140-6 and control samples was subjected to PCR amplification (PCR Master Mix Catalog #7505 from Promega Corporation) utilizing the construct-specific primer pair (06-O-1734/06-O-1738) which spans the maize ubiquitin intron and the glyat4621 coding region, and allows for the unique identification of maize event DP-098140-6. A second primer set (02-O-197/02-O-198) was used to amplify the endogenous maize invertase gene (Genbank accession number AF171874) as a positive control for PCR amplification. The PCR target site and size of the expected PCR product for each primer set are shown in Table 5. PCR reagents and reaction conditions are shown in Table 6A and 6B. The primer sequences used in this study are listed in Table 7.

TABLE 5

PCR Genomic DNA Target Site and Expected Size of PCR Products

| Primer Set | Construct DNA Target Site | Expected Size of PCR Product (bp) |
|---|---|---|
| 06-O-1734/06-O-1738 | Ubiquitin intron/glyat4621 coding regions of PHP24279 | 203 |
| 02-O-197/02-O-198 | Maize invertase gene | 225 |

PCR: POLYMERASE CHAIN REACTION
BP: BASE PAIRS

TABLE 6A

PCR Reagents and Reaction Conditions for Leaf and Seed

| | PCR Reagents for leaf | | PCR Reaction Conditions for leaf | | |
|---|---|---|---|---|---|
| Reagent | Volume (µL) | Cycle Element | Temp (° C.) | Time (min) | # Cycles |
| Template DNA (10 ng/µl) | 4 | Initial Denaturation | 94 | 5 | 1 |
| Primer 1 (10 µM) | 2 | Denaturation | 95 | 1 | 35 |
| Primer 2 (10 µM) | 2 | Annealing | 55 | 2 | 35 |
| PCR Master Mix* | 25 | Elongation | 72 | 3 | 35 |
| ddH$_2$O | 17 | Final Elongation | 72 | 7 | 1 |

PCR: POLYMERASE CHAIN REACTION
DDH$_2$O: DOUBLE-DISTILLED WATER
● Promega #M7505

TABLE 6B

| | PCR Reagents for seed | | PCR Reaction Conditions for seed | | |
|---|---|---|---|---|---|
| Reagent | Volume (µL) | Cycle Element | Temp (° C.) | Time (min) | # Cycles |
| Template DNA (2.4 ng/µl) | 5 | Initial Denaturation | 94 | 5 | 1 |
| Primer 1 (10 µM) | 2 | Denaturation | 95 | 1 | 35 |
| Primer 2 (10 µM) | 2 | Annealing | 55 | 2 | 35 |
| PCR Master Mix* | 25 | Elongation | 72 | 3 | 35 |
| ddH$_2$O | 16 | Final Elongation | 72 | 7 | 1 |

PCR: POLYMERASE CHAIN REACTION
DDH$_2$O: DOUBLE-DISTILLED WATER
*Promega #M7505

TABLE 7

List of Primer Sequences Used in PCR Reactions

| Primer Name | Sequence 5'-3' | Target Sequence | SEQ ID NO |
|---|---|---|---|
| 06-O-1734 | TATGCCTAAGGTCATAGGTATCCTCTGCGTTG | DP-098140-6 specific | 20 |
| 06-O-1738 | TGATGGCATATGCAGCAGCTATATGTGGAT | DP-098140-6 specific | 21 |
| 02-O-197 | CCGCTGTATCACAAGGGCTGGTACC | Maize invertase gene | 22 |
| 02-O-198 | GGAGCCCGTGTAGAGCATGACGATC | Maize invertase gene | 23 |

Construct-specific PCR products of approximately 200 bp in size amplified by the construct-specific primer set 06-O-1734/06-O-1738 were observed in all the DP-098140-6 DNA samples from leaf and mature seed, but absent in all control samples and the no-template control. This experiment was repeated several times, and similar results were obtained (data not shown). These results correspond closely with the expected PCR product size (203 bp) for genomic DNA samples containing event DP-098140-6. A PCR product approximately 220 bp in size was observed for both event DP-098140-6 and control samples following PCR reaction with the primer set 02-O-197/02-O-198 for detection of the endogenous maize invertase gene in leaf and seed samples (data not shown). This result corresponds closely with the expected PCR product size (225 bp) for genomic DNA samples containing the maize endogenous invertase gene in all samples. The endogenous target band was not observed in the no-template control.

Since leaf genomic DNA and mature seed genomic DNA were isolated using different protocols, the amount of template to use for a PCR reaction was tested. In this study, 40 ng of leaf genomic DNA and 12 ng of seed genomic DNA were used in a PCR reaction for all the analyses.

In order to assess the sensitivity of the PCR amplification, different dilutions of a single DNA sample of DP-098140-6 were made into non-genetically modified control DNA, resulting in DP-098140-6 DNA amounts ranging from 40 ng down to 800 fg in leaf (total DNA amount in all samples was 40 ng), and 12 ng down to 240 fg in mature seed (total DNA amount in all samples was 12 ng). Each dilution was subjected to PCR amplification as previously described. Based on this analysis, the limit of detection (LOD) was determined to be approximately 40 pg of DP-098140-6 DNA in 40 ng of total DNA, or 0.1% of event DP-098140-6 DNA in leaf (data not shown); and approximately 120 pg of event DP-098140-6 DNA in 12 ng of total DNA, or 1% in seed (data not shown). This provides sufficient sensitivity for many screening applications.

Qualitative PCR analysis utilizing a construct-specific primer set for event DP-098140-6 confirmed that the test plants contained event DP-098140-6, as evidenced by the presence of the construct-specific target band in all test plant samples analyzed including leaf and mature seed, and absence in the non-genetically modified control plants. This result was reproducible. Test and control plants both contained the endogenous maize invertase gene. The predicted sensitivity of the analysis under the conditions prescribed is 0.1% event DP-098140-6 DNA for leaf, and 1% for mature seed.

Example 2

Characterization of Maize Event DP-098140-6 by Southern Blot

The characterization of the DNA inserted into DP-098140-6 (hereinafter "98140") maize was performed by Southern blot analysis. Table 8 summarizes the results from various Southern blot analyses. The method used is described as follows. Genomic DNA was extracted from lyophilized leaf tissue sampled on 98140 maize and non-genetically modified control plants. Genomic DNA was digested with restriction endonuclease enzymes and size separated on an agarose gel. A molecular weight marker was run alongside samples for size estimation purposes. DNA fragments separated on agarose gel were depurinated, denatured and neutralized in situ, and transferred to a nylon membrane. Following transfer to the membrane, the DNA was bound to the membrane by UV crosslinking. Fragments homologous to the glyat4621 and zm-hra genes were generated by PCR from plasmid PHP24279 separated on an agarose gel by size, exsized, and purified using a gel extraction kit. All DNA probes were generated from the fragment by random prime labeling using [$^{32}$P]dCTP. Labeled probe was hybridized to the target DNA on the nylon membranes for detection of the specific fragments. Washes after hybridization were carried out at high stringency. Blots were exposed to X-ray film for one or more time points to detect hybridizing fragments and visualize molecular weight markers. The molecular analysis of the insert in DP-098140-6 maize is presented in detail below. The results of the Southern analysis of DP-098140-6 maize indicate that there is a single, intact copy of the T-DNA inserted into DP-098140-6 maize. Moreover, since this genetically modified maize has been obtained through *Agrobacterium*-mediated transformation method, the absence of incorporation of backbone DNA from outside the T-DNA borders has also been determined by real-time qualitative PCR. The details of the method used are provided below. These results indicate that only DNA contained within the T-DNA borders of plasmid PHP24279 was integrated into DP-098140-6 maize.

Figure 6:
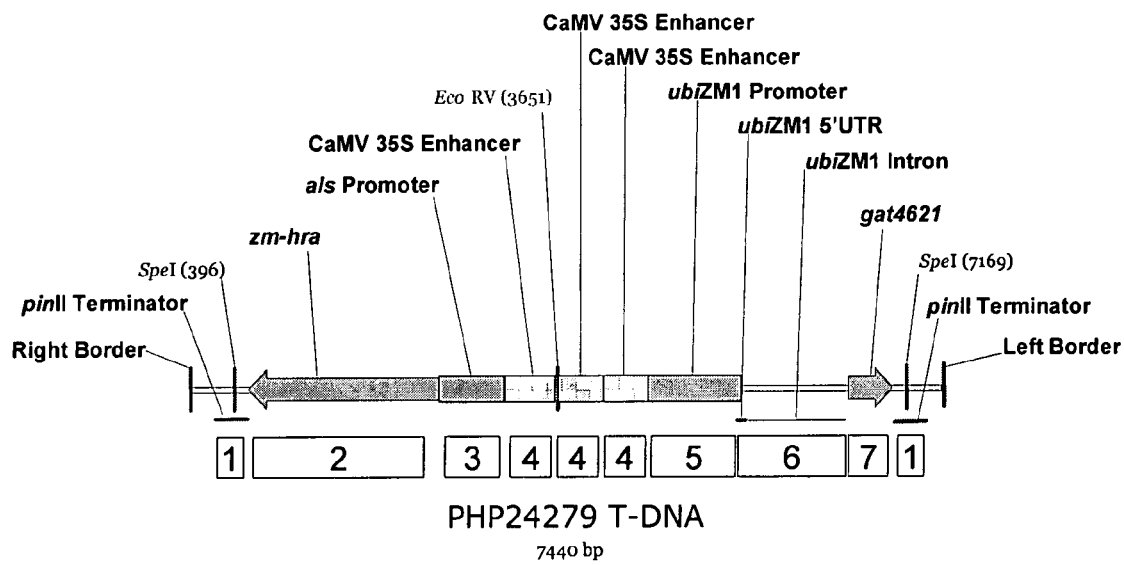
FIG. 6 provides schematic map of the T-DNA from plasmid PHP24279 indicating the location of genetic elements within the glyat4621 and zm-hra expression cassettes and base pair positions for restriction enzyme sites for EcoR V and Spe I. The total T-DNA size is 7386 base pairs. Probes are indicated schematically as numbered boxes below the map and are identified below. Additional details on these probes are provided in Table 24.

The restriction enzyme Spe I was selected to evaluate the integrity of the inserted T-DNA, since these sites flank both gene cassettes releasing a fragment of 6775 bp (FIG. 6). The glyat4621 probe hybridized to the expected 6775 bp fragment in Spe I digested DNA (Table 8) as did the zm-hra probe (Table 8), indicating an intact T-DNA had inserted into the genome. The zm-hra probe also hybridized to two other bands in 98140 maize which are endogenous based because of their presence in unmodified maize. This result was expected as the zm-hra gene in this construct was modified from the endogenous maize gene. Based on these results, the insertion in 98140 maize contains an intact copy of the T-DNA of PHP24279.

In order to evaluate the number of glyat4621 and zm-hra genes inserted, the restriction enzyme EcoR V was selected. There is a single EcoR V site between the glyat4621 and zm-hra cassettes in PHP24279 T-DNA (FIG. 6). The number of hybridizing bands with the glyat4621 and zm-hra probes would provide an indication of the number of inserted copies of each gene. A single fragment of approximately 6000 bp was observed with the glyat4621 probe in 98140 maize, indicating a single copy of the glyat4621 gene in 98140 maize (Table 8). In addition, the zm-hra probe hybridized to a single fragment of greater than 10 kb in DP-098140-6 maize, indicating a single copy of the zm-hra gene (Table 8). On this blot, the zm-hra probe hybridized to additional bands which were present in the unmodified maize sample and were due to endogenous maize genes. Together, these results indicate that there is a single, intact copy of the T-DNA inserted into DP-098140-6 maize.

Real-time qualitative PCR was also conducted on genomic DNA isolated from leaf tissue punches of the primary transformant (T0) generation in order to screen for backbone DNA presence. Genomic DNA was isolated from maize leaf punches using Extract-N-Amp™ Kit (Sigma Aldrich). Taq-Man® probe and primer pairs were designed to detect the following backbone targets: the tetracycline resistance (tetA) gene (51 bp amplicon), the spectinomycin resistance (spc) gene (57 bp amplicon), the virG gene (66 bp amplicon), and two regions just outside of the left border (LB, 58 bp amplicon) and right border (RB, 62 bp amplicon) of the T-DNA. In addition, to confirm the presence of amplifiable DNA in each reaction, a TaqMan® probe and primer pair for a maize endogenous gene was used (62 bp amplicon). Extract-N-Amp™ PCR Reaction Mix with passive reference dye to normalize fluorescent fluctuations (Sigma Aldrich) was used for the assay. After initial incubations at 50° C. for 2 minutes and then at 95° C. for 3 minutes, 40 cycles were conducted as follows: 95° C. for 15 seconds, 60° C. for 1 minute. Positive or negative determination was based on comparison of the Ct (threshold cycle) of the backbone target to that of the endogenous target.

DP-098140-6 maize was negative for the presence of backbone DNA based on this screen using different probes to detect the tetracycline resistance (tet), spectinomycin resistance (spc) and virG genes plus two regions immediately outside of the left (LB) and right (RB) borders (regions not typically incorporated during *Agrobacterium*-mediated transformations) (Table 9). Each reaction contained amplifiable DNA based on the endogenous gene control. The results indicate that only DNA contained within the T-DNA borders of plasmid PHP24279 was integrated into DP-098140-6 maize

TABLE 8

Summary of expected and observed hybridization fragments on Southern blots for DP-098140-6 maize

| Maize | Probe | Enzyme Digest | Expected Fragment Size (bp) from PHP24279 T-DNA | Observed Fragment Size (bp) |
|---|---|---|---|---|
| DP-098140-6 | glyat4621 | Spe I | 6775 | 6775[1] |
| unmodified maize (control) | glyat4621 | Spe I | no hybridization | no hybridization |
| DP-098140-6 | zm-hra | Spe I | 6775 | 6775[1] ~5500* ~5000* |
| unmodified maize (control) | zm-hra | Spe I | no hybridization | ~5500* ~5000* |
| DP-098140-6 | glyat4621 | EcoR V | >3790 (border) | ~6000 |
| unmodified maize (control) | glyat4621 | EcoR V | no hybridization | no hybridization |
| DP-098140-6 | zm-hra | EcoR V | >3652 (border) | >10000 ~9000* ~7000* |

TABLE 8-continued

Summary of expected and observed hybridization fragments on Southern blots for DP-098140-6 maize

| Maize | Probe | Enzyme Digest | Expected Fragment Size (bp) from PHP24279 T-DNA | Observed Fragment Size (bp) |
|---|---|---|---|---|
| unmodified maize (control) | zm-hra | EcoR V | no hybridization | ~9000*<br>~7000* |

Footnotes:
Fragments with an asterisk (*) were due to hybridization of the probe to endogenous maize sequences and were identified based on their presence in unmodified maize.
[1]Equivalent migration with plasmid positive control. Same size as expected.

TABLE 9

Results of real-time qualitative PCR analysis to detect backbone DNA in DP-098140-6 maize

| Backbone DNA tested | Assay result |
|---|---|
| tet | Negative |
| spc | Negative |
| virG | Negative |
| LB | Negative |
| RB | Negative |

Example 3

Expression of the Insert

Expression of the GLYAT4621 and Zm-HRA proteins has been evaluated on the leaf tissue collected at the V5 stage of growth from plants cultivated in greenhouses. For each sample, four fresh leaf punches were collected and ground in sample extraction buffer using a GenoGrinder (Spex Certiprep). Total Extractable Protein (TEP) was determined using the Bio-Rad Protein assay, which is based on the Bradford dye-binding procedure. Sample extracts were diluted in sample extraction buffer for ELISA analysis.

The GLYAT4621 and ZM-HRA ELISA's utilize a "sandwich" format for the quantification of the specific target protein in plant tissue extracts. In these assays, standards (triplicate wells) and samples (duplicate wells) are incubated in stabilized plates that have been pre-coated with an antibody specific for the protein of interest. After one hour of incubation, unbound substances are washed from the plate and the bound protein is incubated with a different protein-specific antibody that has been conjugated to the enzyme horseradish peroxidase (HRP). The detection of the bound complex is accomplished through the addition of the HRP substrate solution. The reaction is stopped with Sulfuric acid and the optical density of each well is determined using a Molecular Devices plate reader with a wavelength setting of 450 nm-650 nm. Softmax® Pro software is used to perform the calculations that generate the quadratic fit for the standard curve and convert the sample OD values to target protein concentration values. The mean concentration from the duplicate wells is expressed as pg target protein/μg of total extractable protein (TEP). The sample lower limit of quantification (LLOQ) was 10 pg GLYAT4621 protein/μg TEP and the upper detection limit was 2000 pg GLYAT4621 protein/μg TEP. The sample lower limit of quantification was 20 pg ZM-HRA protein/μg TEP and the upper detection limit was 5000 pg ZM-HRA protein/μg TEP.

The results are presented in Table 10 and show that the GLYAT4621 and ZM-HRA proteins are expressed in leaf tissues of DP-098140-6 maize. As expected, GLYAT4621 and ZM-HRA proteins were not detected in any samples from the non genetically modified control plants.

TABLE 10

Summary of expression level of GLYAT4621 and ZM-HRA proteins measured in leaf tissues from DP-098140-6 maize plants collected at the V5 developmental growth stage from plants.

| Protein | Mean (pg/μg TEP[a]) | Standard Deviation | Range[b] (pg/μg TEP) | Number of plants analyzed |
|---|---|---|---|---|
| GLYAT4621 | 571.7 | 140 | 370-820 | 20 |
| ZM-HRA | 73.4 | 10.7 | 54.9-91.6 | 19 |

[a]TEP: Total Extractable Proteins
[b]Range: lowest observed individual result-highest observed individual result Another way to verify the expression of the insert in DP-098140-6 maize plants was to estimate their tolerance to glyphosate and sulfonylureas. A herbicide tolerance experiment was conducted at ten locations. The purpose of the experiment was to determine tolerance of DP-098140-6 maize to glyphosate and sulfonylureas. DP-098140-6 maize was sprayed with glyphosate at 10.26 kg ae/ha[1], chlorimuron at 5.8 g ai/ha[2], tribenuron at 17.3 g ai/ha and rimsulfuron at 17.5 g ai/ha. All herbicide applications occurred at the V4 developmental growth stage. Three plants at each of the ten locations were scored for herbicide injury, 10 days following the V4 herbicide application. Herbicide injury scores were collected on a 0-100 scale with 0 showing no injury symptoms (a rating of 5 is well tolerant—only minor leaf flashing on the plant) and 100 showing complete death of the plant (Table 12).

[1] kg acid equivalent per hectare
[2] g active ingredient per hectare

Results are averaged over the ten locations and three plants, and standard deviations are shown in Table 11. The results showed that DP-098140-6 maize was well tolerant to glyphosate and sulfonylureas. In some instances, the standard deviation is higher than the mean injury score due to the nature of the attached crop response rating system. Since plants are measured on a 0 to 100 scale of injury, a score of 5 on one plant causes the standard deviation to rise higher than the mean, although, as mentioned earlier and shown Table 12, a rating of 5 is well tolerant to the herbicide with little to no injury present.

TABLE 11

Results of herbicide injury scoring of DP-098140-6 maize sprayed with glyphosate and sulfonylureas (chlorimuron, tribenuron and rimsulfuron)

| Maize | Mean glyphosate/sulfonylureas injury (rated 10 days following the V4 stage application) | Standard deviation glyphosate/sulfonylureas injury |
|---|---|---|
| 98140 | 0.17 | 0.91 |

TABLE 12

The 0 to 100 crop response rating system for herbicide injury

| Rating | Main categories | Detailed description |
|---|---|---|
| 0 | No Effect | No crop reduction or injury |
| 10 | Slight Effect | Slight crop discoloration or stunting |
| 20 | | Some crop discoloration, stunting, or stunt loss |
| 30 | | Crop injury more pronounced, but not lasting |
| 40 | Moderate Effect | Moderate injury, crop usually recovers |
| 50 | | Crop injury more lasting, recovery doubtful |
| 60 | | Lasting crop injury, no recovery |
| 70 | Severe Effect | Heavy crop injury and stand loss |
| 80 | | Crop nearly destroyed - A few surviving plants |
| 90 | | Only occasional live crop plants left |
| 100 | Complete Effect | Complete crop destruction |

Example 4

Mendelian Segregation of the DP-098140-6 Trait

The Mendelian segregation of the glyat4621 gene was analyzed during the plant breeding process by spraying glyphosate. The original transformed 98140 maize was crossed to an elite inbred to give a single cross hybrid. The single cross hybrid was backcrossed to the elite inbred one more time to give BC1 seed. The BC1 generation was crossed again to the elite line to give BC2.

Spraying at each generation eliminated glyphosate-susceptible plants and resulted in hemizygous seed. The seed from the backcross generation breeding lines were planted and the plants were sprayed with glyphosate. For each of these generations, the expected ratio of tolerant plants to susceptible plants was 1:1. The observed ratio is presented in Table 13. The results show that for the different generations analyzed for DP-098140-6 maize, there were no significant differences between the observed segregation ratio and the expected segregation ratios at the significant level of 5%. The GLYAT4621 and ZM-HRA expression cassettes are contained within the same insertion and thus, the glyphosate segregation data is representative of the segregation patterns for glyphosate and ALS-inhibiting herbicides such as sulfonylureas. Thus, data on the Mendelian segregation of the transgene provides evidence of the stable inheritance of newly introduced genetic material.

TABLE 13

Mendelian segregation of DP-098140-6 maize based on glyphosate tolerance

| Generation | Observed Ratio[a] | Expected Ratio[b] | Chi square | Significant Difference? |
|---|---|---|---|---|
| BC1 | 82:80 | 81:81 | 0.88 | No |
| BC2 | 59:56 | 57.5:57.5 | 0.78 | No |

[a]Data expressed as number of observed plants tolerant to glyphosate:number of observed plants susceptible to glyphosate.
[b]Data expressed as number of expected plants tolerant to glyphosate:number of expected plants susceptible to glyphosate.

Example 5

Further Insert and Flanking Border Sequence Characterization of Maize Event DP-098140-6

To characterize the integrity of the inserted DNA and the genomic insertion site, the flanking genomic DNA border regions of DP-098140-6 maize were determined. The flanking genomic sequence of maize DP-098140-6 is set forth in SEQ ID NO:1 and 46. PCR amplification from the DP-098140-6 maize insert and border sequences confirmed that the border regions were of maize origin and that the junction regions could be used for identification of DP-098140-6 maize. Overall, characterization of the insert and genomic border sequence of DP-098140-6 maize along with Southern blot data indicated that a single insertion of the DNA fragment was present in the maize genome. Various molecular techniques are then used to specifically characterize the integration site in the DP-098140-6 maize line.

In the initial characterization of the DP-098140-6 maize line, the flanking genomic border regions were cloned and sequenced using the GenomeWalker and inverse PCR methods. Using information from the flanking border sequence, PCR was performed on DP-098140-6 maize genomic DNA and unmodified control genomic DNA.

For the left border sequence, PCR was performed with a primer in the left genomic border (primer 99885; SEQ ID NO:15) and a primer in the transgene insert (primer 100240; SEQ ID NO: 16), resulting in the expected products in DP-098140-6 maize plants (1.2 kb).

For the right genomic border sequence, PCR was performed with a primer in the right genomic border (primer 100235; SEQ ID NO:13) and a primer in the transgene insert (primer 99878; SEQ ID NO: 14), resulting in the expected products in DP-098140-6 maize plants (750 bp).

Additional primer sequences were developed and the following protocol was used.

Oligonucleotide PCR Reagents:

```
Forward Primer:
                                      (SEQ ID NO: 17)
5' GTCCGCAATGTGTTATTAAGTTGTCT 3'

Reverse Primer:
                                      (SEQ ID NO: 18)
5' TTTTTTCTAGGAAAGCTGGTTACATG 3'

Taqman MGB probe:
                                      (SEQ ID NO: 19)
5' Fam-AGCGTCAATTTGC-MGB 3'
```

Each primer was used at a concentration of 600 nM in the PCR. The MGB probe was used at a concentration of 80 nM in the PCR. The PCR mixture used was "Extract-N-Amp PCR Ready Mix" (Cat. No. E3004) from Sigma-Aldrich. Rox reference dye was also included in the PCR mixture by adding 0.01 volumes of Sigma-Aldrich "Reference Dye for Quantitative PCR" (Cat. No. R4526). PCR was performed for 40 cycles with one cycle consisting of the following two steps: Step 1: 15 seconds at 95° C.; Step 2: 60 seconds at 60° C. The amplicon product has a size of 85 bp.

Those skilled in the art would also include a control PCR using an endogenous gene to verify that the isolated genomic DNA was suitable for PCR amplification. Maize endogenous genes that have been used successfully with maize samples are the following: Invertase gene (Hernandez et al. (2004) *J. Agric Food Chem.* 52:4632-4637; Hernandez et al. (2004) *J Cereal Science* 39:99-107; Alcohol Dehydrogenase gene (Hernandez et al. (2004) *J. Agric Food Chem.* 52:4632-4637; Ingham et al. (2001) *BioTechniques* 31:132-140; Zein gene (Hernandez et al. (2004) *J. Agric. Food Chem.* 52:4632-4637; Vaitilingom et al. (1999) *J. Agric. Food Chem.* 47:5261-5266 and High Mobility Group gene (Hernandez et al. (2004) *J. Agric Food Chem.* 52:4632-4637; Pardigol et al. (2003) *Eur Food Res Technol* 216:412-420.

TABLE 14

Description and Sizes of PCR Products

| Primer | Primer | Description of amplified region | Size (bp) of PCR product |
|---|---|---|---|
| 100235 | 99878 | Right flanking genomic sequence/transgene border | 751 bp |
| 99885 | 100240 | left flanking genomic sequence/transgene border | 1257 bp |

TABLE 14-continued

Description and Sizes of PCR Products

| Primer | Primer | Description of amplified region | Size (bp) of PCR product |
|---|---|---|---|
| 102588 | 102589 | left flanking genomic sequence/transgene border | 85 bp |

TABLE 25

Description of Additional Oligonucleotides and Regions of Amplification.

| NAME | DESCRIPTION | SEQUENCE | SEQ ID NO |
|---|---|---|---|
| 06-O-1536 | ZM-HRA oligo F | AAGGGTGCTGACATCCTCGTCGAGT | 25 |
| 06-O-1537 | ZM-HRA middle oligo R | GTCCCATGCATACCTAGCATGCGCA | 26 |
| 06-O-1538 | ZM-HRA middle oligo F | GGATAAGGCCGATCTGTTGCTTGCA | 27 |
| 06-O-1539 | ZM-HRA oligo R | TCAGTACACAGTCCTGCCATCACCAT | 27 |
| 06-O-1541 | GLYAT (4621)F | ATGGCTATTGAGGTTAAGCC | 29 |
| 06-O-1542 | GLYAT (4621)R | CCTCTTATACATCAGGATGTGAGG | 30 |
| 06-O-1779 | forward; 5' border | ATGAAAAAGTCCAAGTCGAGCAAGGGTACGTAC | 34 |
| 06-O-1782 | reverse; 3' border | GCTAGCCCTAACTGGCACCATATATCATTTTG | 35 |
| 06-O-1783 | reverse; 3' border | AACTGCACCAGTCACTTGGCAAACGAC | 36 |
| 07-O-1877 | forward; 5' border | CGTTTTTTTGTGTGTGTATGTCTCTTTGCTTGGTC | 37 |
| 07-O-1878 | forward; 5' border | TGTATGTCTCTTTGCTTGGTCTTTCTCTATCGATC | 38 |
| 07-O-1879 | reverse; 3' border | ATGACGTGATACAACTTTACTTCAGTATAAGACTG | 39 |
| 07-O-1880 | reverse; 3' border | CAACTATCTCAGTCTTATTCTATGTTCATGACGTG | 40 |
| 07-O-1946 | Insert | TCGGAGTACAGACGGTACTGACACAAG | 41 |
| 07-O-1947 | forward, insert | CCTCTCTAGAGATAATGAGCATTGCATGTC | 42 |
| 07-O-1948 | reverse, insert | GCGACCCGTTTGGATTCCCTTGTCTG | 43 |
| 07-O-1949 | reverse, insert | TGCAAGCTCCTAATCCCGGGCTGCAG | 44 |
| 07-O-1950 | reverse, insert | CTGGTTCGCTGGTTGGTGTCCGTTAG | 45 |
| DP098-3'-f12 | Forward | TGCGAATTCAGTACATTAAAAACGT | 51 |
| DP098-3'-r12 | Reverse | TGTTTTTTTTCTAGGAAAGCTGGTT | 52 |

TABLE 25-continued

Description of Additional Oligonucleotides and Regions of Amplification.

| NAME | DESCRIPTION | SEQUENCE | SEQ ID NO |
|---|---|---|---|
| DP098-3'-p6 | | FAM-CCGCAATGTGTTATTAAGTTGTCTAAGCGTCA-TAMRA | 53 |
| DP098-f6 | Forward | GTGTGTATGTCTCTTTGCTTGGTCTT | 54 |
| DP098-r2 | Reverse | GATTGTCGTTTCCCGCCTTC | 55 |
| DP098-65 | Probe | FAM-CTCTATCGATCCCCCTCTTTGATAGTTTAAACT-TAMRA | 56 |

Example 6

Herbicide Tolerance and ELISA Analysis of Two Generations of Maize Event DP-098140-6

DP-098140-6 maize (Zea mays) has been modified by the insertion of the glyat4621 and zm-hra genes. The glyat4621 gene, isolated from Bacillus licheniformis, was functionally improved by a gene shuffling process to optimize the kinetics of glyphosate acetyltransferase (GLYAT) activity. The GLYAT4621 protein, encoded by the glyat4621 gene, confers tolerance to the herbicidal active ingredient glyphosate. The insertion of the zm-hra gene produces a modified form of the acetolactate synthase enzyme (ALS). ALS is essential for branched chain amino acid biosynthesis and is inhibited by certain herbicides. The modification in the zm-hra gene overcomes this inhibition and thus provides tolerance to a wide range of ALS-inhibiting herbicides.

The objective of this study was to evaluate the herbicide tolerance and protein expression in maize containing the event DP-098140-6. Two generations of the DP-098140-6 maize and two generations of near isoline control maize were evaluated to determine whether DP-098140-6 maize displayed consistent protein expression and tolerance to glyphosate and ALS-inhibiting herbicides across generations.

Plants were grown in a greenhouse using a randomized complete block design containing four blocks. Each block consisted of twenty-four flats. Flats representing entries 1-12 (segregating 1:1) contained approximately fifteen plants per entry, while flats representing entries 13-24 (non-segregating) contained approximately ten plants per entry. Trait confirmation for GLYAT4621 was conducted for test and control entries at the V2 growth stage using lateral flow strip tests specific for the GLYAT protein. Plants with positive trait confirmation results (expressing GLYAT4621) were used for test entries and plants with negative trait confirmation results (not expressing GLYAT4621) were used as the control entries. Any remaining negative segregants not used for controls were then removed and remaining positive plants were thinned to 5 plants per entry within each block (treatment). At the V4 growth stage, a herbicide treatment containing glyphosate (1.46 L/ha or 20 oz/acre)+nonionic surfactant (0.25% vol./vol.)+ammonium sulfate (3.4 kg/ha) was applied to entries 1, 9, 13, and 21; herbicides containing thifensulfuron (3.5 g/ha or 0.5 oz/acre) and tribenuron (3.5 g/ha or 0.5 oz/acre) each containing nonionic surfactant (0.25% vol./vol.)+ammonium sulfate (3.4 kg/ha) were applied to entries 2, 10, 14 and 22; and a tank mixture of herbicides containing glyphosate, thifensulfuron and tribenuron was applied to entries 3, 11, 15, and 23 (Table 15).

Herbicide injury was evaluated visually at 14 and 21 days after herbicide application by estimating herbicide injury percentage, where "0" represented no visible injury and "100" represented complete plant death. The injury rating took into account all symptoms of herbicide injury when compared to the untreated entry for the same maize line. Injury symptoms included discoloration, leaf speckling, and wilting. The untreated entries for each maize line were rated as 0% injury and the herbicide treated entries of the same maize line were rated by comparing them to this untreated entry. Photographs were taken at 21 days following herbicide application to record herbicide injury. In order to further characterize tolerance to ALS-inhibiting herbicides, a characteristic of the zm-hra gene in DP-098140-6 maize, plant heights were measured for all entries at 14 and 21 days post herbicide treatment. Plant height was measured in cm from the soil surface to the tip of the highest leaf when extended by hand.

Quantitative Enzyme-Linked Immunosorbent Assay (ELISA) analyses were conducted to characterize the expression of GLYAT4621 and ZM-HRA proteins in DP-098140-6 maize seed. Methods for conducting the quantitative ELISA were as follows:

All leaf and seed samples were lyophilized and finely ground for approximately 60 seconds using a SPEX Certiprep GenoGrinder. Between lyophilization and grinding, samples were stored frozen in temperature-monitored freezers at <−10° C.

Homogenized tissues were weighed into 1.2 ml tubes at the following target weights: 10 mg for leaf and 20 mg for seed. Each sample was extracted with 0.6 ml of assay buffer and two 5/32" steel balls using a single 30 second cycle with a setting of 1500 strokes per minute. Insoluble material was separated by centrifugation (4,000 rpm for 10 minutes). Diluted extracts were analyzed using specific GLYAT4621 and ZM-HRA ELISA methods.

The GLYAT4621 ELISA method utilized a sequential "sandwich" ELISA for the determination of the presence of GLYAT4621 in maize plant tissue extracts. Standards (analyzed in triplicate wells) and diluted sample extracts (analyzed in duplicate wells) were incubated for one hour in stabilized 96-well plates that were pre-coated with a GLYAT4621-specific antibody. Unbound substances were washed from the plate, and a different GLYAT4621-specific antibody that had been conjugated to the enzyme horseradish peroxidase (HRP) was added to the wells. Bound GLYAT4621 protein was sandwiched between the antibody coated on the plate and the antibody-HRP conjugate. At the end of the 1 hour incubation, unbound substances were washed from the plate. Detection of the bound GLYAT4621 protein-antibody complex was accomplished by the addition of a substrate, which generated a colored product in the presence of HRP. The reaction was stopped with stop solution (1N hydrochloric acid) after 30 minutes and the optical density of each well was determined using a Molecular Devices plate reader (Molecular Devices Corporation, 1311 Orleans Drive, Sunnyvale, Calif. 94089-1136, USA) with a wavelength setting of 450 nm minus 650 nm. SoftMax Pro software (Molecular Devices Corporation, 1311 Orleans Drive, Sunnyvale, Calif. 94089-1136, USA) was used to perform the calculations that generated the quadratic fit of the standard curve and to convert the sample optical density (OD) values to GLYAT4621 protein concentrations. The mean duplicate well values in ng/ml were used in the calculation of the reported GLYAT4621 concentration of each sample (ng/mg dry weight).

The quantitative range for the GLYAT4621 assay was 0.36 to 8.8 ng/ml. The lower limit of quantitation (LLOQ) in ng/mg dry weight for each tissue was based on extraction volume (μl) to weight ratios, the limit of quantitation for the ELISA in ng/ml, and the dilutions used for analysis. The sample LLOQ on a ng/mg dry weight basis for GLYAT4621 was 0.22 ng/mg dry weight for leaf and 0.22 ng/mg dry weight for seed.

The ZM-HRA ELISA method utilized a sequential "sandwich" format for the determination of the presence of ZM-HRA protein in maize plant tissue extracts. Standards (analyzed in triplicate wells) and diluted sample extracts (analyzed in duplicate wells) were incubated for one hour in stabilized 96-well plates that were precoated with a ZM-HRA-specific antibody. Unbound substances were washed from the plate, and a different ZM-HRA antibody conjugated to the enzyme horseradish peroxidase (HRP) was added to the wells. Bound ZM-HRA protein was sandwiched between the antibody coated on the plate and the antibody-HRP conjugate. At the end of the one hour incubation, unbound substances were washed from the plate. Detection of the bound ZM-HRA protein-antibody complex was accomplished by the addition of a substrate, which generated a colored product in the presence of HRP. The reaction was stopped with stop solution (hydrochloric acid) and the optical density of each well was determined using a Molecular Devices plate reader (Molecular Devices Corporation, 1311 Orleans Drive, Sunnyvale, Calif. 94089-1136, USA) with a wavelength setting of 450 nm minus 650 nm. SoftMax Pro software (Molecular Devices Corporation, 1311 Orleans Drive, Sunnyvale, Calif. 94089-1136, USA) was used to perform the calculations that generated the quadratic fit for the standard curve and converted the sample OD values to ZM-HRA protein concentrations. The mean concentration from the duplicate wells in ng/ml was used in the calculation of the reported ZM-HRA concentration of each sample (ng/mg dry weight).

The quantitative range for the ZM-HRA assay was 0.9 to 22 ng/ml. The lower limit of quantitation (LLOQ) in ng/mg dry weight for each tissue was based on extraction volume (μl) to weight ratios, the limit of quantitation for the ELISA in ng/ml, and the dilutions used for analysis. The sample LLOQ on a ng/mg dry weight basis for ZM-HRA was 0.54 ng/mg dry weight for leaf and 0.14 ng/mg dry weight for seed.

Means, standard error and P-values were calculated for plant height data. Means were calculated for herbicide injury scores. Means, ranges and standard deviations of protein expression data were calculated for each protein expressed in leaf and seed tissues.

The sprayed DP-098140-6 maize plants from both Generation 1 and Generation 2 showed no herbicide injury and were comparable to both generations of the non-sprayed control and non-sprayed DP-098140-6 maize plants (data not shown). Both generations of the glyphosate and the glyphosate/thifensulfuron/tribenuron tank mixture sprayed control maize resulted in 100% injury (Table 16). The thifensulfuron/tribenuron treatment resulted in 10 to 50% injury to the control at the 21 day post-treatment evaluation. As expected, the zm-hra gene within DP-098140-6 maize, allowed for enhanced tolerance to ALS-inhibiting herbicides, as demonstrated with the plant height measurements and photographs (Tables 17-18 and data not shown).

ELISA analysis indicated GLYAT4621 protein expression in all DP-098140-6 maize leaf samples except one and was not expressed (below LLOQ) in the control leaf samples except one. These exceptions were ascribed to miscalls during the greenhouse lateral flow strip test analysis. The GLYAT4621 protein was expressed in 10 out of 25 seed samples due to segregation (Table 19). ELISA analysis indicated ZM-HRA protein expression in all 98140 maize leaf samples except one and was not expressed (below LLOQ) in the control leaf samples except one. These exceptions were also ascribed to miscalls during the greenhouse strip test analysis. The ZM-HRA protein was expressed in only one of the segregating generation 1 seed samples (ascribed to a miscall during lateral flow strip test analysis) and in none of the generation 2 seed samples. The ZM-HRA protein was not expressed (below LLOQ) in any of the control seed samples (Table 20).

TABLE 15

Experimental Design

| Entry[1] | Event | Generation | No. of Plants | Herbicide Treatment |
|---|---|---|---|---|
| 1 | 98140 | 1 | 5 | Glyphosate |
| 2 | 98140 | 1 | 5 | Thifensulfuron/Tribenuron |
| 3 | 98140 | 1 | 5 | Glyphosate + Thifensulfuron/Tribenuron |
| 4 | 98140 | 1 | 5 | Non-Sprayed |
| 9 | Control | 1 | 5 | Glyphosate |
| 10 | Control | 1 | 5 | Thifensulfuron/Tribenuron |
| 11 | Control | 1 | 5 | Glyphosate + Thifensulfuron/Tribenuron |
| 12 | Control | 1 | 5 | Non-Sprayed |
| 13 | 98140 | 2 | 5 | Glyphosate |
| 14 | 98140 | 2 | 5 | Thifensulfuron/Tribenuron |
| 15 | 98140 | 2 | 5 | Glyphosate + Thifensulfuron/Tribenuron |
| 16 | 98140 | 2 | 5 | Non-Sprayed |
| 21 | Control | 2 | 5 | Glyphosate |
| 22 | Control | 2 | 5 | Thifensulfuron/Tribenuron |
| 23 | Control | 2 | 5 | Glyphosate + Thifensulfuron/Tribenuron |
| 24 | Control | 2 | 5 | Non-Sprayed |

[1]Entries 5-8 and 17-20 contained an event not specific to this summary report.

TABLE 16

Average Herbicide Injury Ratings for DP-098140-6 and Control Maize Post-Herbicide Treatment

| | | Average Herbicide Injury Rating | | | |
|---|---|---|---|---|---|
| | | Generation 1 | | Generation 2 | |
| | Herbicide Treatment | 14 Days Post-treatment | 21 Days Post-treatment | 14 Days Post-treatment | 21 Days Post-treatment |
| DP-098140-6 maize | Glyphosate | 0 | 0 | 0 | 0 |
| | Thifensulfuron/Tribenuron | 0 | 0 | 0 | 0 |
| | Glyphosate + Thifensulfuron/Tribenuron | 0 | 0 | 0 | 0 |
| | Non-Spray | 0 | 0 | 0 | 0 |
| Control maize | Glyphosate | 100 | 100 | 100 | 100 |
| | Thifensulfuron/Tribenuron | 0 | 12.5 | 0 | 25 |
| | Glyphosate + Thifensulfuron/Tribenuron | 100 | 100 | 100 | 100 |
| | Non-Spray | 0 | 0 | 0 | 0 |

TABLE 17

Statistical Comparison of Plant Height for DP-098140-6 and Control Maize - Generation 1

| Herbicide Treatment | Days Following Treatment | Maize Line | Least Square Means[2] (cm) | Standard Error | P-Value[1] |
|---|---|---|---|---|---|
| Glyphosate | 14 | 98140 | 103 | 1.30 | 0.0001 |
| | | Control | 0.00 | 1.30 | |
| | 21 | 98140 | 120 | 1.52 | 0.0001 |
| | | Control | 0.00 | 1.52 | |
| Thifensulfuron/Tribenuron | 14 | 98140 | 102 | 3.06 | 0.0033 |
| | | Control | 67.0 | 3.06 | |
| | 21 | 98140 | 118 | 3.18 | 0.0013 |
| | | Control | 66.4 | 3.18 | |
| Glyphosate + Thifensulfuron/Tribenuron | 14 | 98140 | 101 | 0.961 | 0.0001 |
| | | Control | 0.00 | 0.961 | |
| | 21 | 98140 | 116 | 1.50 | 0.0001 |
| | | Control | 0.00 | 1.50 | |
| Non-Spray | 14 | 98140 | 100 | 2.57 | 0.6562 |
| | | Control | 98.7 | 2.57 | |
| | 21 | 98140 | 113 | 3.45 | 0.7034 |
| | | Control | 111 | 3.45 | |

[1]P-value <0.05 indicates a statistically significant difference.
[2]Values of 0 cm indicate a visible plant that has died due to herbicide treatment.

TABLE 18

Statistical Comparison of Plant Height for 98140 and Control Maize - Generation 2

| Herbicide Treatment | Days Following Treatment | Maize Line | Least Square Means[2] (cm) | Standard Error | P-Value[1] |
|---|---|---|---|---|---|
| Glyphosate | 14 | 98140 | 101 | 1.55 | 0.0001 |
| | | Control | 0.00 | 1.55 | |
| | 21 | 98140 | 115 | 2.56 | 0.0001 |
| | | Control | 0.00 | 2.56 | |
| Thifensulfuron/Tribenuron | 14 | 98140 | 103 | 2.01 | 0.0001 |
| | | Control | 67.3 | 2.01 | |
| | 21 | 98140 | 119 | 1.79 | 0.0001 |
| | | Control | 67.8 | 1.79 | |
| Glyphosate + Thifensulfuron/Tribenuron | 14 | 98140 | 97.0 | 1.70 | 0.0001 |
| | | Control | 0.00 | 1.70 | |
| | 21 | 98140 | 111 | 2.86 | 0.0001 |
| | | Control | 0.00 | 2.86 | |
| Non-Spray | 14 | 98140 | 98.2 | 4.59 | 0.3777 |
| | | Control | 103 | 4.59 | |
| | 21 | 98140 | 120 | 4.88 | 0.3563 |
| | | Control | 114 | 4.88 | |

[1]P-value <0.05 indicates a statistically significant difference.
[2]Values of 0 cm indicate a visible plant that has died due to herbicide treatment.

TABLE 19

Summary of the Protein Concentration Results for GLYAT4621 in 98140 and Control Maize Samples

| Tissue Type | Number of samples (N) | ng/mg Tissue Dry Weight[5] Mean | Range[1] | Standard Deviation |
|---|---|---|---|---|
| | | 98140 Generation 1 | | |
| Leaf | 19[2] | 34 | 5.8-49 | 9.2 |
| Seed | 10[3] | 9.6 | 5.9-17 | 3.0 |
| | | 98140 Generation 2 | | |
| Leaf | 20 | 34 | 24-48 | 6.6 |
| Seed | 25 | 10 | 7.6-18 | 2.9 |
| | | Control Generation 1 | | |
| Leaf | 19[2] | 0 | 0 | 0 |
| Seed | 15[4] | 0 | 0 | 0 |
| | | Control Generation 2 | | |
| Leaf | 20 | 0 | 0 | 0 |
| Seed | 25 | 0 | 0 | 0 |

[1]Range denotes the lowest and highest individual values across all samples.
[2]One leaf sample excluded from summary statistics due to an apparent miscalled plant identification in the greenhouse.
[3]Only the non-segregating seed samples were used in summary statistics.
[4]The control seed samples were taken from the segregating null population of this event.
[5]For results below the sample LLOQ, a value of zero was assigned for calculation purposes.

TABLE 20

Summary of the Protein Concentration Results for ZM-HRA in DP-098140-6 and Control Maize Samples

| Tissue Type | Number of Samples (N) | ng/mg Tissue Dry Weight[3] Mean | Range[1] | Standard Deviation |
|---|---|---|---|---|
| | | 98140 Generation 1 | | |
| Leaf | 19[2] | 7.2 | 4.3-11 | 1.6 |
| Seed | 10[4] | 0.014 | 0-0.14 | 0 |
| | | 98140 Generation 2 | | |
| Leaf | 20 | 6.9 | 4.1-9.5 | 1.4 |
| Seed | 25[4] | 0[4] | 0-0 | 0 |

TABLE 20-continued

Summary of the Protein Concentration Results for ZM-HRA in DP-098140-6 and Control Maize Samples

| Tissue Type | Number of Samples (N) | ng/mg Tissue Dry Weight[3] Mean | Range[1] | Standard Deviation |
|---|---|---|---|---|
| Control Generation 1 | | | | |
| Leaf | 19[2] | 0 | 0 | 0 |
| Seed | 15 | 0 | 0 | 0 |
| Control Generation 2 | | | | |
| Leaf | 20 | 0 | 0 | 0 |
| Seed | 25 | 0 | 0 | 0 |

[1]Range denotes the lowest and highest individual values across all samples.
[2]One leaf sample excluded from summary statistics due to an apparent miscalled plant identification in the greenhouse.
[3]For results below the sample LLOQ, a value of zero was assigned for calculation purposes.
[4]All samples were below the LLOQ.

TABLE 26

Description of Genetic Elements in the T-DNA of PHP24279

| Location on T-DNA (base pair position) | Genetic Element | Size (base pairs) | Description |
|---|---|---|---|
| 1 to 25 | Right Border | 25 | T-DNA Right Border region, from Ti plasmid of *Agrobacterium tumefaciens* |
| 26 to 177 | Ti Plasmid Region | 152 | Non-functional sequence from Ti plasmid of *A. tumefaciens* |
| 178 to 210 | Polylinker Region | 33 | Region required for cloning genetic elements |
| 211 to 521 | pinII Terminator | 311 | Terminator region from *Solanum tuberosum* proteinase inhibitor II gene (Keil et al., 1986; An et al., 1989). (reverse orientation) |
| 522 to 537 | Polylinker Region | 33 | Region required for cloning genetic elements |
| 538 to 2454 | zm-hra Gene | 1917 | Modified endogenous *Zea mays* acetolactate synthase gene (Fang et al., 1992). (reverse orientation) |
| 2455 to 3115 | zm-als Promoter | 661 | Promoter region from *Zea mays* acetolactate synthase gene (Fang et al., 1992). (reverse orientation) |
| 3116 to 3189 | Polylinker Region | 74 | Region required for cloning genetic elements |
| 3190 to 3625 | CaMV 35S Enhancer | 436 | Enhancer region from the Cauliflower Mosaic Virus genome (Franck et al., 1980; Odell et al., 1985). |
| 3626 to 3648 | Polylinker Region | 23 | Region required for cloning genetic elements |
| 3649 to 4086 | CaMV 35S Enhancer | 438 | Enhancer region from the Cauliflower Mosaic Virus genome (Franck et al., 1980; Odell et al., 1985). |
| 4087 to 4093 | Polylinker Region | 7 | Region required for cloning genetic elements |
| 4094 to 4531 | CaMV 35S Enhancer | 438 | Enhancer region from the Cauliflower Mosaic Virus genome (Franck et al., 1980; Odell et al., 1985). |
| 4532 to 4566 | Polylinker Region | 35 | Region required for cloning genetic elements |
| 4567 to 5466 | ubiZM1 Promoter | 900 | Promoter region from *Zea mays* ubiquitin gene (Christensen et al., 1992). |
| 5467 to 5549 | ubiZM1 5' UTR | 83 | 5' untranslated region from *Zea mays* ubiquitin gene (Christensen et al., 1992). |
| 5550 to 6558 | ubiZM1 Intron | 1009 | Intron region from *Zea mays* ubiquitin gene (Christensen et al., 1992). |
| 6559 to 6586 | Polylinker Region | 28 | Region required for cloning genetic elements |
| 6587 to 7030 | glyat4621 Gene | 444 | Synthetic glyphosate N-acetyltransferase gene (Castle et al., 2004. Siehl et al., 2007). |
| 7031 to 7046 | Polylinker Region | 16 | Region required for cloning genetic elements |
| 7047 to 7362 | pinII Terminator | 316 | Terminator region from *Solanum tuberosum* proteinase inhibitor II gene (Keil et al., 1986; An et al., 1989). |
| 7363 to 7415 | Ti Plasmid Region | 53 | Non-functional sequence from Ti plasmid of *A. tumefaciens* |
| 7416 to 7440 | Left Border | 25 | T-DNA Left Border region, from Ti plasmid of *Agrobacterium tumefaciens* |

Example 7

Molecular and Genetic Characterization of DP-098140-6 Corn

To characterize the DNA insertion in DP-098140-6 corn, Southern blot analysis was conducted. Individual plants of the T0S3 generation were analyzed by Southern blot to determine the number of each of the genetic elements of the expression cassettes inserted and to verify the integrity of the PHP24279 T-DNA was maintained upon integration. The integration pattern of the insertion in DP-098140-6 corn was investigated with EcoR V and Spe I restriction enzymes. Southern blot analysis was conducted on individual plants of two generations, BC0S2 and BC1 to confirm insert stability across generations and to verify the absence of backbone sequences from plasmid PHP24279. The BC1S1 generation was also analyzed by Southern blot to confirm insert stability within a fourth generation.

Seeds from the T0S3, BC0S2, BC1, and BC1S1 generations of DP-098140-6 corn were planted and leaf tissue harvested from individual plants was used for genomic DNA extraction.

Seeds from the unmodified corn varieties PHWVZ and PH09B were planted and leaf tissue harvested from individual plants was used for genomic DNA extraction. PHWVZ and PH09B control DNA was used as a negative control to help interpret hybridization results since several probes (zm-hra, als promoter, ubiZM1 promoter, and ubiZM1 intron) cross-hybridize with endogenous corn sequences.

Plasmid DNA from PHP24279 was prepared from *E. coli* (Invitrogen, Carlsbad, Calif.) and was used as a positive control for Southern analysis to verify probe hybridization and to verify sizes of internal fragments. The plasmid stock was a copy of the plasmid used for *Agrobacterium*-mediated transformation experiments to produce DP-098140-6 corn and was digested with restriction enzymes to confirm the plasmid map. The probes used in this study were derived from plasmid PHP24279 or from a plasmid containing equivalent genetic elements.

DNA molecular weight markers for gel electrophoresis and Southern blot analysis were used to determine approximate molecular weights. For Southern analysis, DNA Molecular Weight Marker VII, digoxigenin (DIG) labeled (Roche, Indianapolis, Ind.), was used as a size standard for hybridizing fragments. ΦX174 RF DNA/Hae III Fragments (Invitrogen, Carlsbad, Calif.) was used as a molecular weight standard to determine sufficient migration and separation of the fragments on the gel.

Genomic DNA was extracted from leaf tissue harvested from individual plants as described above. The tissue was pulverized in tubes containing grinding beads using a Geno/Grinder™ (SPEX CertiPrep, Inc., Metuchen, N.J.) instrument and the genomic DNA isolated using a urea-based procedure (modification from Chen and Dellaporta, 1994). Approximately 1 gram of ground tissue was extracted with 5 ml Urea Extraction Buffer (7 M Urea, 0.34 M NaCl, 0.05 M Tris-HCl, pH 8.0, 0.02 M EDTA, 1% N-Lauroylsarcosine) for 12-30 minutes at 37° C., followed by two extractions with phenol/chloroform/isoamyl alcohol (25:24:1) and one extraction with water saturated chloroform. The DNA was precipitated from the aqueous phase by the addition of $\frac{1}{10}$ volume of 3 M NaOAc (pH 5.2) and 1 volume of isopropyl alcohol, followed by centrifugation to pellet the DNA. After washing the pellet twice with 70% ethanol, the DNA was dissolved in 0.5 ml TE buffer (10 mM Tris, 1 mM EDTA, pH 7.5) and treated with 10 µg Ribonuclease A for 15 minutes at 37° C. The sample was extracted once with phenol:chloroform:isoamyl alcohol (25:24:1) and once with water saturated chloroform, followed by precipitation with isopropyl alcohol and washing with 70% ethanol. After drying, the DNA was re-dissolved with 0.5 ml TE buffer and stored at 4° C.

Following extraction, the DNA was quantified on a spectrofluorometer using PicoGreen® reagent (Molecular Probes, Inc., Eugene, Oreg.) following a standard procedure. The DNA was also visualized on an agarose gel to confirm quantitation values from the PicoGreen® analysis and to determine DNA quality.

Phenotypic analysis of DP-098140-6 corn plants and control plants was carried out by the use of lateral flow devices able to detect the GLYAT4621 protein to confirm the absence or presence of the GLYAT4621 protein in material used for Southern blot analysis.

Leaf extract was prepared by grinding leaf punches to homogeneity in 500 µl of extraction buffer (20 mM Tris (pH 7.5), 67 mM NaCl, 0.5% Tween 20). Lateral flow devices (EnviroLogix, Inc., Portland, Me.) were placed in the homogenate and allowed to develop. After incubation, the results were read from the lateral flow devices. A single stripe indicated a negative result and a double stripe indicated the sample was positive for the GLYAT4621 protein.

A preliminary Southern blot analysis of DNA isolated from all DP-098140-6 corn plants from generations T0S3, BC0S2, and BC1 was used to verify the presence of both the glyat4621 and zm-hra genes. Methods for this preliminary characterization are described below. Final Southern blot analysis was carried out on a subset of DP-098140-6 corn plants from these three generations and the BC1S1 generation.

Genomic DNA samples extracted from selected DP-098140-6 corn and control corn plants were digested with restriction enzymes following a standard procedure. Approximately 4 µg of genomic DNA was digested in a volume of 100 µl using 50 units of enzyme according to manufacturer's recommendations. The digestions were carried out at 37° C. for three hours, followed by ethanol precipitation with $\frac{1}{10}$ volume of 3 M NaOAc (pH 5.2) and 2 volumes of 100% ethanol. After incubation at 4° C. and centrifugation, the DNA was allowed to dry and re-dissolved in TE buffer. The reference plasmid, PHP24279, was spiked into a control plant DNA sample in an amount equivalent to approximately one or three gene copies per corn genome and digested with the same enzyme to serve as a positive control for probe hybridization and to verify sizes of internal fragments on the Southern blot.

Following restriction enzyme digestion, the DNA fragments produced were electrophoretically separated by size through an agarose gel and a molecular weight standard [ΦX174 RF DNA/Hae III Fragments (Invitrogen)] was used to determine sufficient migration and separation of the fragments on the gel. DIG labeled DNA Molecular Weight Marker VII (Roche), visible after DIG detection as described below, was used to determine hybridizing fragment size on the Southern blots.

Agarose gels containing the separated DNA fragments were depurinated, denatured, and neutralized in situ, and transferred to a nylon membrane in 20×SSC buffer (3M NaCl, 0.3 M Sodium Citrate) using the method as described for the TURBOBLOTTER™ Rapid Downward Transfer System (Schleicher & Schuell, Keene, N.H.). Following transfer to the membrane, the DNA was bound to the membrane by UV crosslinking (Stratalinker, Stratagene, La Jolla, Calif.).

Probes for the ubiZM1 promoter, ubiZM1 intron, glyat4621 (SEQ ID NO: 33), pinII terminator, als promoter, zm-hra (SEQ ID NO: 31 and 32), and 35S enhancer were used to detect genes and elements within the insertion. Backbone regions (virG, tet, spc, LB, and RB probes) of the PHP24279 plasmid were used to verify absence of plasmid backbone DNA in DP-098140-6 corn. DNA fragments of the probe elements were generated by PCR from plasmid PHP24279 or a plasmid with equivalent elements using specific primers. PCR fragments were electrophoretically separated on an agarose gel, excised and purified using a gel purification kit (Qiagen, Valencia, Calif.). DNA probes were generated from these fragments by PCR that incorporated a DIG labeled nucleotide, [DIG-11]-dUTP, into the fragment. PCR labeling of isolated fragments was carried out according to the procedures supplied in the PCR DIG Probe Synthesis Kit (Roche).

The DNA fragments bound to the nylon membrane were detected as discrete bands when hybridized to a labeled probe. Labeled probes were hybridized to the target DNA on the nylon membranes for detection of the specific fragments using the procedures essentially as described for DIG Easy Hyb solution (Roche). After stringent washes, the hybridized DIG-labeled probes and DIG-labeled DNA standards were visualized using CDP-Star Chemiluminescent Nucleic Acid Detection System with DIG Wash and Block Buffer Set (Roche). Blots were exposed to X-ray film for one or more time points to detect hybridizing fragments and to visualize molecular weight standards. Images were digitally captured by detection with the Luminescent Image Analyzer LAS-3000 (Fujifilm Medical Systems, Stamford, Conn.). Digital images were compared to original X-ray film exposures as verification for use in this report. The sizes of detected bands were documented for each digest and each probe.

Following hybridization and detection, membranes were stripped of DIG-labeled probe to prepare the blot for subsequent re-hybridization to additional probes. Membranes were rinsed briefly in distilled, de-ionized water and then stripped in a solution of 0.2 M NaOH and 0.1% SDS at 37-40° C. with constant shaking. The membranes were then rinsed in 2×SSC and either used directly for subsequent hybridizations or stored at 4° C. or −20° C. for later use. The alkali-based stripping procedure effectively removes probes labeled with the alkali-labile DIG.

Transgene Copy Number and Insertion Integrity

The integration pattern of the insertion in DP-098140-6 corn was investigated with EcoR V digestion to determine copy number and with Spe I digestion to determine insertion integrity. Southern blots were hybridized with several probes to confirm copy number and integrity of each genetic element. The ubiZM1 promoter, ubiZM1 intron, and glyat4621 probes were used to characterize the glyat4621 cassette (Table 21 and data not shown). The als promoter and zm-hra probes were used to characterize the zm-hra cassette (Table 21 and data not shown). The 35S enhancer and pinII terminator probes were used to characterize genetic elements that are associated with both cassettes (Table 21 and data not shown).

TABLE 21

Description of DNA Probes Used for Southern Blot Hybridization

| Probe Name | Genetic Element | Position on PHP24279 T-DNA (bp to bp) | Position on PHP24279 Plasmid (bp to bp) | Probe Length (bp) |
|---|---|---|---|---|
| ubiZM1 promoter | ubiZM1 promoter | 4602 to 5460 | 22689 to 23457 | 859 |
| ubiZM1 intron | ubiZM1 5' UTR and intron | 5472 to 6551 | 23559 to 24638 | 1080 |
| glyat4621 | glyat4621 gene | 6587 to 7021 | 24674 to 25108 | 435 |
| als promoter | als promoter | 2503 to 3101 | 20590 to 21188 | 599 |
| zm-hra[1] | zm-hra gene | 538 to 1468 | 18625 to 19555 | 931 |
|  |  | 1490 to 2259 | 19577 to 20346 | 770 |
| pinII terminator | pinII terminator | 235 to 468[2] | 18322 to 18555[2] | 234 |
|  |  | 7100 to 7333[2] | 25187 to 25420[2] |  |
| 35S enhancer | CaMV 35S enhancer | 3192 to 3611[3] | 21279 to 21698[3] | 420 |
|  |  | 3653 to 4072[3] | 21740 to 22159[3] |  |
|  |  | 4097 to 4513[3] | 22184 to 22603[3] |  |
| virG | virG gene | N/A | 2512 to 3255 | 744 |
| tet[1] | Tetracycline resistance gene | N/A | 32556 to 33094 | 539 |
|  |  |  | 33200 to 33657 | 458 |
| spc | Spectinomycin resistance gene | N/A | 26707 to 27481 | 775 |

TABLE 21-continued

Description of DNA Probes Used for Southern Blot Hybridization

| Probe Name | Genetic Element | Position on PHP24279 T-DNA (bp to bp) | Position on PHP24279 Plasmid (bp to bp) | Probe Length (bp) |
|---|---|---|---|---|
| LB | Region on the plasmid backbone adjacent to the left T-DNA border | N/A | 25552 to 25897 | 346 |
| RB | Region on the plasmid backbone adjacent to the right T-DNA border | N/A | 17654 to 18043 | 390 |

*Abbreviations: N/A—Not Applicable, these are not present on the PHP24279 T-DNA.

[1] Two non-overlapping segments were generated for this probe and were combined for hybridization. The bp positions provided are the positions of each different segment.

[2] There are two copies of the pinII terminator on PHP24279 and the PHP24279 T-DNA. The bp positions provided are the positions of each separate copy.

[3] There are three copies of the 35S enhancer on PHP24279 and the PHP24279 T-DNA. The bp positions provided are the positions of each separate copy.

Predicted and observed hybridization bands are described in Tables 22, 24, and 27 for probes unique to the glyat4621 cassette, unique to the zm-hra cassette, and for probes associated with both cassettes, respectively. The ubiZM1 promoter, ubiZM1 intron, als promoter, and zm-hra probes all hybridize to sequences in both control and DP-098140-6 corn genomic DNA. Hybridizing bands present in control corn DNA were determined to be from the endogenous corn genome and are thus not part of the T-DNA insertion. These bands are indicated in Tables 22 and 24 by asterisks (*) and gray shading. Some variation in sample loading, gel electrophoresis and transfer, and hybridization intensity affected the visibility of faint endogenous bands between different generations and samples within generations.

TABLE 22

Predicted and Observed Hybridizing Bands on Southern Blots with Probes Unique to the glyat4621 Cassette

| Probe | Restriction Enzyme | Predicted Fragment Size from PHP24279[1] (bp) | Predicted Fragment Size from PHP24279 T-DNA[2] (bp) | Observed Fragment Size in DP-098140-6 Corn[3] (bp) |
|---|---|---|---|---|
| ubiZM1 promoter | EcoR V | 11178 | >3800[4] | ~6100 |
|  |  |  |  | >8600* |
| ubiZM1 intron | EcoR V | 11178 | >3800[4] | ~6100 |
|  |  |  |  | >8600* |
|  |  |  |  | >8600* |
|  |  |  |  | ~7000* |
| glyat4621 | EcoR V | 11178 | >3800[4] | ~6100 |
| ubiZM1 promoter | Spe I | 6773 | 6773 | 6773[5] |
|  |  |  |  | >8600* |
| ubiZM1 intron | Spe I | 6773 | 6773 | 6773[5] |
|  |  |  |  | >8600* |
|  |  |  |  | ~8600* |
|  |  |  |  | ~7400* |
|  |  |  |  | ~4000* |
|  |  |  |  | ~2700* |
| glyat4621 | Spe I | 6773 | 6773 | 6773[5] |

An asterisk (*) and gray shading indicates the designated band is due to probe hybridization to endogenous corn genome sequences, as determined by the presence of the same band in all lanes, both DP-098140-6 corn and control. Certain endogenous bands may be difficult to discern on a printed copy but are visible on the original film.

[1] Predicted fragment sizes for hybridization to samples containing the plasmid positive control are based on the PHP24279 plasmid map.

[2] Predicted fragment sizes for DP-098140-6 corn are based on the map of the PHP24279 T-DNA.

[3] Observed fragment sizes are considered approximate from these analyses and are based on the indicated sizes of the DIG-labeled DNA Molecular Weight Marker VII fragments on the Southern blots. Due to incorporation of DIG molecules for visualization, the marker fragments typically run approximately 5-10% larger than their actual indicated molecular weight. The sizes of fragments not corresponding directly to plasmid fragments are rounded to the nearest 100 bp.

[4] Minimum fragment size predicted based on an intact insertion of the T-DNA from PHP24279. Fragment size is rounded to the nearest 100 bp.

[5] Observed fragment size is the same as the predicted fragment size based on equivalent migration on the Southern blots.

TABLE 24

Predicted and Observed Hybridizing Bands on Southern Blots with Probes Unique to the zm-hra Cassette

| Probe | Restriction Enzyme | Predicted Fragment Size from PHP24279[1] (bp) | Predicted Fragment Size from PHP24279 T-DNA[2] (bp) | Observed Fragment Size in DP-098140-6 Corn[3] (bp) |
|---|---|---|---|---|
| als promoter | EcoR V | 9691 | >3700[4] | >8600<br>~7400* |
| zm-hra | EcoR V | 9691 | >3700[4] | >8600<br>~8600*[5]<br>~8600*[5]<br>~7400*<br>~4700* |
| als promoter | Spe I | 6773 | 6773 | 6773[6]<br>~5500* |
| zm-hra | Spe I | 6773 | 6773 | 6773[6]<br>~5300*<br>~5200*<br>~4700* |

An asterisk (*) and gray shading indicates the designated band is due to probe hybridization to endogenous corn genome sequences, as determined by the presence of the same band in all lanes, both DP-098140-6 corn and control. Certain endogenous bands may be difficult to discern on a printed copy but are visible on the original film. Not all endogenous bands are the same in all samples due to genomic differences in varieties used in the breeding process to produce the different generations ananlyzed.

[1]Predicted fragment sizes for hybridization to samples containing the plasmid positive control are based on the PHP2479 plasmid map.

[2]Predicted fragment sizes for DP-098140-6 corn are based on the map of the PHP24279 T-DNA.

[3]Observed fragment sizes are considered approximate from these analyses and are based on the indicated sizes of the DIG-labeled DNA Molecular Weight Marker VII fragments on the Southern blots. Due to incorporation of DIG molecules for visualization, the marker fragments typically run approximately 5-10% larger than their actual indicated molecular weight. The sizes of fragments not corresponding directly to plasmid fragments are rounded to the nearest 100 bp.

[4]Minimum fragment size predicted based on an intact insertion of the T-DNA from PHP24279. Fragment size is rounded to the nearest 100 bp.

[5]Not all endogenous bands are observed in all generations due to allelic differences in backgrounds. Also, variations in sample loading, gel electrophoresis and transfer, and hybridization intensity affect the visibility of faint endogenous bands between different generations and samples within generations.

[6]Observed fragment size is the same as the predicted fragment size based on equivalent migration on the Southern blots.

Figure 5:
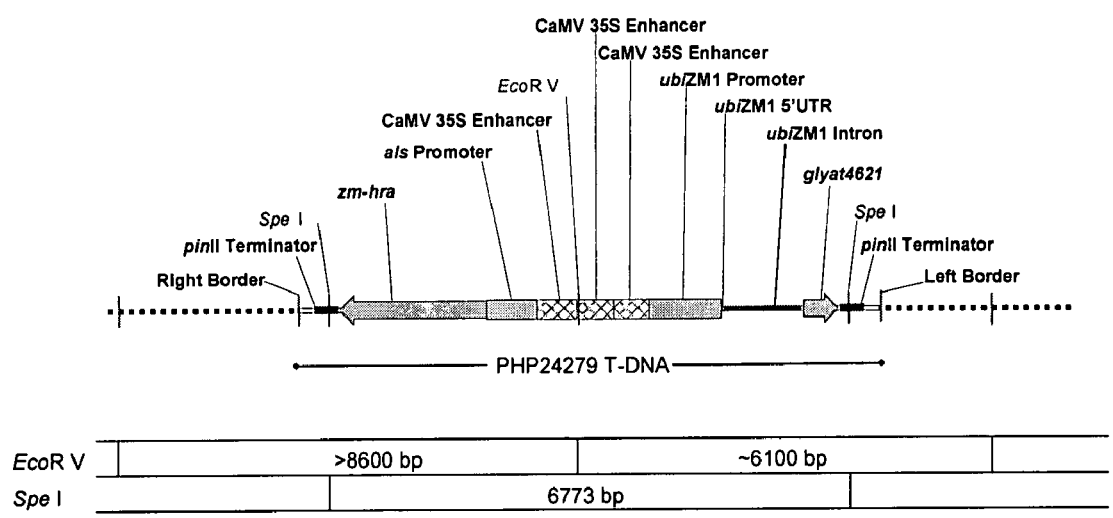
FIG. 5 provides a schematic map of the DNA insertion in DP-098140-6 with EcoR V and Spe I sites indicated. The dotted line represents the genomic regions flanking the inserted PHP24279 T-DNA.

Based on the Southern blot analyses as discussed below, it was determined that a single, intact PHP24279 T-DNA has been inserted into the genome of DP-098140-6 corn as diagramed in the insertion map (FIG. 5).

Copy Number

The EcoR V digest provides information about the number of copies of the genetic elements integrated into the genome of DP-098140-6 corn as there is a single restriction enzyme site in the PHP24279 T-DNA at base pair (bp) position 3651 and any additional sites would fall outside the T-DNA sequence in the corn genome. Hybridization with the probes from each cassette, except for the 35S enhancer probe, would indicate the number of copies of each element found in DP-098140-6 corn based on the number of hybridizing bands (e.g. one hybridizing band indicates one copy of the element). There are two copies of the pinII terminator; one located in each gene cassette on either side of the EcoR V site, so two hybridizing bands would be expected with this probe for a single T-DNA insertion. There are three copies of the 35S enhancer element in the T-DNA; however, since the EcoR V site is located between two of the copies, only two hybridizing bands would be expected. Predicted and observed fragment sizes for DP-098140-6 corn with EcoR V are given in Table 22 for the glyat4621 cassette, in Table 24 for the zm-hra cassette, and in Table 27 for elements associated with both cassettes.

TABLE 27

Predicted and Observed Hybridizing Bands on Southern Blots with Probes Common to glyat4621 and zm-hra Cassettes

| Probe | Restriction Enzyme | Predicted Fragment Size from PHP24279[1] (bp) | Predicted Fragment Size from PHP24279 T-DNA[2] (bp) | Observed Fragment Size in DP-098140-6 Corn[3] (bp) |
|---|---|---|---|---|
| pinII terminator | EcoR V | 11178 | >3800[4] | >8600 |
|  |  | 9691 | >3700[4] | ~6100 |
| 35S enhancer | EcoR V | 11178 | >3800[4] | >8600 |
|  |  | 9691 | >3700[4] | ~6100 |
| pinII terminator | Spe I | 42785 | 6773 | 6773[5] |
|  |  | 6773 | >400[4] | ~4900 |
|  |  | 813 | >300[4] | ~450 |
| 35S enhancer | Spe I | 6773 | 6773 | 6773[5] |

[1]Predicted fragment sizes for hybridization to samples containing the plasmid positive control are based on the PHP24279 plasmid map.

[2]Predicted fragment sizes for DP-098140-6 corn are based on the map of the PHP24279 T-DNA.

[3]Observed fragment sizes are considered approximate from these analyses and are based on the indicated sizes of the DIG-labeled DNA Molecular Weight Marker VII fragments on the Southern blots. Due to incorporation of DIG molecules for visualization, the marker fragments typically run approximately 5-10% larger than their actual indicated molecular weight. The sizes of fragments not corresponding directly to plasmid fragments are rounded to the nearest 100 bp if >500 bp, or to the nearest 50 bp if <500 bp.

[4]Minimum fragment size predicted based on an intact insertion of the T-DNA from PHP24279. Fragment size is rounded to the nearest 100 bp.

[5]Observed fragment size is the same as the predicted fragment size based on equivalent migration on the Southern blots.

A single copy of the unique elements of the glyat4621 cassette was inserted into DP-098140-6 corn. The ubiZM1 promoter, ubiZM1 intron, and glyat4621 probes were hybridized to EcoR V-digested genomic DNA from individual DP-098140-6 corn plants of the T0S3 generation (Table 22). Each of the probes hybridized to the same single fragment of approximately 6100 bp (Table 22), indicating a single copy insertion with the expected arrangement of genetic elements on the inserted fragment in DP-098140-6 corn. The ubiZM1 promoter and ubiZM1 intron probes are homologous to elements endogenous to the corn genome and therefore each probe also hybridized to bands in control corn samples (Table 22).

Likewise, a single copy of each element exclusive to the zm-hra cassette was inserted into DP-098140-6 corn. The two unique elements comprising this cassette—the als promoter and zm-hra gene—were used as probes to determine number of copies inserted. Each of the two probes hybridized to the same single fragment of greater than 8600 base pairs (bp) (Table 24), indicating a single copy insertion with the expected arrangement of genetic elements on the inserted fragment in DP-098140-6 corn. The probes of this cassette are also homologous to elements endogenous to the corn genome and therefore each probe also hybridized to bands in control corn samples.

The pinII terminator is present in both the glyat4621 and zm-hra cassettes. The three copies of the 35S enhancer element are located between the two expression cassettes. Due to the location of the EcoR V restriction enzyme site between two of the three copies of the 35S enhancer at bp position 3651 (FIG. 6), it would be expected that the pinII terminator and 35S enhancer probes would hybridize to the same fragments that contain the glyat4621 or zm-hra gene cassettes. In both cases, hybridization of the EcoR V Southern blots with these probes resulted in the detection of both the 6100 bp band associated with the glyat4621 cassette and the greater than 8600 bp band associated with the zm-hra cassette (Table 27 and data not shown). In the case of the 35S enhancer probe, the band of greater than 8600 bp is substantially fainter than the approximately 6100 bp band as it is the band containing a single copy of the enhancer element, compared to the 6100 bp band which contains two copies of the 35S enhancer (data not shown). The presence of only two hybridizing bands for the pinII terminator and 35S enhancer probes, corresponding to the hybridizing bands noted above for the other components of the two gene cassettes, is further indication that there is a single copy of the PHP24279 T-DNA, in its expected arrangement, inserted in the DP-098140-6 corn genome.

Insertion Integrity

Spe I digestion was used to verify that the inserted T-DNA containing both of the glyat4621 and zm-hra cassettes was complete and intact in DP-098140-6 corn. There are two Spe I sites in the PHP24279 T-DNA (base pair positions 396 and 7169) which are located within the pinII terminator elements found on the ends of each gene expression cassette (FIG. 6). Hybridization with the probes of the glyat4621 and zm-hra cassettes confirmed that all the elements were found on the expected internal 6773 bp fragment. In addition, the pinII terminator probe hybridized to two other expected border fragments, due to the locations of the Spe I sites within the terminator. Expected and observed fragment sizes with Spe I are given in Table 22 for the glyat4621 cassette, Table 24 for the zm-hra cassette, and in Table 27 for elements associated with both cassettes.

The ubiZM1 promoter, ubiZM1 intron, and glyat4621 probes for the glyat4621 cassette hybridized to a single insertion-derived band of 6773 bp that matched the plasmid control band (Table 22, data not shown). Similarly, the probes for the zm-hra cassette (als promoter and zm-hra) hybridized to the same internal 6773 bp band (Table 24, data not shown). The 35S enhancer and pinII terminator probes also hybridized to the expected internal band of 6773 bp (Table 27, data not shown). The size of the band for each probe was confirmed by hybridization to the PHP24279 plasmid fragment corresponding to the T-DNA (data not shown). Because these probes hybridized to the same internal fragment of the predicted size, the PHP24279 T-DNA in DP-098140-6 corn was determined to be intact and all elements of the cassette were confirmed on this fragment.

In addition to the internal 6773 bp band, the pinII terminator probe hybridized to two additional bands, one of about 4900 bp and one of about 450 bp (Table 27, data not shown). These additional bands are due to the location of the Spe I restriction site within the pinII terminator probe region, leading to hybridization of the probe to two border fragments for an intact insertion of the PHP24279 T-DNA. The presence of the two additional hybridizing bands indicates that the pinII terminators in the T-DNA are intact, and serve as additional confirmation that the complete PHP24279 T-DNA was inserted into DP-098140-6 corn.

As stated previously, the ubiZM1 promoter, ubiZM1 intron, als promoter, and zm-hra probes are homologous to elements endogenous to the corn genome and therefore each probe hybridized to bands in control corn samples (Tables 22 and 24, data not shown).

Stability of the Insertion Across Generations

Southern blot analysis was conducted using EcoR V on three generations of 98140 corn; BC0S2, BC1, and BC1S1, to verify the stability of the insertion in 98140 corn as demonstrated by identical hybridization patterns in all generations. As discussed earlier, the EcoR V restriction enzyme has a single site (bp position 3651) located within the PHP24279 T-DNA (FIG. 6) and will generate a unique event-specific hybridization pattern for 98140 corn when hybridized to the glyat4621 and zm-hra probes. This analysis would confirm event stability across generations as changes to the insertion structure in 98140 corn would be detected. A band of approximately 6100 bp would be expected with the glyat4621 probe to confirm stability across generations (Table 22). Likewise for the zm-hra probe, a band of greater than 8600 bp would be expected to confirm stability across generations (Table 24). As described in detail below, all three generations analyzed, BC0S2, BC1, and BC1S1, showed identical hybridization patterns consistent with the T0S3 analysis confirming the stability of inheritance of the insertion in 98140 corn.

Genomic DNA from the BC0S2 and BC1 generations of 98140 corn was digested with EcoR V and hybridized to the glyat4621 and zm-hra probes to confirm stability across generations (data not shown). A band of approximately 6100 bp specific to 98140 corn hybridized to the glyat4621 probe in both generations (Table 22). With the zm-hra probe, a single band of greater than 8600 bp specific to 98140 corn was present in both generations (Table 24). In addition to the greater than 8600 bp band, the zm-hra probe also hybridized to additional bands that were determined to be endogenous to the corn genome since these bands were present in both 98140 corn and control corn plants (data not shown). The consistency of hybridization results from both the glyat4621 and zm-hra probes confirmed that the insertion of PHP24279 T-DNA in 98140 corn remained stable across the BC0S2 and BC1 generations. In addition, the bands observed resulting from the 98140 insertion in these two generations were the same size as the bands seen with the same probes on the EcoR V Southern blots of the T0S3 generation described above (data not shown), indicating the 98140 insertion is stable across all three generations. There is expected variation in the endogenous bands seen with the zm-hra probe between the 98140 corn plants from the differing generations, due to allelic differences between the original transformed corn line and the back-cross parent lines that are not associated with the 98140 insertion.

Plants from a segregating BC1S1 generation of 98140 corn were also analyzed by Southern blot. Genomic DNA of the BC1S1 generation was digested with EcoR V and hybridized to the glyat4621 and zm-hra probes. In plants containing the 98140 corn insertion, a band of approximately 6100 bp was observed with the glyat4621 probe (Table 22 and data not shown) and a band of greater than 8600 bp specific to 98140 corn was observed with the zm-hra probe (Table 24 and data not shown). As in previous analyses, the zm-hra probe hybridized to additional bands in 98140 corn and control samples which were due to endogenous sequences within the corn genome (data not shown). Variations in the endogenous bands in the BC1S1 generation are due to segregation of alleles from the parent lines, and are not due to a change in the 98140 insertion. Null segregant plants did not hybridize to the glyat4621 probe and showed only the endogenous hybridization observed in control plants with the zm-hra probe (data not shown). Hybridization results from both the glyat4621 and zm-hra probes were consistent with the results from the T0S3, BC0S2, and BC1 generations described above and confirmed the stability of inheritance of the insertion during traditional corn breeding.

Thus, Southern blot analysis of the T0S3, BC0S2, BC1, and BC1S1 generations of 98140 corn using the glyat4621 and zm-hra probes resulted in identical hybridization patterns on EcoR V digests of all four generations. The consistent hybridization patterns indicate that the T-DNA insertion is stably inherited across generations.

Inheritance of the Traits in DP-098140-6 Corn

Chi-square analysis of trait inheritance data from four different generations (BC0S1, BC1S1, BC2 and BC3) was performed to determine the heritability and stability of the glyat4621 and zm-hra genes in DP-098140-6 corn. The plants from the BC0S1 and BC1S1 generations were expected to segregate 3:1, and the plants from the BC2 and BC3 generations were expected to segregate 1:1 for the presence of the glyat4621 and zm-hra genes.

In order to confirm the expected segregation ratios, polymerase chain reaction (PCR) analysis was performed on leaf punches from seedlings. Qualitative PCR analysis for the glyat4621 and zm-hra genes was conducted on all plants.

Results from the segregation analysis are summarized in Table 23. In every case, plants that were positive for the glyat4621 gene were also positive for the zm-hra gene and vice versa, confirming co-segregation of the two genes as expected. To confirm that glyat4621 and zm-hra genes segregate according to Mendel's laws of genetics, chi-square analysis was performed. All P-values were greater than 0.05, indicating no statistically significant differences between the observed and expected frequencies of the glyat4621 and/or zm-hra genes in four generations of DP-098140-6 corn. The results of this analysis are consistent with the finding of a single locus of insertion of the glyat4621 and zm-hra genes that segregates in DP-098140-6 corn progeny according to Mendel's laws of genetics. The stability of the insert has been demonstrated in four generations of self- and cross-pollinations. See Table 23.

TABLE 23

Comparison of Observed and Expected Segregation Ratios for 98140 Corn

| | Observed | | | Expected | | |
| --- | --- | --- | --- | --- | --- | --- |
| Generation | Positive for glyat4621 and zm-hra genes | Negative for glyat4621 and zm-hra genes | Expected Ratio | Positive for glyat4621 and zm-hra genes | Negative for glyat4621 and zm-hra genes | Chi-Square Test P-value |
| BC0S1 | 55 | 22 | 3:1 | 57.75 | 19.25 | 0.5537 |
| BC1S1 | 45 | 20 | 3:1 | 48.75 | 16.25 | 0.3519 |
| BC2 | 51 | 48 | 1:1 | 49.5 | 49.5 | 0.8407 |
| BC3 | 52 | 45 | 1:1 | 48.5 | 48.5 | 0.5424 |

SUMMARY AND CONCLUSIONS

Southern blot analysis was conducted to characterize the DNA insertion in DP-098140-6 corn. The analysis confirmed that a single, intact PHP24279 T-DNA has been inserted into the corn genome to produce DP-098140-6 corn. A single copy of each of the elements of the glyat4621 and zm-hra expression cassettes was present, along with the three 35S enhancer elements between the two cassettes, and the integrity of the PHP24279 T-DNA was maintained. The analysis confirmed the stability of the insertion in DP-098140-6 corn across the T0S3, BC1S1, BC0S2, and BC1 generations, thus confirming stability of inheritance during traditional breeding procedures.

Inheritance studies confirmed that the insert segregated in normal Mendelian fashion. None of the P-values obtained in the studies indicated a statistically significant difference between observed and expected segregation ratios for the glyat4621 and zm-hra genes over four different plant generations. The results are consistent with the molecular characterization data, which indicates stable integration of the glyat4621 and zm-hra transgenes at a single site in the corn genome.

A sufficient number of fixed plants can be readily obtained by planting the seed and spraying the resulting plants with glyphosate. The corn seed is treated with MAXIM XL fungicide. Safety glasses and chemical resistant gloves should be worn when handling the seed. Do not ingest seed.

TABLE 28

Summary Table of SEQ ID NOS

| SEQ ID NO | Description |
|---|---|
| 1 | Right border genomic sequence |
| 2 | Left border genomic sequence |
| 3 | complete internal transgene |
| 4 | complete flanking and complete transgene insert |
| 5 | right flanking genomic/right border transgene (10 nt/10 nt) |
| 6 | Left flanking genomic/left border transgene (10 nt/10 nt) |
| 7 | Right flanking genomic/right border transgene (20 nt/20 nt) |
| 8 | Left flanking genomic/left border transgene (20 nt/20 nt) |
| 9 | Right flanking genomic/right border transgene (30 nt/30 nt) |
| 10 | Left flanking genomic/left border transgene (30 nt/30 nt) |
| 11 | Left flanking genomic/complete transgene |
| 12 | Right flanking genomic/complete transgene |
| 13 | Primer 100235 |
| 14 | primer 99878 |
| 15 | Primer 99885 |
| 16 | Primer 100240 |
| 17 | Primer 102588 (primer pair for 18) |
| 18 | Primer 102589 |
| 19 | Taqman MOB probe 102590 |
| 20 | Primer 06-O-1734 |
| 21 | Primer 06-O-1738 |
| 22 | Primer 02-O-197 (invertase) |
| 23 | Primer 02-O-198 (invertase) |
| 24 | Last 185 nucleotides of SEQ ID NO: 3 |
| 25 | Oligo 06-O-1536 |
| 26 | Oligo 06-O-1537 |
| 27 | Oligo 06-O-1538 |
| 28 | Oligo 06-O-1539 |
| 29 | Oligo 06-O-1541 |
| 30 | Oligo 06-O-1542 |
| 31 | Zm-HRA 3'probe |
| 32 | Zm-HRA 5' probe |
| 33 | GLYAT4621 probe |
| 34 | Oligo 06-O-1779 |
| 35 | Oligo 06-O-1782 |
| 36 | Oligo 06-O-1783 |

TABLE 28-continued

Summary Table of SEQ ID NOS

| SEQ ID NO | Description |
|---|---|
| 37 | Oligo 07-O-1877 |
| 38 | Oligo 07-O-1878 |
| 39 | Oligo 07-O-1879 |
| 40 | Oligo 07-O-1880 |
| 41 | Oligo 07-O-1946 |
| 42 | Oligo 07-O-1947 |
| 43 | Oligo 07-O-1948 |
| 44 | Oligo 07-O-1949 |
| 45 | Oligo 07-O-1950 |
| 46 | Left border genomic sequence (ud) |
| 47 | complete internal transgene (ud) |
| 48 | complete flanking and complete transgene insert (ud) |
| 49 | Left flanking genomic/complete transgene (ud) |
| 50 | Right flanking genomic/complete transgene (ud) |
| 51 | Oligo DP098-3'-f12 |
| 52 | Oligo DP098-3'-r12 |
| 53 | Oligo DP098-3'-p6 |
| 54 | Oligo DP098-f6 (forward) |
| 55 | Oligo DP098-r2 (forward) |
| 56 | Oligo DP098-p5 (probe) |
| 57 | Zm-HRA 3' probe (up#2) |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A maize plant comprising event DP-098140-6 having stably integrated into its genome a polynucleotide comprising SEQ ID NO: 5 and 6.

2. The maize plant of claim 1, wherein said plant is a progeny of a plant grown from seeds of ATCC Seed Deposit PTA-8296.

3. A transgenic seed comprising event DP-098140-6 having stably integrated into its genome a polynucleotide comprising SEQ ID NO: 5 and 6.

4. A transgenic seed of ATCC Seed Deposit PTA-8296.

5. A method of producing a glyphosate tolerant and ALS inhibitor tolerant plant comprising
breeding a plant comprising event DP-098140-6 having stably integrated into its genome a polynucleotide comprising SEQ ID NO: 5 and 6 or a plant that is a progeny of a plant grown from seeds of ATCC Seed Deposit PTA-8296,
and selecting progeny by analyzing for at least one polynucleotide comprising a DP-098140-6 specific region, wherein said polynucleotide comprises SEQ ID NO: 5 or 6.

6. The method of claim 5, wherein said polynucleotide comprises:
(a) a nucleotide sequence set forth in SEQ ID NO:48, 7, 8, 9, 10, 49, or 50; or
(b) a nucleotide sequence comprising a fragment of SEQ ID NO: 48, 7, 8, 9, 10, 49, or 50.

7. A method for controlling weeds in an area of cultivation comprising applying an effective amount of glyphosate and/or an ALS inhibitor to the area of cultivation having a maize plant comprising event DP-098140-6 having stably integrated into its genome a polynucleotide comprising SEQ ID NO: 5 and 6 or a maize plant that is a progeny of a maize plant grown from seeds of ATCC Seed Deposit PTA-8296 comprising event DP-098140-6.

8. The maize plant of claim 1, wherein said maize plant further has stably incorporated into its genome a second polynucleotide encoding a second polypeptide, wherein said second polypeptide imparts tolerance to glyphosate by a distinct mode of action than glyphosate N-acetyl transferase.

9. The maize plant of claim 8, wherein said second polypeptide encodes a glyphosate-tolerant 5-enol-pyruvylshikimate-3-phosphate synthase (EPSPS) polypeptide.

* * * * *